(12) United States Patent
Zhao et al.

(10) Patent No.: US 8,852,657 B2
(45) Date of Patent: Oct. 7, 2014

(54) CHROMONES AS THERAPEUTIC AGENTS

(75) Inventors: Ji-Fu Zhao, Olympia, WA (US); Julie Tseng-Crank, Lacey, WA (US); Mesfin Yimam, Kent, WA (US); Qi Jia, Olympia, WA (US)

(73) Assignee: Unigen, Inc., Lacey, WA (US)

( * ) Notice: Subject to any disclaimer, the term of this patent is extended or adjusted under 35 U.S.C. 154(b) by 394 days.

(21) Appl. No.: 11/971,523

(22) Filed: Jan. 9, 2008

(65) Prior Publication Data

US 2008/0166438 A1    Jul. 10, 2008

Related U.S. Application Data

(60) Provisional application No. 60/884,107, filed on Jan. 9, 2007.

(51) Int. Cl.
| | |
|---|---|
| *A61K 36/886* | (2006.01) |
| *A61K 36/00* | (2006.01) |
| *A61K 36/704* | (2006.01) |
| *A61K 31/7048* | (2006.01) |
| *A61K 31/35* | (2006.01) |
| *A61K 31/352* | (2006.01) |
| *A61K 36/48* | (2006.01) |
| *A61K 36/38* | (2006.01) |
| *A61K 36/489* | (2006.01) |

(52) U.S. Cl.
CPC ............ *A61K 31/352* (2013.01); *A61K 36/704* (2013.01); *A61K 31/7048* (2013.01); *A61K 31/35* (2013.01); *A61K 36/48* (2013.01); *A61K 36/886* (2013.01); *A61K 36/38* (2013.01); *A61K 36/489* (2013.01)
USPC .......................................... 424/744; 424/725

(58) Field of Classification Search
None
See application file for complete search history.

(56) References Cited

U.S. PATENT DOCUMENTS

| | | | |
|---|---|---|---|
| 4,598,069 A | 7/1986 | Hikino et al. | |
| 4,656,029 A | 4/1987 | Grollier et al. | |
| 4,725,438 A | 2/1988 | Leazer | |
| 4,851,224 A | 7/1989 | McAnalley | |
| 4,966,892 A | 10/1990 | McAnalley | |
| 5,106,616 A | 4/1992 | McAnalley et al. | |
| 5,118,673 A | 6/1992 | Carpenter et al. | |
| 5,308,838 A | 5/1994 | McAnalley et al. | |
| 5,468,737 A | 11/1995 | McAnalley et al. | |
| 5,503,825 A | 4/1996 | Lane | |
| 5,521,216 A | 5/1996 | Igarashi et al. | |
| 5,536,506 A | 7/1996 | Majeed et al. | |
| 5,587,364 A | 12/1996 | McAnalley et al. | |
| 5,589,182 A | 12/1996 | Tashiro et al. | |
| 5,627,204 A | 5/1997 | Igarashi et al. | |
| 5,703,060 A | 12/1997 | McAnalley et al. | |
| 5,708,038 A | 1/1998 | Davis | |
| 5,773,425 A | 6/1998 | McAnalley et al. | |
| 5,780,453 A | 7/1998 | McAnalley et al. | |
| 5,888,984 A | 3/1999 | Brown | |
| 5,939,395 A | 8/1999 | Yu et al. | |
| 6,083,976 A | 7/2000 | Padmapriya et al. | |
| 6,123,959 A | 9/2000 | Jones et al. | |
| 6,133,305 A | 10/2000 | Tang et al. | |
| 6,306,383 B1 | 10/2001 | Crandall | |
| 6,395,311 B2 | 5/2002 | Jia | |
| 6,451,357 B1 | 9/2002 | Farrow | |
| 6,780,440 B2 | 8/2004 | Naguib | |
| 6,884,783 B2 | 4/2005 | Jia et al. | |
| 7,678,772 B2 | 3/2010 | Jia et al. | |
| 2003/0207818 A1* | 11/2003 | Jia et al. | 514/27 |
| 2005/0164957 A1* | 7/2005 | Jia et al. | 514/27 |
| 2010/0168223 A1 | 7/2010 | Jia et al. | |
| 2013/0012458 A1 | 1/2013 | Jia et al. | |

FOREIGN PATENT DOCUMENTS

| | | | |
|---|---|---|---|
| CN | 1575803 A | | 2/2005 |
| CN | 1575803 A | * | 2/2005 |
| CN | 1861169 A | * | 11/2006 |
| EP | 0861595 | | 9/1998 |
| JP | 4-59773 A | | 2/1992 |
| JP | 10 101541 A | | 4/1998 |
| JP | 10140179 A | * | 5/1998 |
| JP | 2003 286185 | | 10/2003 |
| JP | 2003286185 A | * | 10/2003 |
| KR | 2002 0078202 | | 10/2002 |
| KR | 10-2005-0075906 A | | 7/2005 |
| SI | 20 073 A | | 4/2000 |

(Continued)

OTHER PUBLICATIONS

Park et al., Analysis of 13 phenolic compounds in Aloe species by high performance liquid chromatography, Phytochemical Analysis, vol. 9: 186-191, 1998.*

(Continued)

*Primary Examiner* — Qiuwen Mi
(74) *Attorney, Agent, or Firm* — Seed IP Law Group PLLC

(57) ABSTRACT

The identification and isolation of chromones and novel chromone compositions from plant sources that exhibit up-regulation of adiponectin production by adipocytes and the normalization of virtually hundreds of genes related to glucose and fatty acid metabolic and signaling pathways. The chromone compositions are effective in enhancing adiponectin production by adipocytes and regulating genes involved in fatty acid biosynthesis, mitochondrial β-oxidation of fatty acids, steroid biosynthesis, gluconeogenesis, fat transport, PPARα/RXRα liver signaling and xenobiotic metabolism. The chromone compositions can be used to increase insulin sensitivity, improve glucose tolerance, lower triglyceride levels and balance glucose levels in mammals. Included are methods for the prevention and treatment of a variety of diseases and conditions including, but not limited to insulin resistance, glucose intolerance, hyperglycemia, metabolic syndromes, dyslipidemia, and hypertriglyceridemia.

85 Claims, 44 Drawing Sheets

(56) References Cited

FOREIGN PATENT DOCUMENTS

| WO | WO 95/05169 | 2/1995 |
|---|---|---|
| WO | WO 95/23604 | 9/1995 |
| WO | WO 96/40182 | 12/1996 |
| WO | WO 01/30342 | 5/2001 |
| WO | WO 03/092713 A1 | 11/2003 |
| WO | WO 2004/037193 | 5/2004 |
| WO | WO 2004/066912 | 8/2004 |
| WO | WO 2006/024545 | 3/2006 |

OTHER PUBLICATIONS

Simpson et al., The prevention of type 2 diabetes—lifestyle change or pharmacotherapy? A challenge for the 21st century. Diabetes Research and Clinical Practice 59 (2003) 165-180.*
Kim et al, Properties and activity screening of chromone derivatives, Yakhak Hoeji, (Apr. 2000) vol. 44, No. 2, pp. 107-114.*
Annual Drug Data Report (1991) 13(7):583, "Platelet Antaggregatory Agents—RC-3911" (Abstract).
Blommaart et al. (1997) Eur. J. Biochem 243:240-246, "The phosphatidylinositol 3-kinase inhibitors wortmannin and LY294002 inhibit autophagy in isolated rat hepatocytes".
Budzianowski et al. (1991) Pol. J. Pharmacol. Pharm. 43:395-401, "Studies on Antioxidative Activity of Some C-Glycosylflavones".
Byeon et al. (1998) J. Investigative Dermatology 110:811-817, "*Aloe barbadensis* Extracts Reduce the Production of Interleukin-10 After Exposure to Ultraviolet Radiation".
Constantino et al. (Jun. 3, 1999) J. Med. Chem. 42(11):1881-1893, "1-Benzopyran-4-one Antioxidants As Aldose Reductase Inhibitors".
Grindlay and Reynolds (1986) J. of Ethnopharmacology 16:117-151, "The *Aloe vera* Phenomenon: A Review of the Properties and Modern Uses of the Leaf Parenchyma Gel".
Hart et al. (1988) J. of Ethnopharmacology 23:61-71, "Two Functionally and Chemically Distinct Immunomodulatory Compounds in the Gel of *Aloe vera*".
Henry (1979) Cosmetics & Toiletries 94:42-50, "An Updated Review of *Aloe vera*".
Hirati & Suga et al. (1977) Z. Naturforsch 32c:731-734, "Biologically Active Constituents of Leaves and Roots of *Aloe arborescens* var. *natalensis*".
Lee et al. (Feb. 1997) Biochem. Mol. Biol. Int. 41(2):285-292, "Aloesin Up-Regulates Cyclin E/CDK2 Kinase Activity Via Inducing the Protein Levels of Cycline E, CDK2, and CDC25A in SK-HEP-1 Cells".
Lee et al. (2000) Free Radic Biol. Med. 28(2):261-265, "Isolation and Identification of a Phenolic Antioxidant from *Aloe barbadensis*".
McKnight et al. (Jan. 2002), Resource Data and Case Studies on *Aloe vera*, International *Aloe* Science Council, Dallas, TX.
Tetko et al. (1995) Bioorg Khim. 21(10):809-815, "Evolutionary computation to reveal structure-activity relationships in 3-phenoxychrome and 3-phenoxy-4-hydroxycoumarin derivatives" (Abstract).
Witiak et al. (1975) J. Med. Chem. 18(9):934-942, "Synthesis of Ethyl 6-Substituted Chroman-and-Chromone-2-carboxylates. A Comparative Structure-Activity Study Employing the 6-Phenyl and Phenoxy Analogs in the Triton Hyperlipidemic Rat Model".
Yagi et al. (1987) Plant Medica 515-517, "Inhibition of Mushroom-Tyrosinase by *Aloe* Extract".
Yagi et al. (Nov. 2002) Planta Medica 68(11):957-960, "Antioxidant, Free Radical Scavenging and Anti-Inflammatory Effects of Aloesin Derivatives in *Aloe vera*".
Ajabnoor (1990) J. Ethnopharmacol. 28:215-220, "Effect of Aloes on Blood Glucose Levels in Normal and Alloxan Diabetic Mice".
Beppu (2006) J Ethnopharmacol. 103(3):468-477, "Antidiabetic effects of dietary administration of *Aloe arborescens* Miller components on multiple low-dose streptozotocin-induced diabetes in mice: Investigation on hypoglycemic action and systemic absorption dynamics of *Aloe* components".

Ghannam,(1986) Hormone Res. 24:288-294, "The Antidiabetic Activity of Aloes: Preliminary Clinical and Experimental Observations".
Hutter et al. (1996) J. Nat. Prod. 59:541-543, "Antiinflammatory C-Glucosyl Chromone from *Aloe barbadensis*".
Loots (2007) J Agric. Food Chem. 55(17):6891-6896, "*Aloe ferox* Leaf Gel Phytochemical Content, Antioxidant Capacity, and Possible Health Benefits".
Rajasekaran (2005) Biol. Trace Elem. Res. 108(1-3):185-195, "Mineral Contents of *Aloe vera* Leaf Gel and Their Role on Streptozotocin-Induced Diabetic Rats".
Rajasekaran (2005) Pharmacol. Rep. 57(1):90-96, "Antioxidant effect of *Aloe vera* gel extract in streptozotocin-induced diabetes in rats".
Rajasekaran (2006) Clin Exp Pharmacol Physiol. 33(3):232-237, "Beneficial Effects of *Aloe vera* Leaf Gel Extract on Lipid Profile Status in Rats with Streptozotocin Diabetes".
Tanaka (2006) Biol. Pharm. Bull. 29(7):1418-142, Identification of Five Phytosterols from *Aloe vera* Gel as Anti-diabetic Compounds.
Final Report on the Safety Assessment of *Aloe* Androgensis Extract, . . . (2007), International Journal of Toxicology, 26(1):1-50.
U.S. Appl. No. 12/721,371, filed Mar. 10, 2010, Jia et al.
Alves et al. (1999) Journal of Molecular Structure (Theochem) 491:123-131, "A Quantum Chemical and Statistical Study of Flavonoid Compounds with Anti-HIV Activity".
Annual Drug Data Report (1999) 21(9):770, "Psychopharmacologic Drugs—Antipsychotic Drugs—278844" (Abstract).
Cai (1996) J. Nat. Prod. 59:987-990, "Compounds from *Syzgium aromaticum* Possessing Growth Inhibitory Activity Against Oral Pathogens".
Conner et al. (1990) Phytochemistry 29:941, "Anthrone and Chromone Components of *Aloe cremnophila* and A. Jackson II Leaf Exudates".
Devi et al. (1999) Radiation Research 1(151):74-78, "In vivo Radioprotection by *Ocimum* Flavonoids: Survival of Mice".
Devi et al. (2000) Radiation Research 154(4):455-460, "Radiation Protection by the *Ocimum* Flavonoids Orientin and Vicenin: Mechanisms of Action".
Unigen Pharmaceuticals, Inc. Commercial Invoice U5169 (Sep. 22, 2005).
Erickson et al. (1992) J. Med. Chem. 35:1526-1535, "(Aminoalkoxy)chromones. Selective Receptor Ligands".
Fernandes et al. (2002) Journal of Enzyme Inhibition and Medicinal Chemistry 17(1):45-48, "2-Styrylchromones as Novel Inhibitors of Xanthine Oxidase. A Structure-Activity Study".
Fujimoto et al. (2002) Chem. Pharm. Bull. 50:330-336, "Five New Chromones Possessing Monoamine Oxidase Inhibitory Activity from an Ascomycete, *Chaetonium quadrangulatum*".
Fukyuasu et al. (1996) Chemical Abstracts Service, "Preventive Effects of Homonataloin and Aloesin on the UV-B Induced Immune Suppression. Investigation Using Contact Hypersensitivity Response" (Abstract).
Geiseg, (1999) New Zealand Science Monthly, pp. 6-8, "Reducing Free Radicals—A Dietary Revolution".
Haynes et al. (1970) J. Chem. Soc. (C) 2581, "C-glycosyl Compounds. Part VI. Aloesin a C-glucosylchromone from *Aloe* sp".
Holdsworth (1972) Dept. of Chem., Univ. of Papua and New Guinea, 322-325, "Chromones in *Aloe* Species".
Inaba et al. (2000) Chem. Pharm. Bull. 48:131-139, "Synthesis and Antiinflammatory Activity of 7-Methanesulfonylamino-6-phenoxychromes. Antiarthritic Effect of the 3-Formylamino Compound (T-614) in Chromic Inflammatory Disease Models".
Jong-Anurakkun (2008) Fitoterapria 79:456-457, "α-Glucosidase inhibitor from Chinese aloes".
Jurenka et al. (1989) Comp. Biochem. Physiol. 93C:253-255, "In Vitro Inhibition of Prostaglandin H Synthase by Compounds from the Exocrine Secretions of Lace Bugs".
Leoncini et al. (1991) Pharmacol. Res. 23(2):139-148, "Antiplatelet Effect of 2-(Diethylamino)-7-Hydroxychromone".
McCarthy et al. (1967) Heft 3:342, "The Distribution of Aloesin in some South African *Aloe* Species".
Mebe (1987) Phytochemistry 26(9):2646-2647, "2'-p-Methoxycoumaroylaloeresin, a C-Glucoside from *Aloe excelsa*".

(56) References Cited

OTHER PUBLICATIONS

Occhiuto et al. (1991) Phytotherapy Research 5(1):9-14, "Comparative Antiarrhythmic and Anti-Ischaemic Activity of Some Flavones in the Guinea-pig and Rat".
Office Action issued on Jan. 8, 2008 by U.S. Patent Office for U.S. Appl. No. 11/085,896.
Office Action sent on Aug. 7, 2008 by U.S. Patent Office for U.S. Appl. No. 11/085,896.
Office Action sent on May 4, 2009 by U.S. Patent Office for U.S. Appl. No. 11/085,896.
Office Action sent on Apr. 23, 2003 by U.S. Patent Office for U.S. Appl. No. 10/138,932.
Office Action sent on Jun. 29, 2004 by U.S. Patent Office for U.S. Appl. No. 10/138,932.
Office Action sent on Nov. 18, 2003 by U.S. Patent Office for U.S. Appl. No. 10/138,932.
Park et al. (1998) Phytochemical Analysis, 9:186-191, "Analysis of 13 Phenolic Compounds in *Aloe* species by High Performance Liquid Chromatography".
Piao et al. (2002) Chem. Pharm. Bull. 50:309-31, "Mushroom Tyrosiinase Inhibition Activity of Some Chromones".
Pong et al. (1998) J. Neurochem. 71:1912-1919 "Inhibition of Phosphatidylinositol 3-Kinase Activity Blocks Cellular Differentiation Mediated by Glial Cell Line-Derived Neutrophic Factor in Dopaminergic Neurons".
Prabhakar et al. (1978) Journal of Molecular and Cellular Cardiology 10(1):80, "Cardiovascular Effects of Vitexin" (Abstract).
Rauwald et al. (1993) J. of Chromatography 639:359-362, "High-performance liquid chromatographic separation and determination of diastereomeric anthrone-C-glucosyls in Cape aloes".
Rauwald et al. (1993) Z. Naturforsch 48c:1-4, "5-Hydroxyaloin a in the Genus *Aloe* Thin Layer Chromatographic Screening and High Performance Liquid Chromatographic Determination.".
Simpson et al. (2003) Diabetes Research and Clinical Practice; 59:165-180, "The prevision of type 2 diabetes—lifestyle change or pharmacotheraphy? A challenge for the 21st century".
International Search Report and Written Opinion issued in PCT/US2008/050600 on Jun. 17, 2008.
Stepanenko, "Kurs Organicheskoĭ Khimii," MEDGIZ, Moscow, 1955, p. 608, 10 pages total.
English Translation of Russian Office Action for corresponding Russian Patent Application No. 2009 130 132, dated Dec. 9, 2011, 6 pages.
Davis et al. (1991) JAPMA 81:1, "*Aloe vera* as a Biologically Active Vehicle for Hydrocortisone Acetate".
Office Action issued on Nov. 24, 1999 by U.S. Patent Office for U.S. Appl. No. 09/301,892, now U.S. Patent No. 6,395,311.
Office Action issued on Jun. 20, 2000 by U.S. Patent Office for U.S. Appl. No. 09/301,892, now U.S. Patent No. 6,395,311.
Office Action issued on Oct. 31, 2000 by U.S. Patent Office for U.S. Appl. No. 09/301,892, now U.S. Patent No. 6,395,311.
Office Action issued on Jan. 30, 2001 by U.S. Patent Office for U.S. Appl. No. 09/301,892, now U.S. Patent No. 6,395,311.
Office Action issued on Jul. 31, 2001 by U.S. Patent Office for U.S. Appl. No. 09/301,892, now U.S. Patent No. 6,395,311.
Office Action issued Feb. 3, 2011 in U.S. Appl. No. 12/721,371.
Conner et al., "Anthracene and Chromone Derivatives in the Exudate of *Aloe rabaiensis*," Phytochemistry 28(12): 3551-3553, 1989.
Dagne et al., "Chemistry of *Aloe* Species," Current Organic Chemistry 4(10): 1055-1078, 2000.
Gramatica et al., "*Aloe* Revisited: The Structure of Aloeresin A," Tetrahedron Letters 23(23): 2423-2424, 1982.
Groom et al., "Barbaloin in *Aloe* Species," Planta Med. 53(4): 345-348, 1987, abstract only, download https://www.thieme-connect.com/ejournals/abstract/10.1055/s-2006-962735 download date Dec. 27, 2012, 1 page.
Holdsworth, "Chromones in *Aloe* Species, Part II—Aloesone," PM 22(1): 54-58, 1972.
Kim et al., "Properties and Activity Screening of Chromone Derivatives," Yakhak Hoeji 44(2): 107-114, 2000, plus abstract, 9 pages.
Makino et al., "Studies on the Constituents of *Aloe arborescens* Mill. Var. *natalensis* Berger. II. The Structures of Two New Aloesin Esters," Chem. Pharm. Bull 22(7): 1565-1570, 1974.
Okamura et al., "Three Chromone Components from *Aloe vera* Leaves," Phytochemistry 43(2): 495-498, 1996.
Okamura et al., "Three Chromones of *Aloe vera* Leaves," Phytochemistry 45(7): 1511-1513, 1997.
Okamura et al., "Five Chromones from *Aloe vera* Leaves," Phytochemistry 49(1): 219-223, 1998.
Okyar et al., "Effect of *Aloe vera* Leaves on Blood Glucose Level in Type I and Type II Diabetic Rat Models," Phytotherapy Research 15: 157-161, 2001.
Pelley et al., "Current Status of Quality Control of *Aloe barbadensis* Extracts," SÖFW-Journal 119(5): 255-260, 1993.
Rajasekaran et al., "Hypoglycemic effect of *Aloe vera* gel on streptozotocin-induced diabetes in experimental rats," J. Med. Food 7(1): 61-66, Spring 2004, abstract only, 1page.
Ramachandra et al., "Processing of *Aloe vera* Leaf Gel: A Review," American Journal of Agricultural and Biological Sciences 3(2): 502-510, 2008.
Speranza et al., "Aloeresin C, A Bitter C,O-Diglucoside from Cape *Aloe*," Phytochemistry 24(7): 1571-1573, 1985.
Speranza et al., "A C-glucosylated 5-methylchromone from Kenya *Aloe*," Phytochemistry 25(9): 2219-2222, 1986.
Speranza et al., "Iso-Aloeresin A, A Minor Constitutent of Cape *Aloe*," Journal of Natural Products 51(3): 588-590, May-Jun. 1988.
Van Wyk et al., "Geographical Variation in the Major Compounds of *Aloe ferox* Leaf Exudate," Planta Med. 61: 250-253, 1995.
Yongchaiyudha et al., "Antidiabetic activity of *Aloe vera* L. juice. I. Clinical trial in new cases of diabetes mellitus," Phytomedicine 3(3): 241-243, 1996.
Zonta et al., "High-performance liquid chromatographic profiles of aloe constituents and determination of aloin in beverages, with reference to the EEC regulation for flavouring substances," Journal of Chromatography A 718: 99-106, 1995.
Third Party Observations, dated Jan. 18, 2011, for EP Patent Application No. 03733934.8, 7 pages.

\* cited by examiner

CHROMONES AS THERAPEUTIC AGENTS

RELATED APPLICATIONS

This application claims the benefit of U.S. Provisional Application Ser. No. 60/884,107, filed Jan. 9, 2007, entitled "Compounds Isolated from *Aloe* Species as Glucose Lowering and Anti-Diabetic Agents," which is incorporated herein by reference in its entirety.

FIELD OF THE INVENTION

This invention relates generally to the isolation and identification of chromones and novel chromone compositions that are effective in enhancing adiponectin production by adipocytes, and regulating genes involved in fatty acid biosynthesis, mitochondrial β-oxidation of fatty acids, steroid biosynthesis, gluconeogenesis, fat transport, PPARα/RXRα liver signaling and xenobiotic metabolism. Included are methods for the prevention and treatment of insulin resistance, glucose intolerance, hyperglycemia, metabolic syndromes, dyslipidemia, and hypertriglyceridemia.

BACKGROUND OF THE INVENTION

Obesity, diabetes, and metabolic syndrome have rapidly become a global epidemic. According to the World Health Organization (WHO) publication, in 2005 approximately 400 million adults were obese, and it is projected that by 2015 more than 700 million adults will be obese. Obesity is a major risk factor for a number of chronic diseases, including cardiovascular disease and diabetes.

Metabolic syndrome was first described by Reaven in 1988 (Reaven (1988) Diabetes 37:1595-1607) as a cluster of interrelated common clinical disorders, including obesity, insulin resistance, glucose intolerance, hypertension, and dyslipidemia (hypertriglyceridemia and low HDL cholesterol levels). The Adult Treatment Panel III (ATP III) of the National Cholesterol Education Program established criteria for diagnosing metabolic syndrome in 2001 (JAMA (2001) 285: 2486-249797). Five criteria were selected by the ATP III to identify individuals with metabolic syndrome including abdominal obesity, impaired fasting glucose, high triglyceride (TG), low HDL cholesterol (HDL-C) concentrations, and increased blood pressure. Metabolic syndrome is diagnosed, if any three of the components are present in an individual. Metabolic syndrome is highly prevalent worldwide and is associated with a greater risk of atherosclerotic cardiovascular disease than any of its individual components.

Analysis of data on 8814 men and women aged 20 years or older from the Third National Health and Nutrition Examination Survey (1988-1994) revealed that the unadjusted and age-adjusted prevalence of the metabolic syndrome was 21.8% and 23.7%, respectively. Using 2000 census data, about 47 million US residents may have the metabolic syndrome (Ford et al. (2002) JAMA 16:359). In obese children and adolescents, the prevalence of the metabolic syndrome is very high, increasing with the severity of obesity and reaching 50 percent in severely obese youngsters (Weiss et al. (2004) "Obesity and the metabolic syndrome in children and adolescents." N Eng J Med 350:2362-2374). Biomarkers of an increased risk of adverse cardiovascular outcomes are already present in these youngsters. The metabolic syndrome and its individual components are not only found in obese populations, but are found in normal-weight and slightly overweight individuals as well.

Compelling evidence suggests that insulin resistance is the root of the problem of the metabolic disorders (Reaven G M. (1998) Diabetes 37:1595-1607). The prevalence of metabolic syndrome increases significantly with increasing insulin resistance (P<0.001 for trend) after adjustment for race or ethnicity and the degree of obesity (Weiss et al. (2004) "Obesity and the metabolic syndrome in children and adolescents." N Eng J Med 350:2362-2374). Insulin resistance is a state of reduced responsiveness to normal circulating concentrations of insulin (Saltiel A R (2000) J Clin. Invest. 106:163-164) and a major etiology of type 2 diabetes. Insulin resistance is related to obesity, lifestyle factors and genetic factors (Kadowaki T (2000) J Clin. Invest. 106:459-465; Stern M (2000) J Clin. Invest. 106:323-327). Animal studies clearly demonstrate that genetic defects of insulin receptor and insulin signaling pathways are involved in the pathogenesis of insulin resistance in type 2 diabetes. For example, insulin action deficiency was obvious in muscle, liver and adipose tissues of the insulin receptor knockout mice. These mice also showed hyperinsulinemia and severe diabetes. The mice with increased activity of PI3 kinase (PI3K), which is a key signaling enzyme in the insulin signal transduction cascade, showed increased insulin sensitivity and hypoglycemia due to increased glucose transport in skeletal muscle and adipocytes (Kadowaki T (2000) J Clin. Invest. 106:459-465). Similarly, mice deficient in Akt2, a kinase downstream of PI3K, exhibited decreased insulin resistance and increased muscle glucose transport (Cho et al. 2001 Science 292:1728).

In humans, recent studies are rich in the genetic basis and physiology of insulin resistance and diabetes. Subjects with partial "loss-of-function" Pro12Ala mutation in PPAR gamma2-specofoc B exon have a combination of lower BMI, greater insulin sensitivity and improved lipid profiles (Deeb et al. (1998) Nat Genet 20:284-287; Alhuler et al. (2000) Nat Genet 26:76-80). The physiological consequences of the Pro12Ala polymorphism are largely dependent on confounding genetic and environmental factors. Subjects with the Pro115Gln gain-of-function mutation are extremely obese and insulin sensitive (Ristow et al. (1998) N Engl J Med 339:953-959), which is consistent with the effect of PPARγ in stimulating adipocyte differentiation. On the other hand, dominant-negative mutations, such as Pro495Leu, Val318Met, Phe388Leu and Arg425Cys, are associated with partial lipodystrophy, severe insulin resistance, diabetes, and hypertension (Savage et al. (2003) Diabetes 52:910-917; Agawal and Garg (2002) J Clin Endocrinol Metab 87:408-411).

The human genetic disease, maturity-onset diabetes of the young (MODY), is characterized by a clinical onset of diabetes before age 25, an autosomal dominant mode of inheritance, and a primary defect in the function of the pancreatic β cells. Six MODY genes had been identified: MODY1, hepatocyte nuclear factor-4α(HNF-4α); MODY2, glucokinase; MODY3, HNF-1α, MODY4, insulin promoter factor-1 (IPF-1); MODY5, HNF-1β; and MODY6, beta-cell E-box transactivator or NeuroD1 (Fajans et al. (2001) N Engl J Med 345:971). MODY genes are involved in abnormal gene expression and glucose metabolism in the pancreatic β cells leading to β cell dysfunction.

Type II diabetes is complex and heterogeneous, a multifactorial disease. Rare monogenic forms of MODY, although informative regarding diabetic pathophysiology, can not capture the spectrum of human diabetic etiology. Human genome-wide scans were used by many genomics research groups to search for diabetes and insulin resistance loci among various susceptible ethnic populations using genetic polymorphism (McIntyre and Walker (2002) Clin Endocrinol 57:303). The calpain-10 gene on chromosome 15 was the first gene identified using a genome-wide scan of 252 sib-pairs of a Mexican-American ethnic group in Texas and later confirmed using studies of other ethnic groups. Clinical studies suggest that calpain-10 is one of the factors affecting the action of insulin on muscle tissue and the secretion of insulin from the pancreatic β cell. Studies in mice lacking calpain-10 suggest that calpain-10 mediates fatty acid-induced apoptosis in insulin-secreting pancreatic β cells (Horikawa et al. (2000) Nat Genet 26:163; Weedon et al. (2003) Am J Hum Genet 73:1208). The search for human diabetic genes is far from over, FTO on chromosome 16 is a recent discovery. FTO with unknown function was associated with BMI and was confirmed in various diabetes study populations totaling 39,000 people (Kaiser (2007) Science 316:185). In addition, by association studies of candidate genes, KCNJ111 (the inward-rectifier subunit of the β-cell ATP-sensitive potassium channel) and HNF-4α genes were also found to be NIDDM genes (Taylor (2007) Diabetes 56:2844).

Free fatty acid (FFA) is perhaps the most important factor in the pathophysiology of insulin resistance. Non-invasive magnetic resonance spectroscopy has been used in clinical studies using $^{13}C$, $^{31}P$, and $^{1}H$ isotopes to track muscle glycogen synthesis, glucose uptake, and glucose-6-phosphate concentration by Shulman's group at Yale University. In healthy human subjects under hyperinsulinemic-euglycemic clamps, using lipid infusion to maintain a high blood FFA level, insulin resistance gradually developed, reaching a 50% reduction in insulin-stimulated muscle glucose uptake and a 50% reduction in muscle glycogen synthesis and glucose oxidation after 4-6 hours of lipid infusion, accompanied by a >90% decrease in the insulin-stimulated IRS-1-associated PI3K activity (Roden et al. (1996) J Clin Invest 97:2859; Dresner et al. (1999) J Clin Invest 103:253).

Peroxisome proliferator-activated receptors (PPARs) are a subclass of the nuclear receptor super-family. PPARs are ligand-dependent transcription factors that bind to specific DNA response elements as heterodimers with the retinoid X receptor. This ligand binding leads to preferential recruitment of chromatin-decondensing coactivator complexes and favors dismissal of the corepressor complex (Glass (2006) J. Clin. Invest. 116:556-560 doi:10.1172/JCI129713). In addition, PPARs may influence gene expression indirectly, and usually negatively, through competition with other transcription factors (Gervois et al. (2001). J. Biol. Chem. 276:33471-33477). There are three members in the PPAR family: PPARα, PPARδ (or PPARβ) and PPARγ. Extensive experimental evidence links the three nuclear receptors to the regulation and coordination of lipid and carbohydrate metabolism. The association of the three proteins with various diseases including diabetes, obesity, dyslipidemia and inflammation is well established. The three PPARs are differentially expressed in different tissues (Semple et al. (2006). J. Clin. Invest. 116: 556-560 doi: 10.1172/JCI128003). PPARα has the highest expression in the liver, kidneys and the heart. PPARγ is preferentially expressed in adipose tissue and in macrophages. The expression of PPARδ is widely spread, but with the highest expression in adipose tissue, skin and brain. The three nuclear receptors are involved in various cellular processes. Activation of PPARα or PPARδ leads to increased fatty acid β oxidation. PPARα is implicated in lipoprotein synthesis and amino acid catabolism. PPARγ is critical in adipocyte differentiation. The proteins have different physiological functions. PPARα coordinates metabolic response of tissues to fasting, whereas the expression of PPARγ increases postprandially and its activation leads to up-regulation of genes that mediate fatty acid uptake in adipose tissues. PPARγ is the key transcriptional factor that orchestrates adipocyte differentiation. The physiological function PPARδ is not completely understood. However, recent evidence indicates that it may be a regulator of muscle fiber type and activation of the protein leads to resistance to obesity and improved metabolic profiles (Wang et al. (2004). PloS Biology 2:e294).

Multiple pathways may be involved in insulin resistance. PPARγ activation in adipose tissues up regulates the transcription of genes involved in fatty acids trapping (Semple et al. (2006) J. Clin. Invest. 116:556-560 doi:10.1172/ JCI128003). PPARγ activates the endothelial lipoprotein lipase (LPL) and the fatty acid transport proteins (FATP and CD36), which promote hydrolysis of lipoprotein triglyceride and uptake of FFA into adipocytes, respectively. The process enhances insulin sensitivity by reducing lipid in the circulation and the direct access of lipid to the insulin sensitive tissues, such as muscle and liver ((Semple et al. (2006) J. Clin. Invest. 116:556-560 doi:10.1172/JCI128003). PPARγ has been well characterized. The essential role of PPARγ was demonstrated in embryonic lethality of the homozygous PPARγ-deficient mice (Tsuchida et al. (2005) J Pharmacol. Sci. 97:164-170). In wild-type mice, obesity and insulin resistance can be induced by high fat diets. However, the high-fat diet induced obesity or insulin resistance is prevented in heterozygous PPARγ-deficient mice (Tsuchida et al. (2005) J Pharmacol. Sci. 97:164-170). For example, the heterozygous PPARγ (+/−) mice were fed a high-fat diet, the mice were less insulin resistant and had smaller adipocytes than wild-type mice. The mice also had lower levels of fatty acids and increased levels of leptin in plasma (Kubota et al. (1999) Mol Cell 4:597-609; Tsuchida et al. (2005) J Pharmacol. Sci. 97:164-170). The protective effect of the heterozygous PPARγ-deficiency, however, was diminished by treating the mice with PPARγ agonists. The thiazolidinedione (TZD) class of insulin sensitizing drugs (Lehmann et al. (1995). J. Biol. Chem. 270:12953-12956) paradoxically decreases the insulin sensitivity of PPARγ (+/−) mice. These results suggest that PPARγ mediates high-fat diet induced obesity and insulin resistance, and inhibition of PPARγ could render animals, or people, less susceptible to endogenous and exogenous causes of insulin resistance. On the other hand, supra-physiological activation of PPARγ by TZD in wild-type mice fed with high fat diet improved insulin sensitivity as well, but induced adipocyte differentiation at the same time. The experimental evidence indicates that both down-regulation and up-regulation of PPARγ activity improve insulin sensitivity.

PPARα is a molecular sensor of endogenous fatty acids and their derivatives. It plays a key role in glucose homoeostasis and lipid metabolism in the liver and skeletal muscle. It has been demonstrated that PPARα agonists, such as fibrates, are efficacious in lipid lowering (Lefebvre et al. (2006). J. Clin. Invest. 116:571-580. doi:10.1172/JCI27989). In rodents, a PPARα agonist, Wy14643, improved insulin sensitivity in KKAy mice and enhanced the anti-diabetic effect of PPARγ agonist rosiglitazone (Tsuchida et al. (2005) Diabetes 54:3358-3370). Adipocyte hypertrophy was prevented by Wy14643 (Tsuchida et al. (2005) Diabetes. 54:3358-3370).

PPARδ has recently emerged as a metabolic regulator in various tissues including fat, skeletal muscle, and the heart (Barish et al. (2006) J. Clin. Invest. 116: 590-597). It enhances fatty acid catabolism and energy uncoupling, which leads to decreased triglyceride storage and improved endurance. The targeted expression of an activated form of PPARδ in skeletal muscle in mice conferred resistance to obesity with improved metabolic profiles (Wang et al. (2004). PloS Biology 2:1532-1539).

Modulating PPAR activity in the body is critical to maintaining normal insulin sensitivity in response to diet and other environmental impacts. Mouse genetic studies offer great opportunities to understand the complex interaction of the nuclear receptors and environmental factors. PPAR activity can be regulated by different modulators. PPARs interact with different ligands, leading to activation of different sets of the target genes. As a result, different transcriptional activities and pharmacological profiles are generated due to different affinity and effects of the modulators to PPARs. Modulators of PPARs can be divided into several groups, including full agonist, partial agonist, antagonist and coagonist (Knouff and Auwerx (2004) Endocrine Review 25:899-918).

Many PPAR full agonists have been developed. Rosiglitazone and piogliteazone are two TZDs that are used clinically in the treatment of type 2 diabetes (Lehmann et al. (1995) J Biol. Chem 270:12953-12956). Though these PPARγ agonists reduce insulin resistance and lower plasma glucose levels, the full agonists have severe side effects including weight gain due to increased fat mass and edema, fluid retention, hemodilution, and heart failure in up to 15% of patients (Mudaliar et al. (2003). Endocr. Pract. 9:406-416). Some TZDs are also associated with significant liver toxicity. Drug therapies that prevent or treat multiple aspects of the metabolic syndrome are limited in options and in success rate, although new molecular drug targets have been actively pursued.

Other insulin sensitization pathways involve modified profiles of adipokines produced from adipocytes including TNFα, IL-6, CRP, PAI-1, angiotensinogen, resistin, leptin and adiponectin (Lau et al. (2004). Am. J. Physiol Heart Cir. Physiol 288:H2031-H2041). These adipokines have profound effects on insulin resistance and vascular homeostasis. Among these proteins, adiponectin is one of the best-characterized hormones from adipocytes that mediate insulin sensitization. TZDs stimulate adiponectin gene expression and increase circulating adiponectin concentrations in obese mice and insulin resistant obese humans (Maeda et al. (2001) Diabetes 50:2094-2099). Because adiponectin improves glucose tolerance by increasing insulin sensitivity, the effect of TZDs on adiponectin secretion may explain, at least partially, the hypoglycemic effect of TZDs in patients with type 2 diabetes mellitus.

Additional pathways are involved in insulin sensitization in humans. For example, leptin was also shown to improve insulin sensitivity in rodents. In lipoatropic mice, administration of a combination of physiological doses of adiponectin and leptin led to complete restoration of insulin sensitivity, but only partial insulin sensitization was observed by either adiponectin or leptin treatment individually (Yamauchi et al. (2001). Nat Med 7:941-946). Leptin reduces the expression of lipogenic enzymes and consequently activates the PPARα pathway in the liver, brown adipose tissue and skeletal muscle, which lead to increased expression of UCP-2 and the enzymes involved in beta-oxidation. In humans, plasma adiponectin concentrations were not changed in individuals with improved insulin sensitivity by weight loss (Abbasi et al. (2004) Metabolism 53:280-283). In another study, it was demonstrated that improvements in insulin sensitivity by exercise training were not the results of the change of adiponectin levels in humans (Marcell et al. (2005), Metabolism 54:533-41). The data suggest that additional pathways exist for insulin sensitization and different mechanisms are involved in the improvement of insulin sensitivity after weight loss and after treatment with TZD compounds.

Chromones are a specific type of aromatic compounds having a benzopyran-4-one as their major skeletal structure as illustrated by the following general structure:

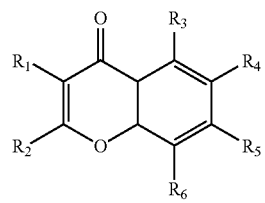

wherein
$R_1$, $R_2$, $R_3$, $R_4$, $R_5$ and $R_6$ are independently selected from the group consisting of —H, —OH, —CH$_3$, —SH, alkyl, alkenyl, oxoalkyl, oxoalkenyl, hydroxylalkyl, hydroxylalkenyl, —OCH$_3$, —SCH$_3$, —OR, —SR, —NH$_2$, —NRH, —NR$_2$, —NR$_3^+$X$^-$, an ester selected from the group consisting of gallate, acetate, cinnamoyl and hydroxyl-cinnamoyl esters, trihydroxybenzoyl esters and caffeoyl esters; and a hexose or pentose, wherein said hexose or pentose is linked to the chromone by a carbon, nitrogen sulfur or oxygen and wherein said hexose or pentose is selected from the group consisting of aldopentoses, methyl aldopentose, aldohexoses, ketohexose and their chemical derivatives thereof; including a dimer, trimer and other polymerized chromones;

wherein said alkyl and/or alkenyl group is a straight and/or branched chain having between 1-20 carbon atoms with and/or without double bonds and substitution group(s) selected from the group consisting —OH, =O and —OR in different positions;

X is selected from the group of pharmaceutically acceptable counter anions including, but not limited to hydroxyl, chloride, iodide, sulfate, phosphate, acetate, fluoride, carbonate, etc.; and R is an alkyl group having between 1-20 carbon atoms. To date there are only 183 chromones isolated from natural sources (The Combined Chemical Dictionary, Chapman & Hall/CRC, Version 5:1 June 2001).

Chromones reportedly exhibit monoamine oxidase inhibitory activity (Fujimoto et al. (2002) Chem. Pharm. Bull. 50:330-336), tyrosinase inhibitory activity (Oiao et al. (2002) Chem. Pharm. Bull. 50:309-311), anti-platelet effects (Leoncini et al. (1991) Pharmacol. Res. 23:139-148), growth inhibitory activity against oral pathogens (Cai (1996) J. Nat. Prod. 59:987-990), prostagladin H synthase inhibitory activity (Jurenka et al. (1989) Comp. Biochem. 93:253-255). Chromones also possess therapeutic efficacy against type II collagen-induced arthritis in rats (Inaba et al. (2000) Chem. Pharm. Bull. 48:131-139) and hypolipidemic activity (Witiak et al. (1975) J. Med. Chem. 18:935-942; Tetko et al. (1995) Bioorg Khim. 21:809-815). It has also been reported that chromones can function as selective sigma receptor ligands (Erickson et al. (1992) J. Med. Chem. 35:1526-1535). Based on animal studies, chromones are easily absorbed and metabolized (Crew et al. (1976) Xenobiotica 6:89-100) and the c-glucosyl bond of aloesin can be cleaved by human intestinal bacteria (Che et al. (1991) Chem. Pharm. Bull. 39:704-708).

*Aloe* is an intricate plant that contains many biologically active substances. (Dagne et al. (2000) Current Org. Chem. 4:1055-1078; Cohen et al. in *Wound Healing/Biochemical and Clinical Aspects*, 1st ed. WB Saunders, Philadelphia (1992)). Over 300 species of *Aloe* are known, most of which are indigenous to Africa. Studies have shown that the biologically active substances are located in separate sections of the aloe leaf—a clear gel fillet located in the center of the leaf, in the leaf rind or cortex of the leaf and in a yellow fluid contained in the pericyclic cells of the vascular bundles, located between the leaf rind and the internal gel fillet, referred to as the aloe latex (Dagne et al. (2000) Current Org. Chem. 4:1055-1078). The clear gel fillet, which is located in the center of the leaf contains water soluble polysaccharides, organic acids, amino acids and inorganic salts. *Aloe vera* gel is produced from this part of aloe plants. The leaf rind or cortex of the leaf, and the yellow fluid contained in the pericyclic cells of the vascular bundles, contain aromatic compounds such as anthraquinones, chromones, organic acids, enzymes, vitamins, salts and other miscellaneous compounds. *Aloe* whole leaf gel is produced by grinding the whole aloe plant which includes the contents of all water soluble components including anthraquinones, chromones, polysacchairdes and other compounds. Due to the color and phototoxicity, GI irritation, cytotoxicity and other side effects of anthraquinones, aloe whole leave gel is processed to remove all aromatic components including anthraquinones and chromones (International J. Toxicology (2007), 26 (suppl.2):1-50).

Historically, *Aloe* products have been used in dermatological applications for the treatment of burns, sores and other wounds. These uses have stimulated a great deal of research in identifying compounds from *Aloe* plants that have clinical activity, especially anti-inflammatory activity. (See, e.g., Grindlay and Reynolds (1986) J. of Ethnopharmacology 16:117-151; Hart et al. (1988) J. of Ethnopharmacology 23:61-71). As a result of these studies there have been numerous reports of *Aloe* compounds having diverse biological activities, including anti-tumor activity, anti-gastric ulcer, anti-diabetic, anti-tyrosinase activity and antioxidant activity (International J. Toxicology (2007), 26 (suppl.2): 1-50).

Chromones isolated from various *Aloe* species have been reported to have diverse biological activity. Aloesin reportedly inhibits tyrosinase activity (Jones et al. Journal of Pigment Cell Research, Acceptance, Feb. 10, 2002) and up-regulates cyclin E-dependent kinase activity (Lee et al. (1997) Biochem. Mol. Biol. Int. 41:285-292). A c-glycosyl chromone isolated from *Aloe barbadensis* demonstrates anti-inflammatory activity (Hutter et al. (1996) J. Nat. Prod. 59:541-543) and antioxidant activity similar to that of alpha-tocopherol based on a rat brain homogenates model (Lee et al. Free Radic Biol. Med. 28:261-265).

*Aloe barbadensis* leaves and its bitter principles exhibit effects on blood glucose level in normal and alloxan diabetic mice (Ajabnoor (1990) J. Ethnopharmacol. 28:215-220) and the dried sap of various *Aloe* species demonstrates anti-diabetic activity in clinical studies (Ghannam, (1986) Horm Res. 24:288-294). The anti-diabetic effects of aloe gel or extract have been demonstrated on low-dose streptozotocin-induced diabetes animal models (Beppu (2006) J Ethnopharmacol. 103(3):468-77; Rajasekaran (2006) Clin Exp Pharmacol Physiol. 33(3):232-7). Such anti-diabetic effects were reported as protection of low-dose streptozotocin-induced selective toxicity to B cells of islets by phenols and other molecular weight less than 10 KDa compounds (Rajasekaran (2006) Clin Exp Pharmacol Physiol. 33(3):232-7). Other components such as inorganic minerals (Rajasekaran (2005) Biol. Trace Elem. Res. 108(1-3):185-195) and anti-oxidants from *Aloe Vera* gel were reported in association with anti-diabetic effects (Rajasekaran (2005) Pharmacol. Rep. 57(1): 90-96).

Recently, five phytosterols from *Aloe vera* gel were identified as anti-diabetic components (Tanaka (2006) Biol. Pharm. Bull. 29(7):1418-1422). In 2007, the chemical components of *Aloe ferox* leaf gel were thoroughly analyzed with potent anti-oxidation properties reported and potential usage in alleviating symptoms and/or preventing diabetes speculated (Loots (2007) J Agric. Food Chem. 55(17):6891-6896).

U.S. Pat. No. 6,780,440 discloses herbal compositions including aloe for diabetes and weight management. However, the principle active components and the mechanism of action were not identified. In U.S. Pat. No. 588,984, complex carbohydrates from aloe were claimed as one of the compositions for treatment of diabetes. Also in U.S. Pat. No. 4,598, 069, aloe polysaccharides were claimed for treatment of hypoglycemia. U.S. Pat. No. 5,627,204 discloses synthetic chromone derivatives with different substitution patterns that acted as inhibitors of aldose reductase for use in the prevention and treatment of diabetes. U.S. Pat. No. 6,133,305 claimed synthetic compounds having the chromone skeleton for treating a protein kinase related disorders including diabetes.

Yagi et al. disclose a group of compounds isolated from *Aloe*, particularly aloesin and one of its derivatives, 2"-O-feruloylaloesin, which are effective inhibitors of tyrosinase. (Yagi et al. (1987) Plant Medica 515-517). Aloesin is a C-glucosylated 5-methylchromone (Holdsworth (1972) *Chromones in Aloe Species, Part I-Aloesin* PM 19(4):322-325). In vitro, aloesin is a strong inhibitor of tyrosinase activity (Yagi et al. (1987) Planta Medica 515-517). U.S. Pat. No. 6,123,959, entitled "Aqueous Composition Comprising Active Ingredients for the De-Pigmentation of the Skin," describes aqueous compositions comprising liposomes of phospholipids, and at least one competitive inhibitor of an enzyme for the synthesis of melanin, in combination with at least one non-competitive inhibitor of an enzyme for the synthesis of melanin. U.S. Pat. No. 6,884,783 disclosed 7-hydroxy chromones, including aloesin and aloesinol as potent antioxidants for prevention and treatment diseases and conditions associated with reactive oxygen species (ROS) damage and other oxidative stress.

To date, known methods for purifying aloesin, as well as, other chromones involve the use of chromatography. (See e.g., Rauwald and Beil (1993) J. of Chromatography 639: 359-362; Rauwald and Beil (1993) Z. Naturforsch 48c: 1-4; Conner et al. (1990) Phytochemistry 29:941; Holdsworth (1972) *Chromones in Aloe Species, Part I-Aloesin* PM 19(4): 322-325; Mebe (1987) Phytochemistry 26:2646; Haynes et al. (1970) J. Chem. Soc. (C) 2581; McCarthy and Haynes (1967) *The Distribution of Aloesin in Some South African Aloe Species*; Heft 3 342). These procedures were developed for chemical analysis and are not practical for preparative scale production of aloesin. In U.S. Pat. No. 6,451,357, entitled "Method of Purification of Aloesin," a method for purification of aloesin using crystallization is disclosed.

SUMMARY OF THE INVENTION

The present invention describes the identification and isolation of chromones and novel chromone compositions from plant sources that exhibit up-regulation of adiponectin production by adipocytes and the normalization of virtually hundreds of genes related to glucose and fatty acid metabolic and signaling pathways. The chromone compositions are effective in enhancing adiponectin production by adipocytes and regulating genes involved in fatty acid biosynthesis, mitochondrial β-oxidation of fatty acids, steroid biosynthesis, gluconeogenesis, fat transport, PPARα/RXRα liver signaling and xenobiotic metabolism. The chromone compositions can be used to increase insulin sensitivity, improve glucose tolerance, lower triglyceride levels and balance glucose levels in mammals. Included in the present invention are methods for the prevention and treatment of a variety of diseases and conditions including, but not limited to insulin resistance, glucose intolerance, hyperglycemia, metabolic syndromes, dyslipidemia, and hypertriglyceridemia.

The present invention includes methods for the prevention and treatment of metabolic syndrome and diseases and conditions mediated by insulin resistance in mammals. The method is comprised of administering to a subject in need thereof an effective amount of a pharmaceutical or a nutraceutical composition comprising one or more chromones. The chromone or mixture of chromones may be isolated from a single source or multiple sources, including but not limited to, synthetically obtained, naturally occurring, or any combination thereof.

In one embodiment the present invention describes a method for increasing adiponectin production from adipocytes comprising administering to a subject in need thereof an effective amount of a chromone or a mixture of chromones; wherein said chromone or a mixture of chromones. In another embodiment, the present invention describes a method for normalizing high fat diet induced changes of gene expressions of fatty acid biosynthesis, mitochondria β-oxidation of fatty acids, steroid biosynthesis, gluconeogenesis, fat transport, PPARα/RXRα liver signaling and xenobiotic metabolism, said method comprising administrating to a subject in need thereof an effective amount of a composition comprising a chromone or a mixture of chromones. In yet another embodiment the present invention includes a method for preventing and treating insulin resistance, glucose intolerance, hyperglycemia, metabolic syndromes, dyslipidemia, and hypertriglyceridemia, said method comprising administrating to a subject in need thereof an effective amount of a composition comprising a chromone or a mixture of chromones.

The chromones that can be used in accordance with the following include compounds illustrated by the following general structure:

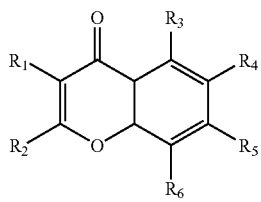

wherein $R_1$, $R_2$, $R_3$, $R_4$, $R_5$ and $R_6$ are independently selected from the group consisting of —H, —OH, —CH$_3$, —SH, alkyl, alkenyl, oxoalkyl, oxoalkenyl, hydroxylalkyl, hydroxylalkenyl, —OCH$_3$, —SCH$_3$, —OR, —SR, —NH$_2$, —NRH, —NR$_2$, —NR$_3^+$X$^-$, an ester selected from the group, including but not limited to gallate, acetate, cinnamoyl and hydroxyl-cinnamoyl esters, trihydroxybenzoyl esters and caffeoyl esters; and a hexose or pentose, wherein said hexose or pentose is linked to the chromone by a carbon, nitrogen sulfur or oxygen and wherein said hexose or pentose is selected from the group including but not limited to aldopentoses, methyl aldopentose, aldohexoses, ketohexose and chemical derivatives thereof; including a dimer, trimer and other polymerized chromones;

wherein said alkyl and/or alkenyl group is a straight and/or branched chain having between 1-20 carbon atoms with and/or without double bonds and substitution group(s) selected from the group consisting —OH, =O and —OR in different positions;

X is selected from the group of pharmaceutically acceptable counter anions including but not limited to hydroxyl, chloride, iodide, sulfate, phosphate, acetate, fluoride, carbonate; and R is an alkyl group having between 1-20 carbon atoms and a pharmaceutically acceptable carrier.

In one embodiment the chromone(s) is a benzopyran-4-one (7-hydroxy chromone) selected from the group compounds having the following general structure:

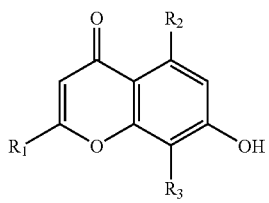

wherein $R_1$, $R_2$, and $R_3$ are as defined above.

In another embodiment of this invention the chromone is selected from aloesin and/or aloesinol whose structures are depicted below.

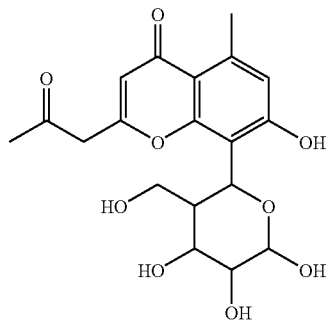

Aloesin

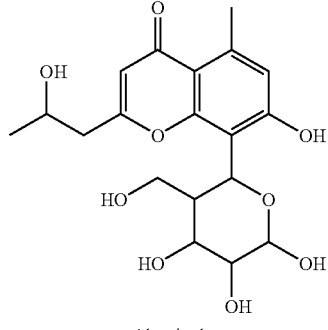

Aloesinol

The chromones of this invention may be obtained by synthetic methods or may be isolated from the genera of numerous plant families, including but not limited to *Acacia, Adina, Aloe, Alternaria, Amoora, Antidesma, Artemisia, Baeckea, Cassia, Clusea, Cnidium, Convolvulus, Epimedium, Eriosema, Eriostemon, Eugenia, Garcinia, Hypericum, Lindenbergia, Pancratium, Penicillium, Polygonum, Ptaeroxylon, Rheum, Sophora, Stephanitis, Syzygium, Talaromyces* and *Zonaria*. In preferred embodiments, the plant is selected from the group, including but not limited to, *Acacia catechu, Aca-* cia concinna, Aloe arborescens, Aloe barbadensis, Aloe cremnophila, Aloe ferox, Aloe saponaria, Aloe vera, Aloe vera var. chinensis, Antidesma membranaceum, Artemisia capillaries, Baeckea frutescens, Epimedium sagittatum, Garcinia dulcis, Hypericum japonicum, Polygonum cuspidatum, Sophora tomentosa and Stephanitis rhododendri. In one embodiment the chromones are isolated from the whole leaves of Aloe ferox, Aloe vera, or Aloe barbadensis.

The chromones can be found in various parts of the plant, including but not limited to stems, stem barks, trunks, trunk barks, twigs, tubers, roots, root barks, young shoots, seeds, rhizomes, flowers and other reproductive organs, leaves and other aerial parts.

The present invention describes the isolation and purification of chromones, from plants containing these compounds. The method of the present invention comprises: a) extracting the ground biomass of a plant containing a chromone, particularly a chromone selected from aloesin or aloesinol; b) neutralizing and concentrating said extract; and c) purifying said neutralized and concentrated extract using a chromatographic method, including but not limited to polyamide, LH-20, XAD resin, CG-161 resin, silica gel or reverse phase chromatography. In one embodiment of the invention the extract is purified using a method selected from the group consisting of recrystallization, precipitation, solvent partition and/or chromatographic separation. The present invention provides a commercially viable process for the isolation and purification of chromones having desirable physiological activity.

The preparation of products for administration in pharmaceutical preparations may be performed by a variety of methods well known to those skilled in the art. The chromones may be formulated as an herb powder in the form of their natural existence; as solvent and/or supercritical fluid extracts in different concentrations; as enriched and purified compounds through recrystallization, column separation, solvent partition, precipitation and other means, as a pure and/or a mixture containing substantially purified chromones prepared by synthetic methods.

The inventors have demonstrated using accepted animal models that administration of a chromone or mixtures thereof, such as aloesin and/or aloesinol or extracts comprising mixtures of chromones isolated from a variety of plant sources, for example Aloe ferox leave exudates; together with Aloe vera gel or Aloe vera whole leaf gel powders and extracts reduced insulin resistance, lowered insulin levels simultaneously, maintained low fasting glucose levels and significantly reduced triglyceride levels without impacting food intake and body weight. The novel use of one or more chromones and/or chromone standardized extracts isolated from plants containing these compounds, such as Aloe vera and Aloe ferox and other plant species in ameliorating insulin resistance and lowering fasting blood glucose levels has not been described previously. The disclosed chromones can be used as insulin sensitizers and prophylaxis for prevention and treatment of metabolic disorders, including but not limited to insulin resistance, glucose intolerance, metabolic syndromes, dyslipidemia, hypertriglyceridemia, and hypertriglyceridemia of mammals, including but not limited to humans.

The compositions of this invention can be administered by any method known to one of ordinary skill in the art. The modes of administration include, but are not limited to, enteral (oral) administration, parenteral (intravenous, subcutaneous, and intramuscular) administration and topical application. The method of treatment according to this invention comprises administering internally or topically to a patient in need thereof a therapeutically effective amount of the individual and/or a mixture of chromones isolated from either a single source or multiple sources including, but not limited to synthetically obtained, naturally occurring, or any combination thereof. The purity of the individual and/or a mixture of chromones ranges from 0.01% to 100%, depending on the methodology used to obtain the compound(s). The concentration of the chromone composition in oral, injectable, topical, aerosol suppository, intradermal administrations can be 0.001% to 99.99% by weight of total amount of in an appropriate formulation. Chromones can be used by any routes of administration selected from the group consisting of oral, topical, aerosol, suppository, intradermic, intramusclar, and intravenous administration with a daily dosage in a range of 0.01 mg/kg to 500 mg/kg body weight of mammals, particularly humans.

BRIEF DESCRIPTION OF THE DRAWINGS

FIG. 1 depicts graphically the effect of indomethacin on adiponectin levels secreted into the media using previously published (FIG. 1A) and improved (FIG. 1B) protocols.

(5 mg/kg), Qmatrix® (400 mg/kg), UP780 (100, 200, and 400 mg/kg) and vehicle control. Statistically significant lowered fasting blood glucose levels were found as early as week 2 post treatment, P<0.05 (*)(¥). The data are means±SD, n=7. Animals treated with 200 mg/kg UP780 and GW1929 showed statistically significant lower fasting glucose level on both weeks (week 5 and 7) when compared to untreated vehicle. Mice treated with Qmatrix® and UP780 at 400 mg/kg exhibited similar lower level of fasting blood glucose level at week 5. On the other hand, the 100 mg/kg UP780 treated groups did maintain a relatively high level of fasting blood glucose compared to the untreated vehicle for all the weeks tested, P≤0.05 (*).

Figure 17:
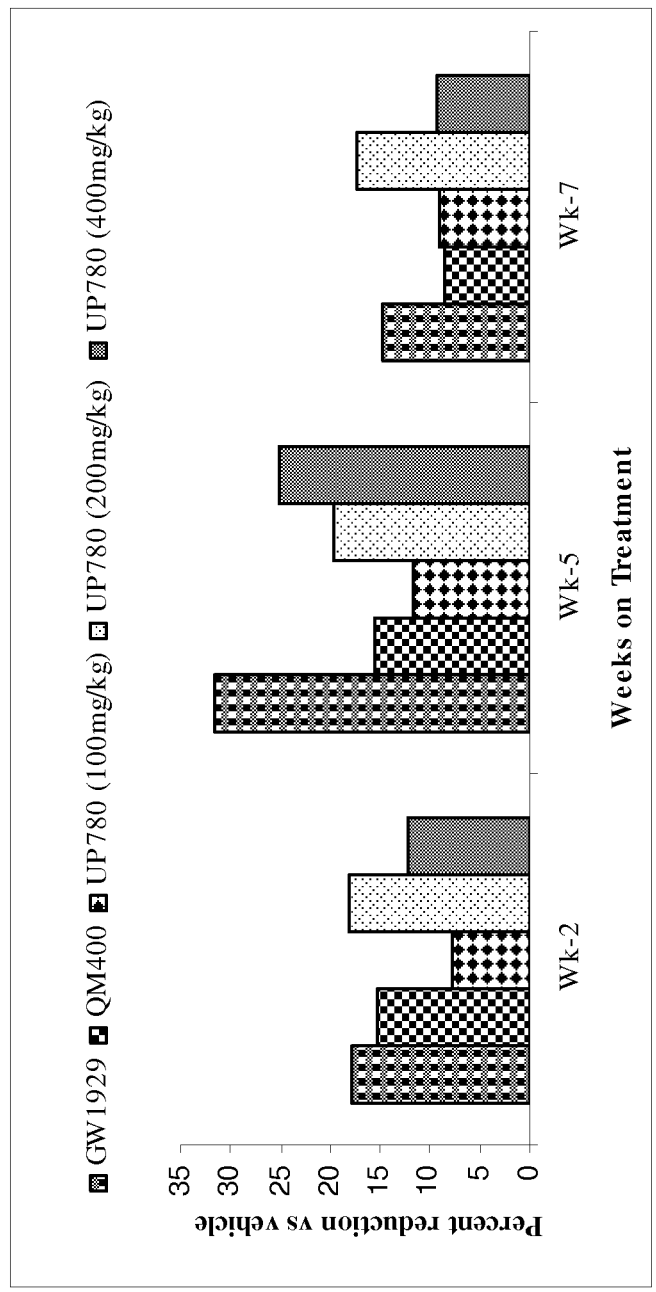

FIG. 17 illustrates graphically the percent reduction in fasting blood glucose levels versus vehicle control as measured at 2, 5, and 7 weeks after treatment onset. Animals were treated with GW1929 (5 mg/kg), Qmatrix® (400 mg/kg), UP780 (100, 200, and 400 mg/kg) and vehicle control. Consistently low levels of fasting blood glucose levels were found for the 200 mg/kg UP780 treatment group as early as week 2. The data are means±SD, n=7. The percent reduction of fasting glucose level, animals treated with 200 mg/kg UP780, were determined and found to be 18%, 20% and 17% for weeks 2, 5, and 7 respectively when compared to vehicle.

Figure 18:
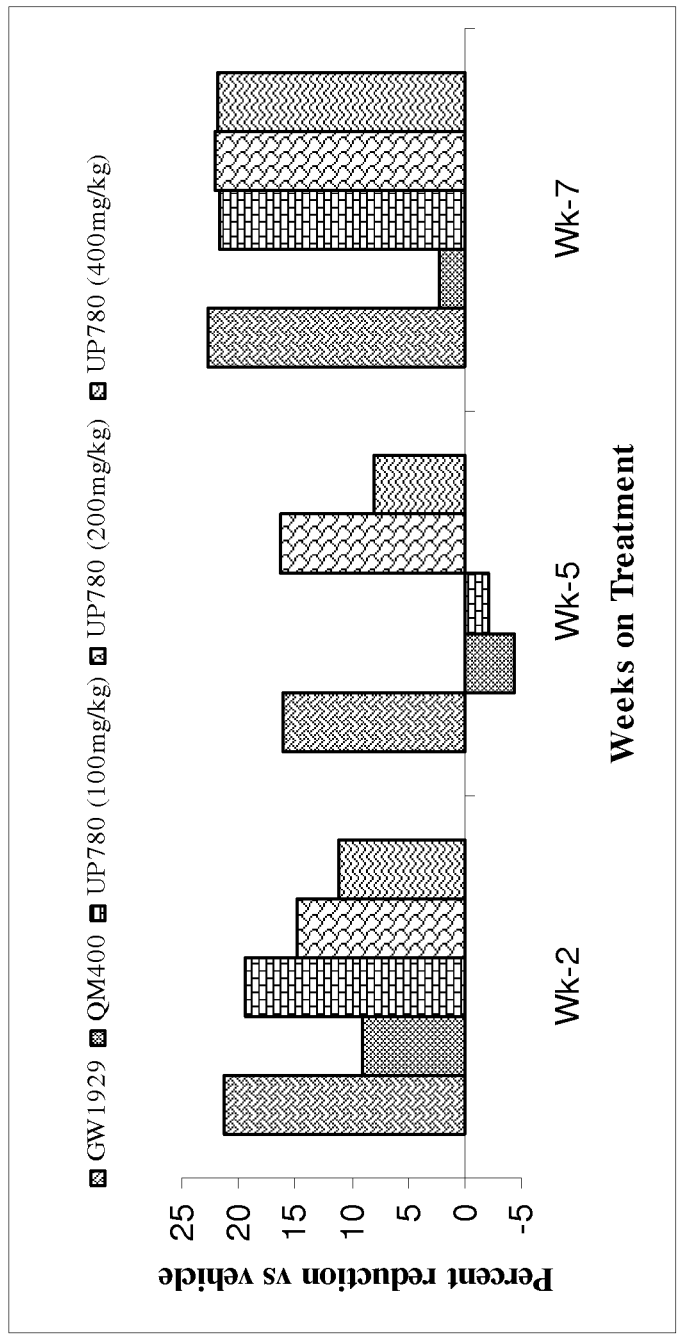

FIG. 18 depicts graphically the effect of GW1929, Qmatrix®, UP780 (100, 200 and 400 mg/kg) and vehicle on fasting triglyceride levels of male C57BL/6J mice. Percent reductions of vehicle control in fasting triglyceride levels were determined at 2, 5, and 7 weeks after treatment onset. Animals were treated with GW1929 (5 mg/kg), Qmatrix® (400 mg/kg), UP780 (100, 200, and 400 mg/kg) and vehicle control. Consistently low levels of fasting triglyceride levels were found for the 200 mg/kg UP780 treatment group as early as week 2. The data are means±SD, n=7. After 7 weeks of daily treatment, percent reduction of fasting triglyceride level to vehicle were 2%, 22.1%, 22%, 21.7%, and 22.7% reduction for 400 mg/kg Qmatrix®, 200, 400 and 100 mg/kg UP780 and GW1929, respectively.

Figure 19:
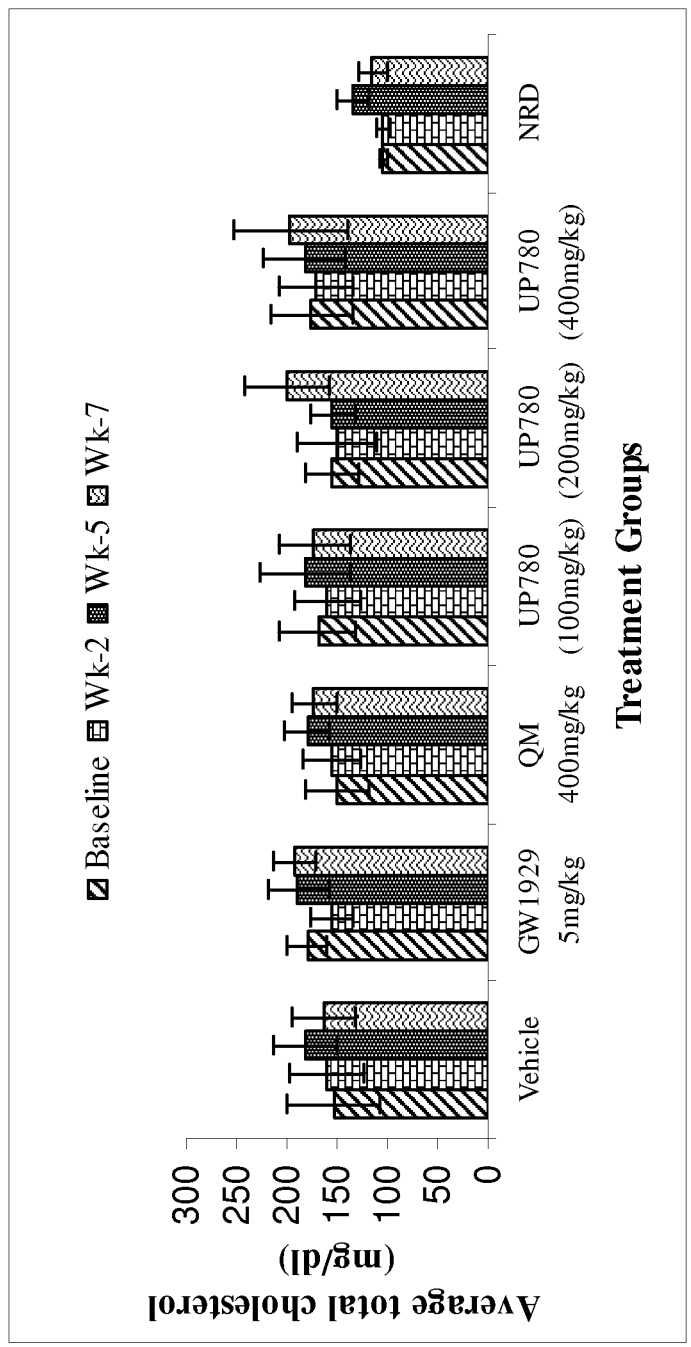

FIG. 19 illustrates graphically the effect of GW1929, Qmatrix®, UP780 (100, 200 and 400 mg/kg) and vehicle on cholesterol levels. Fasting total cholesterol levels were measured at baseline and 2, 5, and 7 weeks after treatment onset by using 15-20 μl blood obtained from tail vein. Animals were treated with GW1929 (5 mg/kg), Qmatrix® (400 mg/kg), UP780 (100, 200, and 400 mg/kg) and vehicle control. No changes in total cholesterol level were observed for all the treatment groups compared to vehicle control. The data are means±SD, n=7. No significant changes in cholesterol levels were noted for all the treatment groups, when compared to vehicle at P≤0.05.

Figure 20:
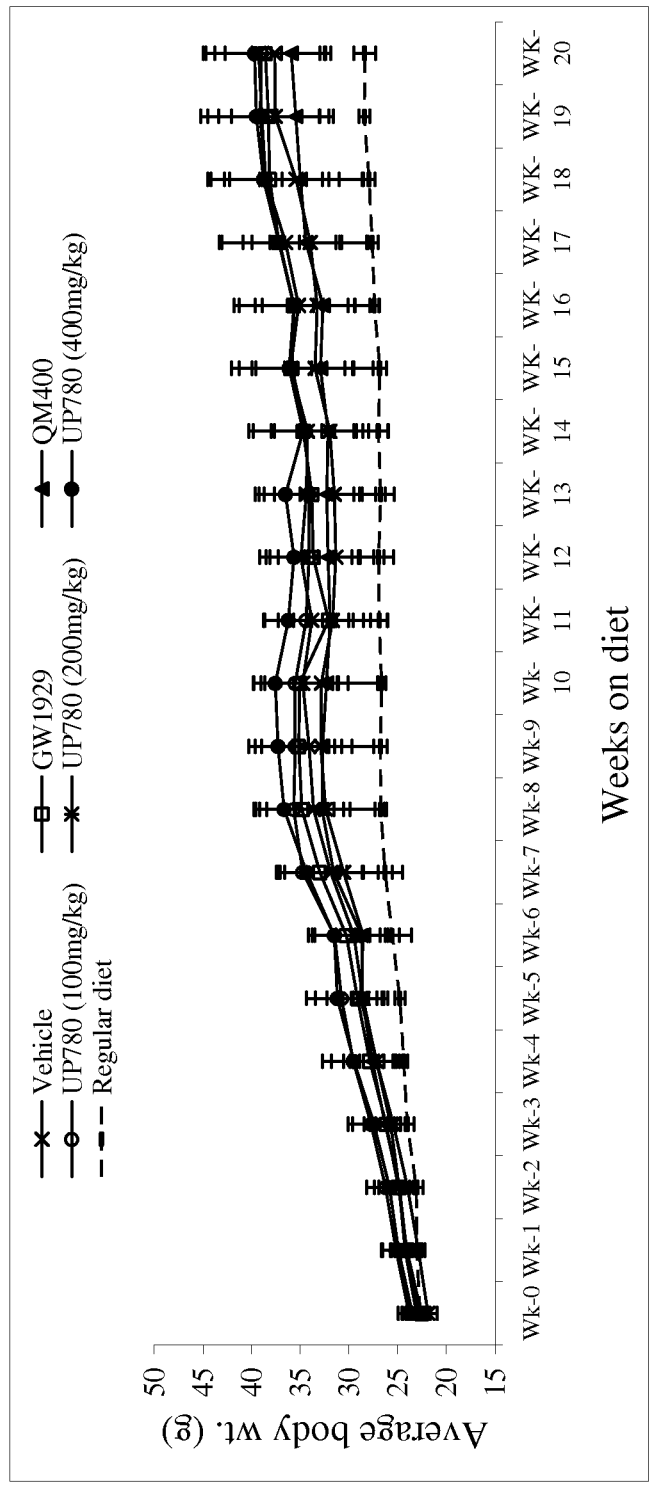

FIG. 20 illustrates the effect of GW1929, Qmatrix®, UP780 (100, 200 and 400 mg/kg) and vehicle on the body weight of male C57BL/6J mice. Three or four male C57BL/6J mice were housed in a mouse cage that had sections for feed and water. Body weight measurement was taken once a week during induction period and treatment weeks. Animals were treated with GW1929 (5 mg/kg), Qmatrix® (400 mg/kg), UP780 (100, 200, and 400 mg/kg) and vehicle control. No statistically significant body weight gain difference between groups was observed for any of the mice treated with GW1929, Qmatrix®, UP780 (100, 200 and 400 mg/kg) and vehicle. The data are means±SD, n=7. As depicted on FIG. 20, animals in each treatment group, including vehicle and normal rodent diet, continued to gain weight throughout the study period. The body weight gain difference noticed between group I (Qmatrix® 400 mg/kg and 200 mg/kg UP780) and group II (GW1929, vehicle, 100, 400 mg/kg UP780) is not statistically significant at P≤0.05.

Figure 21:
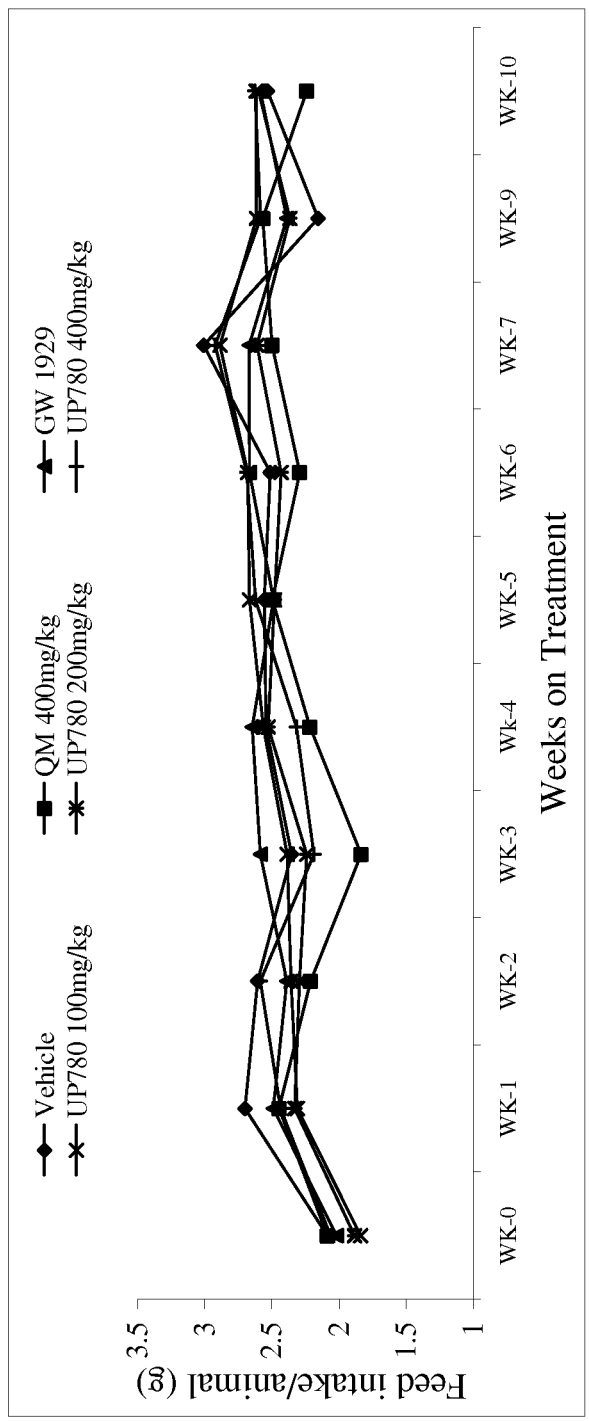

FIG. 21 illustrates the effect of GW1929, Qmatrix®, UP780 (100, 200 and 400 mg/kg) and vehicle on feed consumption of male C57BL/6J mice. Three or four male C57BL/6J mice were housed in a mouse cage that had sections for feed and water. Feed intake measurement was taken once a week during induction period and treatment weeks. Treatment weeks feed consumption data are shown. Animals were treated with GW1929 (5 mg/kg), Qmatrix® (400 mg/kg), UP780 (100, 200, and 400 mg/kg) and vehicle control. No statistically significant difference in feed intake between groups. The data are means±SD, n=7. In agreement with the body weight data, similar pattern of feed consumptions were recorded for all the groups.

Figure 22A:
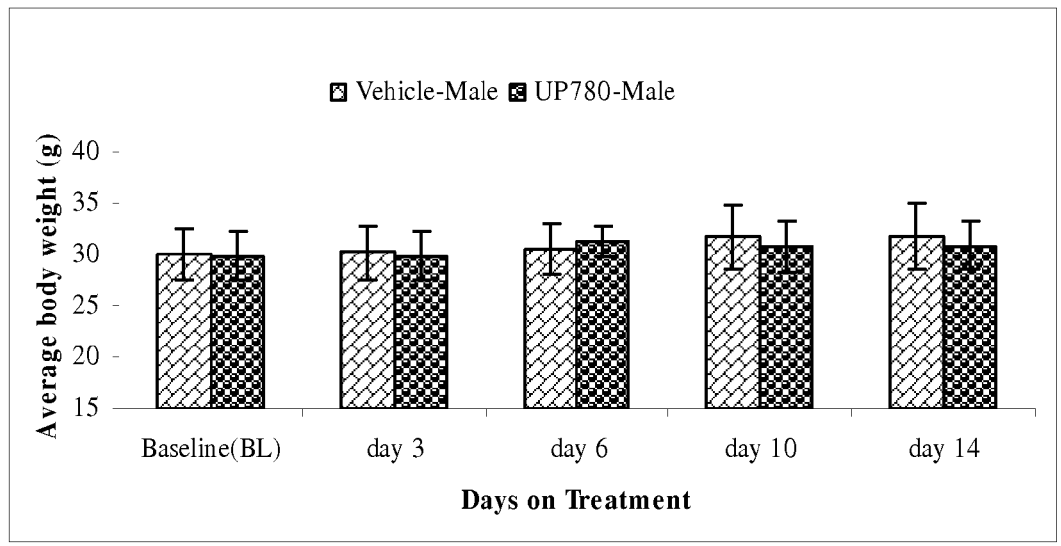
Figure 22B:
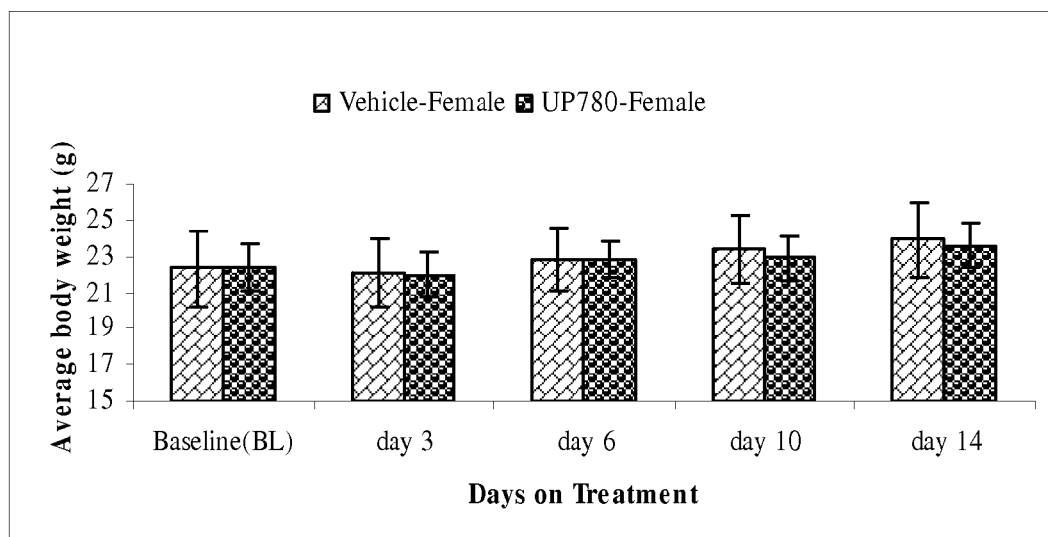

FIGS. 22A and B depict the results of an acute toxicity study measuring average body weight of males (FIG. 22A) and females (FIG. 22B). The rate of weight gain between control and treatment groups was consistent throughout the study. Mice were treated with 2 g/kg of UP780 and vehicle control for 14 days. Statistical analysis of body weight gain difference between necropsy day and baseline for UP780 treated animals and vehicle control showed that there was no significant difference in weight gain both for males and females. Similarly, there was no statistically significance in mean body weight gain for both males and females of UP780 treated animals and vehicle control animals at each data points compared. The data are means±SD, n=5.

Figures 23A, 23B:
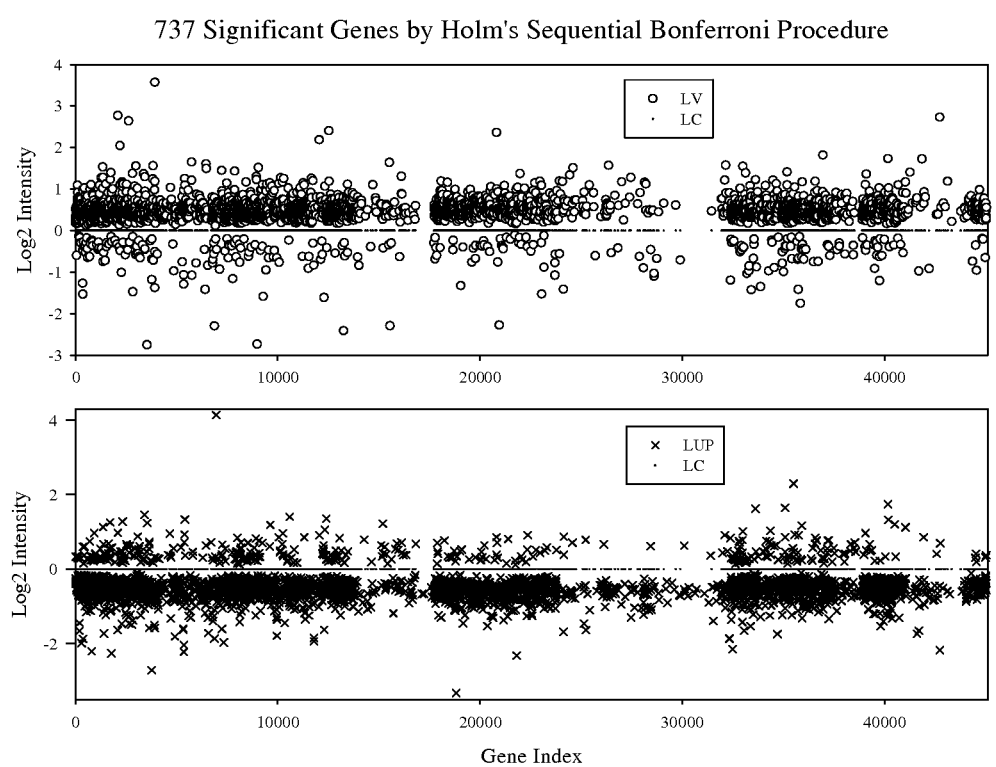

FIG. 23 illustrates graphically from a visual perspective the general up-regulation of gene expression of LV vs. LC (FIG. 23A) and down-regulation of gene expression of LUP vs. LC (FIG. 23B). The graphs are generated by the software SigmaPlot. ANOVA is used on the normalized microarray data to detect differentially expressed genes between treatment groups (LV vs. LC and LUP vs. LC). For each comparison, the significant differentially expressed genes are obtained from the results of the ANOVA models and multiple comparison corrections. The number of statistically significant probe sets for the comparison via Holm's sequential Bonferroni procedure are summarized in graphs, LV vs. LC (FIG. 23A) and LUP vs. LC (FIG. 23B).

Figure 24A:
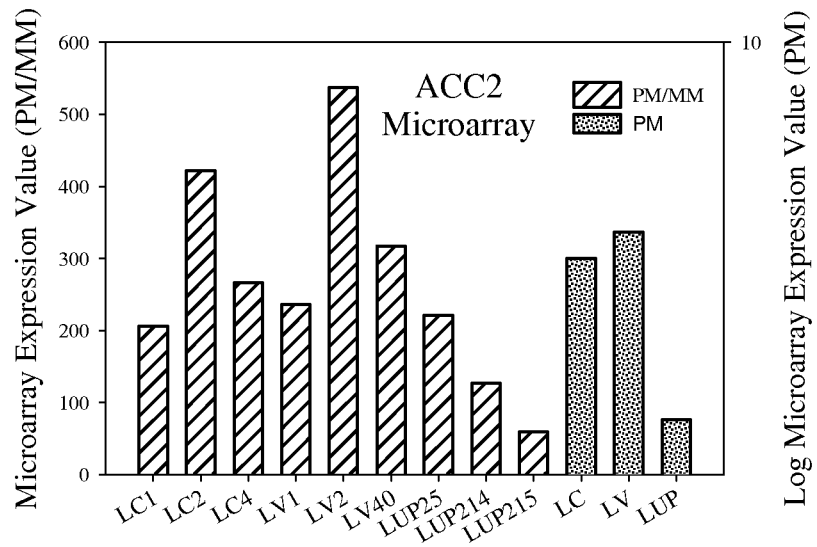
Figure 24B:
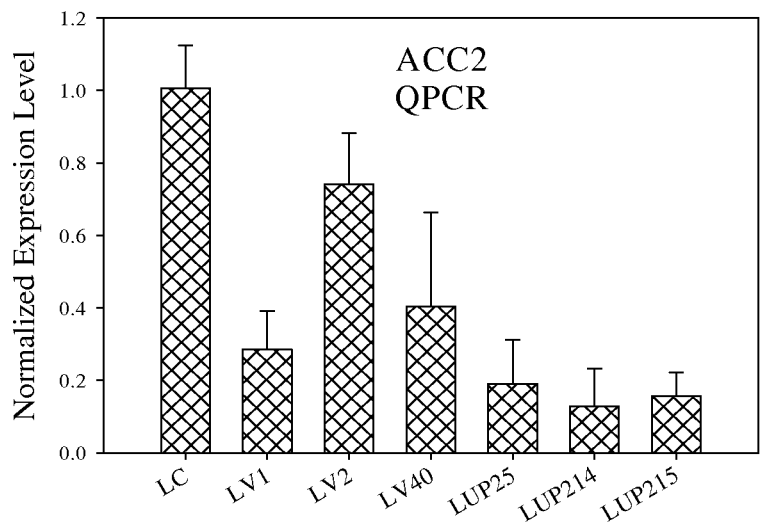

FIG. 24 depicts the QPCR validation of microarray analysis for ACC2 transcript levels. FIG. 24A, quantification from the microarray data. FIG. 24B, QPCR quantification, plotted as normalized expression level according to the expression level of GAPDH. The three lean control RNA samples were pooled as LC for QPCR; the high-fat-diet (LV) and the high-fat-diet+UP780 (LUP) treatment RNA samples were used individually for QPCR. The same RNA preparations were used both for microarray and for QPCR. Since PM+MM and PM-only intensity values were used independently for microarray data analysis (see Example 20), both were plotted for comparison, and where available, for comparison of animal to animal variations.

Figure 25A:
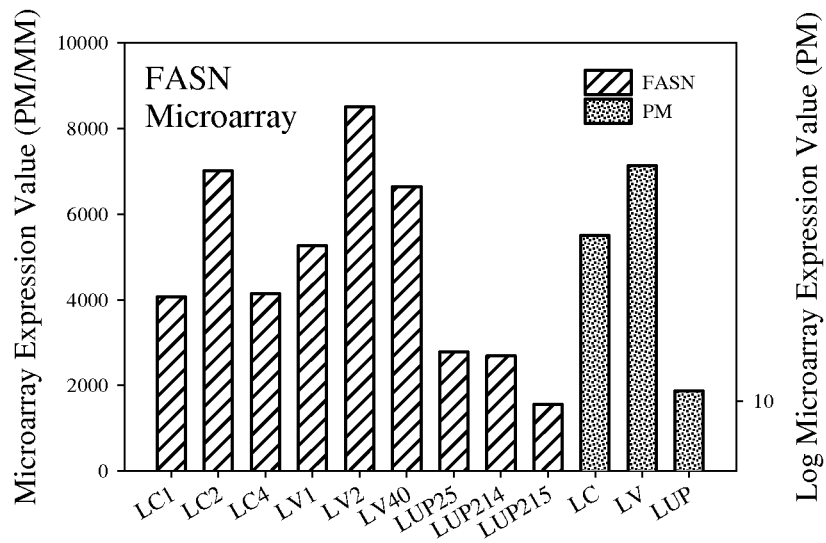

FIGS. 25A and B depict the QPCR validation of microarray analysis for FASN transcript levels, in the same format as described in FIG. 24.

Figure 26A:
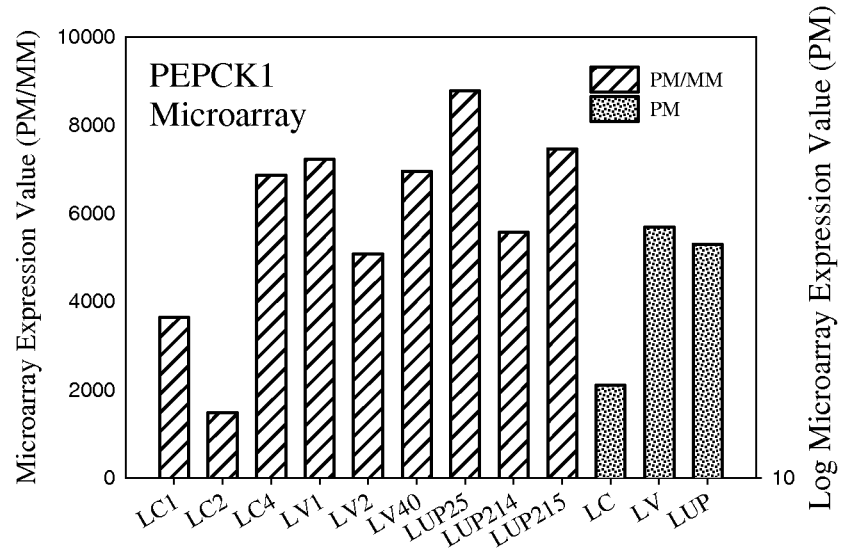

FIGS. 26A and B depict the QPCR validation of microarray analysis for PEPCK1 transcript levels, in the same format as described in FIG. 24.

Figure 27A:
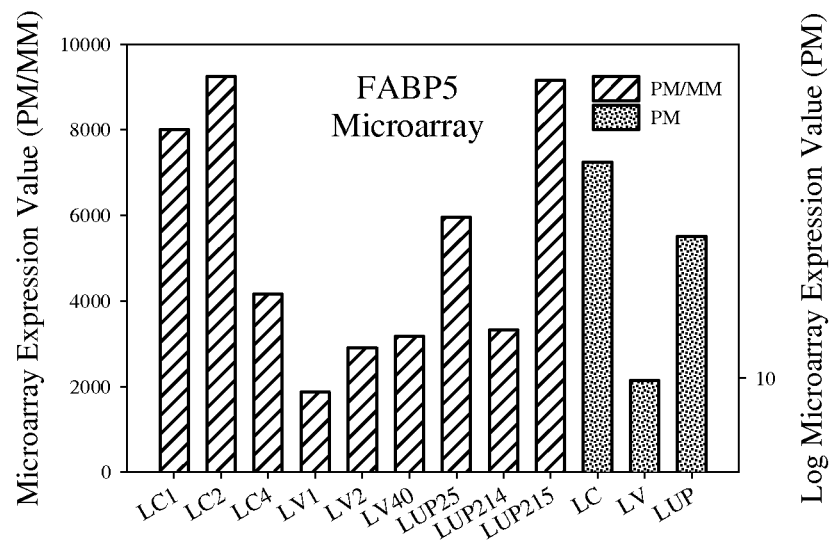

FIGS. 27A and B depict the QPCR validation of microarray analysis for FABP5 transcript levels, in the same format as described in FIG. 24.

Figure 28A:
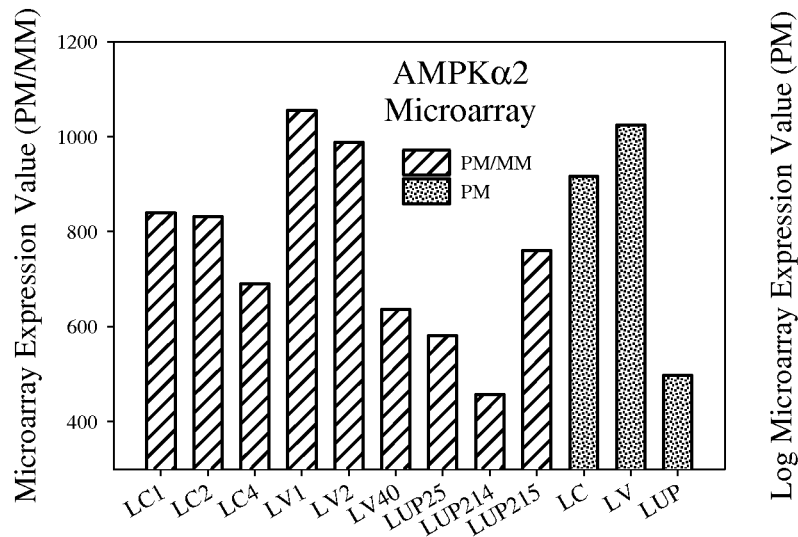

FIGS. 28A and B depict the QPCR validation of microarray analysis for AMPKα2 transcript levels, in the same format as described in FIG. 24.

DETAILED DESCRIPTION OF THE PREFERRED EMBODIMENT

The present invention describes the identification and isolation of chromones and novel chromone compositions from plant sources that exhibit up-regulation of adiponectin production by adipocytes and the normalization of virtually hundreds of genes related to glucose and fatty acid metabolic and signaling pathways. The chromone compositions are effective in enhancing adiponectin production by adipocytes and regulating genes involved in fatty acid biosynthesis, mitochondrial β-oxidation of fatty acids, steroid biosynthesis, gluconeogenesis, fat transport, PPARα/RXRα liver signaling and xenobiotic metabolism. The chromone compositions can be used to increase insulin sensitivity, improve glucose tolerance, lower triglyceride levels and balance glucose levels in mammals. Included in the present invention are methods for the prevention and treatment of a variety of diseases and conditions including, but not limited to insulin resistance, glucose intolerance, hyperglycemia, metabolic syndromes, dyslipidemia, and hypertriglyceridemia.

Also included in the present invention are novel compositions comprised of a mixture of one or more chromones and either *Aloe* gel powder or *Aloe* whole leaf gel powder. These novel compositions are extremely effective at lowering glucose levels and enhancing insulin sensitivity. The compositions are prepared by mixing aloe gel powder or whole leaf aloe gel powder with a substantially pure mixture of one or more chromones, wherein said mixture of one or chromones is essentially free of anthraquinones (typically Aloin A and B). By "substantially pure" it is meant that the mixture of chromones is at least 70% (by weight) pure, preferably at least 80% pure and most preferably 90% or greater pure. By "essentially free of anthraquinones" it is meant that the total amount of anthraquinones in the mixture of chromones is less than or equal to 100 ppm, more preferably less than or equal to 50 ppm. The aloe gel powder or whole leaf gel powder (referred to herein collectively as "*Aloe* gel") can be prepared by any known standard method of preparing these compositions. In one embodiment, the *Aloe* gel is prepared from either *Aloe barbadensis* or *Aloe vera*. The ratio of *Aloe* gel to total chromones in these compositions can be in the range of 0.1-99.9%. In some embodiments, the compositions are comprised of 90% to 99% (by weight) *Aloe* gel and 1 to 10% (by weight) total chromones. In other embodiments, the compositions are comprised of 95 to 99% (by weight) *Aloe* gel and 1-5% (by weight) total chromones. In yet other embodiments, the compositions are comprised of 98 to 99% (by weight) *Aloe* gel and 1-2% (by weight) total chromones. The chromones are isolated as described in detail below. In some embodiments, the one or more chromone is selected from the group consisting of aloesin, aloesinol, aloeresin A, aloeresin C, aloeresin D, aloeresin E, aloeresin F, and aloesin derivatives. The chromones of the instant invention can be semi-synthesized by chemically changing the structures of naturally occurring chromones or can be completely synthesized from small aromatic stating materials.

Various terms are used herein to refer to aspects of the present invention. To aid in the clarification of the description of the components of this invention, the following definitions are provided.

Unless defined otherwise all technical and scientific terms used herein have the meaning commonly understood by one of ordinary skill in the art to which this invention belongs.

It is to be noted that as used herein the term "a" or "an" entity refers to one or more of that entity; for example, a chromone refers to one or more chromones. As such, the terms "a" or "an", "one or more" and "at least one" are used interchangeably herein.

"Chromones" are a specific class of natural products having a benzopyran-4-one as the major structural skeleton as illustrated by the following general structure:

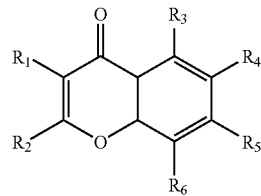

wherein
$R_1$, $R_2$, $R_3$, $R_4$, $R_5$ and $R_6$ are independently selected from the group consisting of —H, —OH, —CH$_3$, —SH, alkyl, alkenyl, oxoalkyl, oxoalkenyl, hydroxylalkyl, hydroxylalkenyl, —OCH$_3$, —SCH$_3$, —OR, —SR, —NH$_2$, —NRH, —NR$_2$, —NR$_3^+$X$^-$, an ester selected from the group, including but not limited to gallate, acetate, cinnamoyl and hydroxyl-cinnamoyl esters, trihydroxybenzoyl esters and caffeoyl esters; and a hexose or pentose, wherein said hexose or pentose is linked to the chromone by a carbon, nitrogen sulfur or oxygen and wherein said hexose or pentose is selected from the group including but not limited to aldopentoses, methyl aldopentose, aldohexoses, ketohexose and chemical derivatives thereof; including a dimer, trimer and other polymerized chromones;

wherein said alkyl and/or alkenyl group is a straight and/or branched chain having between 1-20 carbon atoms with and/or without double bonds and substitution group(s) selected from the group consisting —OH, =O and —OR in different positions;

X is selected from the group of pharmaceutically acceptable counter anions including but not limited to hydroxyl, chloride, iodide, sulfate, phosphate, acetate, fluoride, carbonate; and R is an alkyl group having between 1-20 carbon atoms and a pharmaceutically acceptable carrier.

In one embodiment the chromone(s) is a benzopyran-4-one (7-hydroxy chromone) selected from the group compounds having the following general structure:

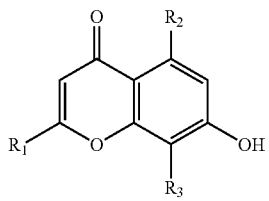

wherein $R_1$, $R_2$, and $R_3$ are as defined above. In another embodiment of this invention the chromone is selected from aloesin or aloesinol.

The chromones of this invention may be obtained by synthetic methods or may be isolated from the genera of numerous plant families, including but not limited to *Acacia, Adina, Aloe, Alternaria, Amoora, Antidesma, Artemisia, Baeckea, Cassia, Clusea, Cnidium, Convolvulus, Epimedium, Eriosema, Eriostemon, Eugenia, Garcinia, Hypericum, Lindenbergia, Pancratium, Penicillium, Polygonum, Ptaeroxylon,*

*Rheum, Sophora, Stephanitis, Syzygium, Talaromyces* and *Zonaria*. In preferred embodiments, the plant is selected from the group, including but not limited to, *Acacia catechu, Acacia concinna, Aloe arborescens, Aloe barbadensis, Aloe cremnophila, Aloe ferox, Aloe saponaria, Aloe vera, Aloe vera* var. *chinensis, Antidesma membranaceum, Artemisia capillaries, Baeckea, frutescens, Epimedium sagittatum, Garcinia dulcis, Hypericum japonicum, Polygonum cuspidatum, Sophora tomentosa* and *Stephanitis rhododendri*. In one embodiment the chromones are isolated from the whole leaves of *Aloe ferox, Aloe vera*, or *Aloe barbadensis*.

The chromones can be found in various parts of the plant, including but not limited to stems, stem barks, trunks, trunk barks, twigs, tubers, roots, root barks, young shoots, seeds, rhizomes, flowers and other reproductive organs, leaves and other aerial parts.

The term "*Aloe*" refers to the genus of South African plants of the Liliaceae family of which the *Aloe veral Aloe barbadensis* (note that *Aloe barbadensis* is the Latin name for the species *Aloe vera*) or *Aloe ferox* are species. *Aloe* chromones are present primarily in the rinds of the leaf of a number of different species of *Aloe*.

The term "*Aloe* extract" is defined as the dried juice of the whole leaf of various species of the *Aloe* plant. The "*Aloe* extract" used in the examples of this invention includes but not limited to fresh and concentrated aloe gel, whole leaf gel, leaf exudates and extracts, which was prepared by "whole-leaf processing" of the whole leaf of various *Aloe* species. In one example, whole leaves obtained from the *Aloe barbadensis* plant were ground, filtered, treated with cellulase (optional) and activated carbon and lyophilized. The lyophilized powder was reconstituted with the chromatography solvent prior to use. In another example, the exudate from *Aloe ferox* leaves was suspended in water, followed by contact with an appropriate chromatography solvent prior to use.

"Therapeutic" as used herein, includes treatment and/or prophylaxis. When used, therapeutic refers to humans, as well as, other for mammalian animals.

"Pharmaceutically or therapeutically effective dose or amount" refers to a dosage level sufficient to induce a desired biological result. That result may be the alleviation of the signs, symptoms or causes of a disease or any other alteration of a biological system that is desired. The precise dosage will vary according to a variety of factors, including but not limited to the age and size of the subject, the disease and the treatment being effected.

A "host" or "patient" or "subject" is a living mammal, human or animal, for whom therapy is desired. The "host," "patient" or "subject" generally refers to the recipient of the therapy to be practiced according to the method of the invention. It should be noted that the invention described herein may be used for veterinary as well as human applications and that the term "host" should not be construed in a limiting manner. In the case of veterinary applications, the dosage ranges can be determined as described below, taking into account the body weight of the animal.

As used herein a "pharmaceutically acceptable carrier" refers to any carrier, which does not interfere with effectiveness of the biological activity of the active ingredient and which is not toxic to the host to which it is administered. Examples of "pharmaceutically acceptable carriers" include, but are not limited to, any of the standard pharmaceutical carriers such as a saline solution, i.e. Ringer's solution, a buffered saline solution, water, a dextrose solution, serum albumin, and other excipients and preservatives for tableting and capsulating formulations.

Note, that throughout this application various citations are provided. Each citation is specifically incorporated herein in its entirety by reference.

The present invention includes methods for the prevention and treatment of metabolic syndrome and diseases and conditions mediated by insulin resistance in mammals. The method is comprised of administering to a subject in need thereof an effective amount of a pharmaceutical or a nutraceutical composition comprising one or more chromones. The chromone or mixture of chromones may be isolated from a single source or multiple sources, including but not limited to, synthetically obtained, naturally occurring, or any combination thereof.

In one embodiment the present invention describes a method for increasing adiponectin production from adipocytes comprising administering to a subject in need thereof an effective amount of a chromone or a mixture of chromones; wherein said chromone or a mixture of chromones. In another embodiment, the present invention describes a method for normalizing high fat diet induced changes of gene expressions of fatty acid biosynthesis, mitochondria β-oxidation of fatty acids, steroid biosynthesis, gluconeogenesis, fat transport, PPARα/RXRα liver signaling and xenobiotic metabolism, said method comprising administrating to a subject in need thereof an effective amount of a composition comprising a chromone or a mixture of chromones. In yet another embodiment the present invention includes a method for preventing and treating insulin resistance, glucose intolerance, hyperglycemia, metabolic syndromes, dyslipidemia, and hypertriglyceridemia, said method comprising administrating to a subject in need thereof an effective amount of a composition comprising a chromone or a mixture of chromones.

The chromones that can be used in accordance with the following include compounds illustrated by the following general structure:

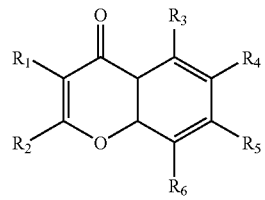

wherein
$R_1, R_2, R_3, R_4, R_5$ and $R_6$ are independently selected from the group consisting of —H, —OH, —$CH_3$, —SH, alkyl, alkenyl, oxoalkyl, oxoalkenyl, hydroxylalkyl, hydroxylalkenyl, —$OCH_3$, —$SCH_3$, —OR, —SR, —$NH_2$, —NRH, —$NR_2$, —$NR_3^+X^-$, an ester selected from the group, including but not limited to gallate, acetate, cinnamoyl and hydroxyl-cinnamoyl esters, trihydroxybenzoyl esters and caffeoyl esters; and a hexose or pentose, wherein said hexose or pentose is linked to the chromone by a carbon, nitrogen sulfur or oxygen and wherein said hexose or pentose is selected from the group including but not limited to aldopentoses, methyl aldopentose, aldohexoses, ketohexose and chemical derivatives thereof; including a dimer, trimer and other polymerized chromones;

wherein said alkyl and/or alkenyl group is a straight and/or branched chain having between 1-20 carbon atoms with and/or without double bonds and substitution group(s) selected from the group consisting —OH, =O and —OR in different positions;

X is selected from the group of pharmaceutically acceptable counter anions including but not limited to hydroxyl, chloride, iodide, sulfate, phosphate, acetate, fluoride, carbonate; and R is an alkyl group having between 1-20 carbon atoms and a pharmaceutically acceptable carrier.

In one embodiment the chromone(s) is a benzopyran-4-one (7-hydroxy chromone) selected from the group compounds having the following general structure:

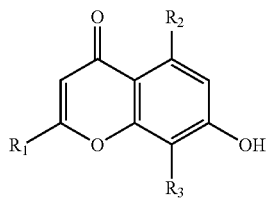

wherein $R_1$, $R_2$, and $R_3$ are as defined above. In another embodiment of this invention the chromone is selected from aloesin and/or aloesinol whose structures are depicted below.

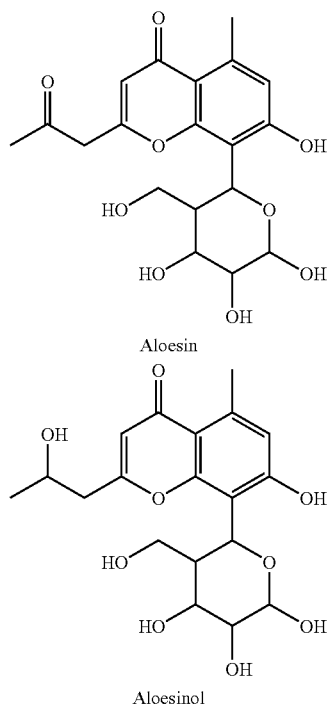

Aloesin

Aloesinol

The chromones of this invention may be obtained by synthetic methods or may be isolated from the genera of numerous plant families, including but not limited to *Acacia, Adina, Aloe, Alternaria, Amoora, Antidesma, Artemisia, Baeckea, Cassia, Clusea, Cnidium, Convolvulus, Epimedium, Eriosema, Eriostemon, Eugenia, Garcinia, Hypericum, Lindenbergia, Pancratium, Penicillium, Polygonum, Ptaeroxylon, Rheum, Sophora, Stephanitis, Syzygium, Talaromyces* and *Zonaria*. In preferred embodiments, the plant is selected from the group, including but not limited to, *Acacia catechu, Acacia concinna, Aloe arborescens, Aloe barbadensis, Aloe cremnophila, Aloe ferox, Aloe saponaria, Aloe vera, Aloe vera* var. *chinensis, Antidesma membranaceum, Artemisia capillaries, Baeckea, frutescens, Epimedium sagittatum, Garcinia dulcis, Hypericum japonicum, Polygonum cuspidatum, Sophora tomentosa* and *Stephanitis rhododendri*. In one embodiment the chromones are isolated from the whole leaves of *Aloe ferox, Aloe vera*, or *Aloe barbadensis*.

The chromones can be found in various parts of the plant, including but not limited to stems, stem barks, trunks, trunk barks, twigs, tubers, roots, root barks, young shoots, seeds, rhizomes, flowers and other reproductive organs, leaves and other aerial parts.

The chromone compounds and compositions of the instant invention, as well as their biochemical and biological activity were identified from a random screening of 2059 plant extracts as described below. The primary screening was designed based on the ability of plant extracts or compounds to enhance adiponectin production from cultured adipocytes. The adipocytes were differentiated from mouse fibroblasts (3T3 L1). It was believed that measurement of a key adipokin marker protein—adiponectin level in the adipocyte culture media, would enable the identification of naturally occurring compounds that would act as PPAR pan regulators, or would modulate other glucose and fatty acid key metabolic pathways for use in the prevention and treatment metabolic disorders including, but not limited to insulin resistance, glucose intolerance, hyperglycemia, metabolic syndromes, dyslipidemia, and hypertriglyceridemia of mammals, particularly humans.

To create a plant extract library, dried plant materials were ground to fine powders and extracted with methanol:dichloromethane (1:1) using an ASE 300 automatic extractor as described in Example 1. The extracts were dried by rotary evaporation and a speed-vacuum. Each plant extract (approximately 75 mg) was dissolved in 1.5 ml DMSO (1.5 ml) to make a solution with a concentration of 50 mg/ml.

Figure 1A:
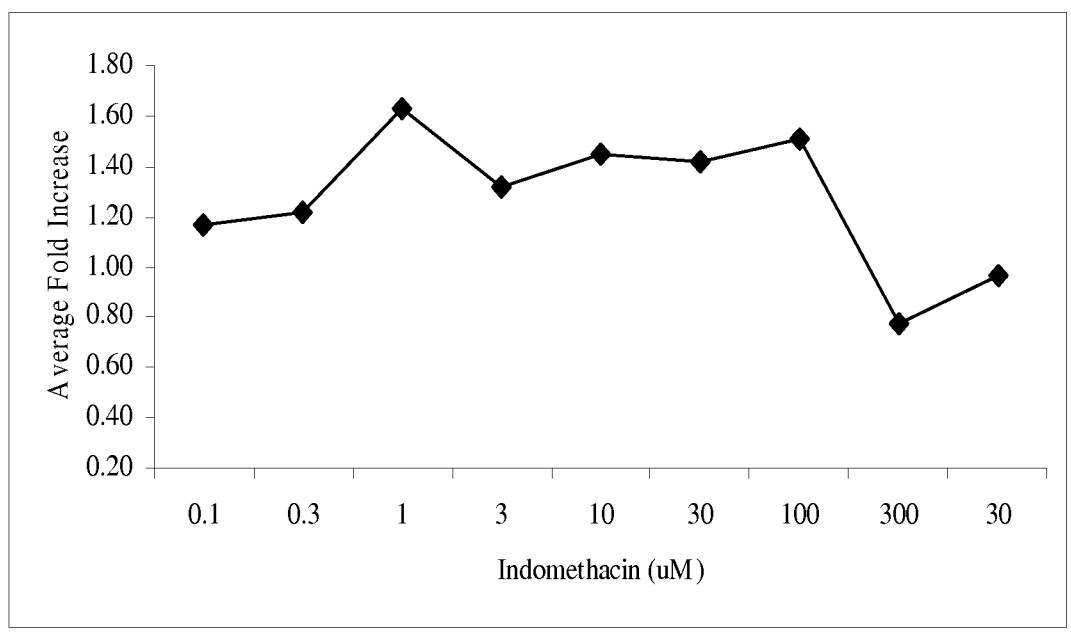
FIG. 1A. 3T3-L1 cells were induced to differentiate for 7 days and treated with indomethacin for 24 hours. The highest average fold increase in adiponectin level was 1.6-fold by indomethacin at 1 µM.
Figure 1B:
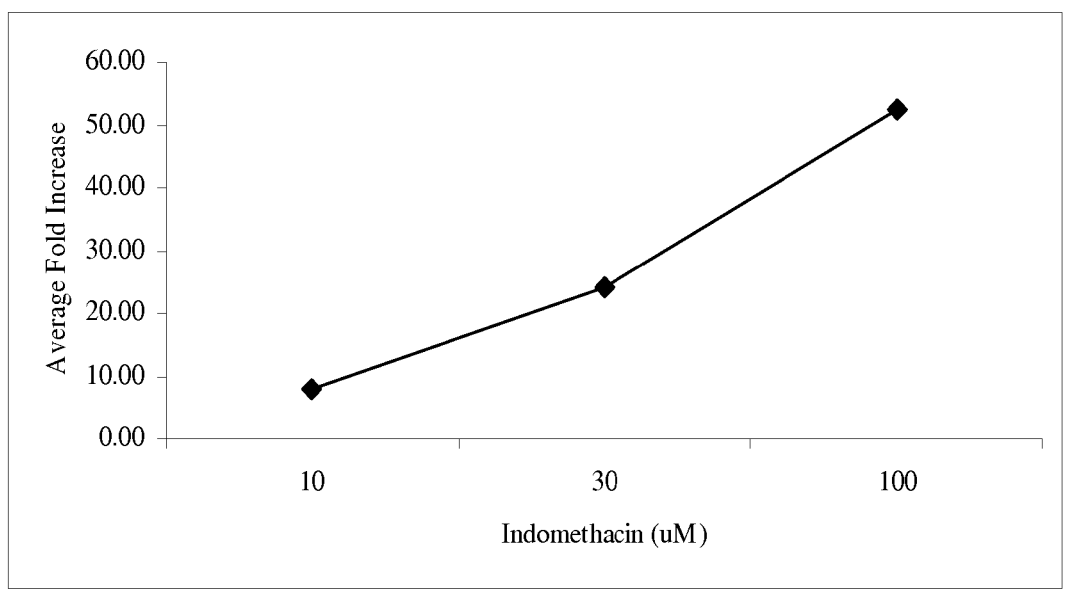
FIG. 1B. 3T3-L1 cells were induced to differentiate for 2 days and treated with indomethacin for 2 days. The highest average fold increase in adiponectin level was 52-fold by indomethacin at 100 µM, while the lowest fold increase was 7-fold at 10 µM.

3T3-L1 cells have been shown to produce and secret adiponectin into media in response to PPARγ activators. However, only a two-fold increase in adiponectin secretion was achieved in response to treatment of PPARγ activators in the literature. When this experiment was repeated, the best signal to background ratio of the assay achieved was 1.6 with indomethacin at concentrations between 0.1-300 μM under the published experimental conditions (FIG. 1A). We improved the signal to noise ratio dramatically by changing the induction and cultural conditions as shown in Examples 2 and 3. 3T3-L1 cells were induced to differentiate for 2 days and then treated with indomethacin for 2 days. The highest average fold increase of adiponectin was 52 folds with 100 μM of indomethacin (FIG. 1B). This assay system was used to screen the 2059 organic extracts.

Figure 2:
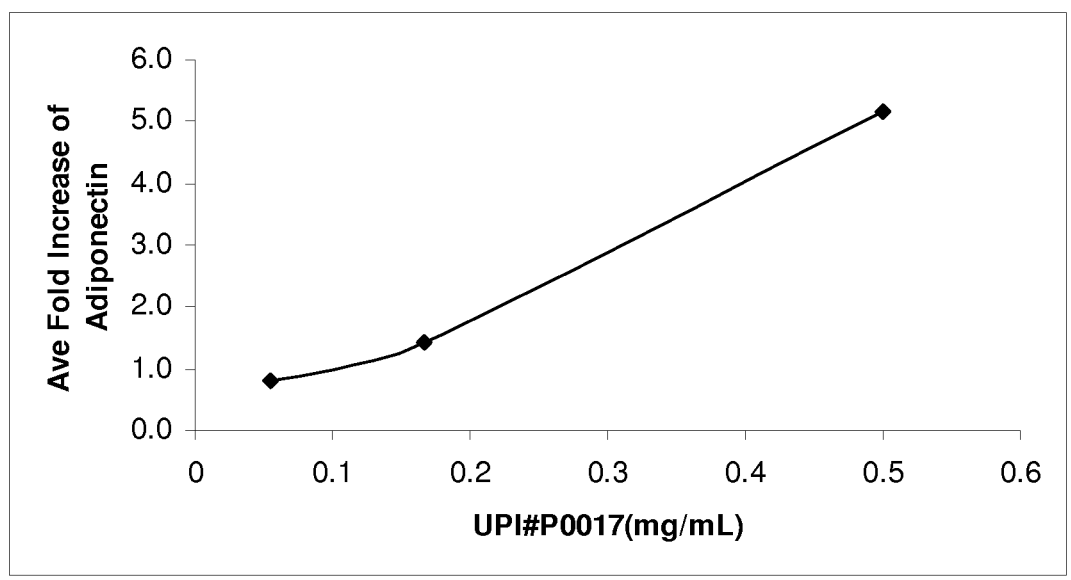
FIG. 2 illustrates graphically the effect of Aloe ferox plant extract (P0017-OE) on adiponectin levels secreted into the media of differentiated 3T3-L1 cells. Briefly, 3T3-L1 cells were induced to differentiate then treated with the crude organic extract P0017-OE at concentrations of 0.5, 0.166 and 0.055 mg/ml for 48 hours. The original crude extract was diluted 1:3 then 1:9 to test dose-response.

The initial screening yielded 139 positive hits using a cut-off threshold value of adiponectin induction that were equivalent to that conferred by a reference compound indomethacin at 10 μM. As a result of the subsequent verification assays and secondary screening, one active extract from leave exudates of *Aloe ferox*, designated as P0017, showed a consistent up modulating adiponectin level in the media (FIG. 2).

Figure 3:
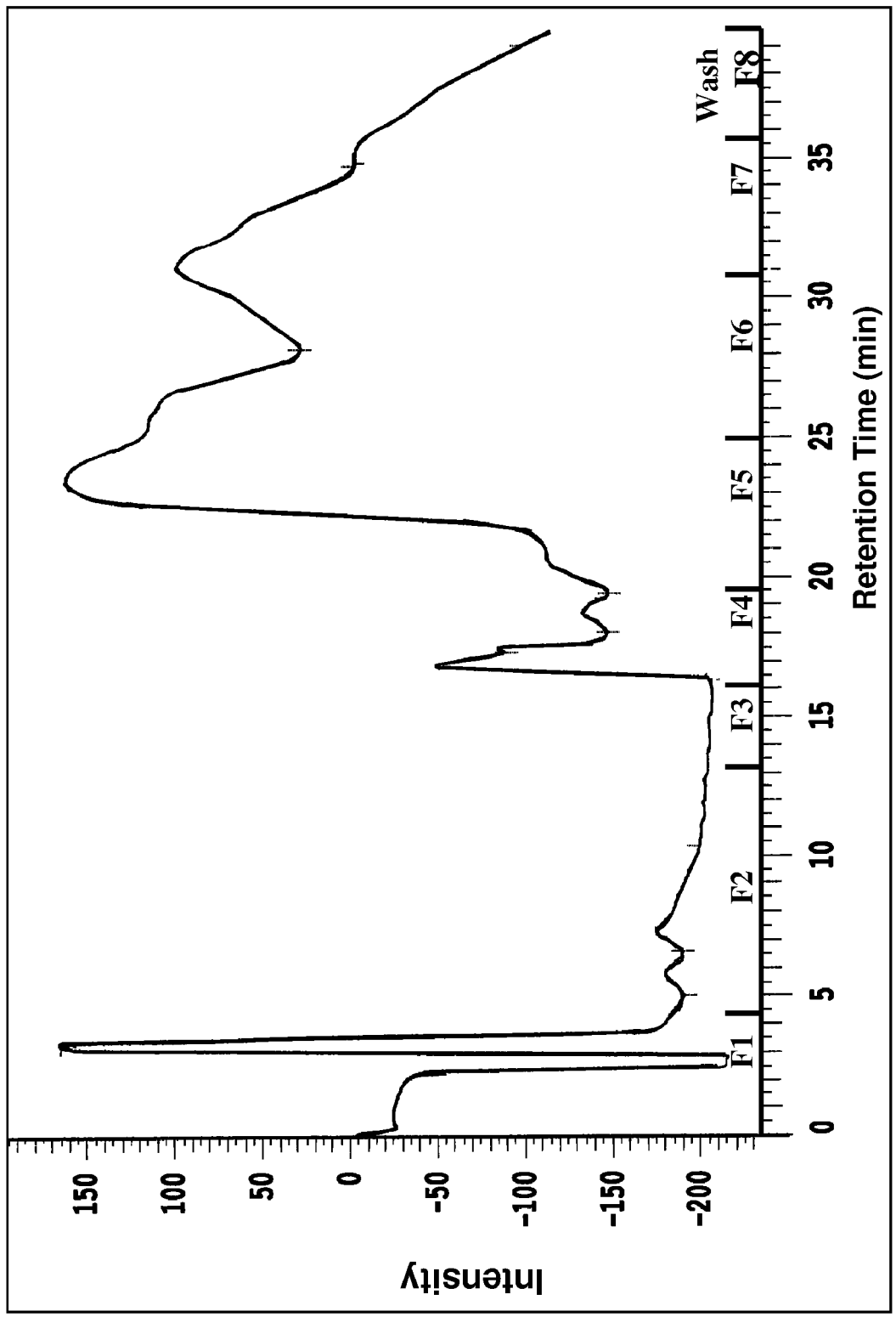
FIG. 3 depicts the HTP-UV profile and fraction combination of P0017-OE. All 96 fractions were combined into 8 sub-fractions. P0017-OE-NP-F3 was the most active of the 8 sub-fractions in the adiponectin assay.

This active plant extract (P0017-OE) was subsequently subjected to an activity-guided HTP fractionation and compound purification. As shown in Example 5, an organic extract of P0017 was fractioned using a normal phase flash column. Fractions with similar UV absorption and retention times were combined into sub-fractions and dried under low vacuum and centrifugation and named as P0017-OE-HTPF1-8 (FIG. 3). DMSO was used to dissolve each sub-fraction (50 μg/μl) and a portion (2 μl) was used in the adiponectin assay. P0017-OE-HTPF3 showed the greatest activity among the 8 sub-fractions in the bioassay. Repeated large scale extraction and isolation of active fractions and compounds are illustrated in Example 7 and FIG. 4. Bioactive fractions were identified as P0017-AC1 and P0017-AC2.

Figure 6:
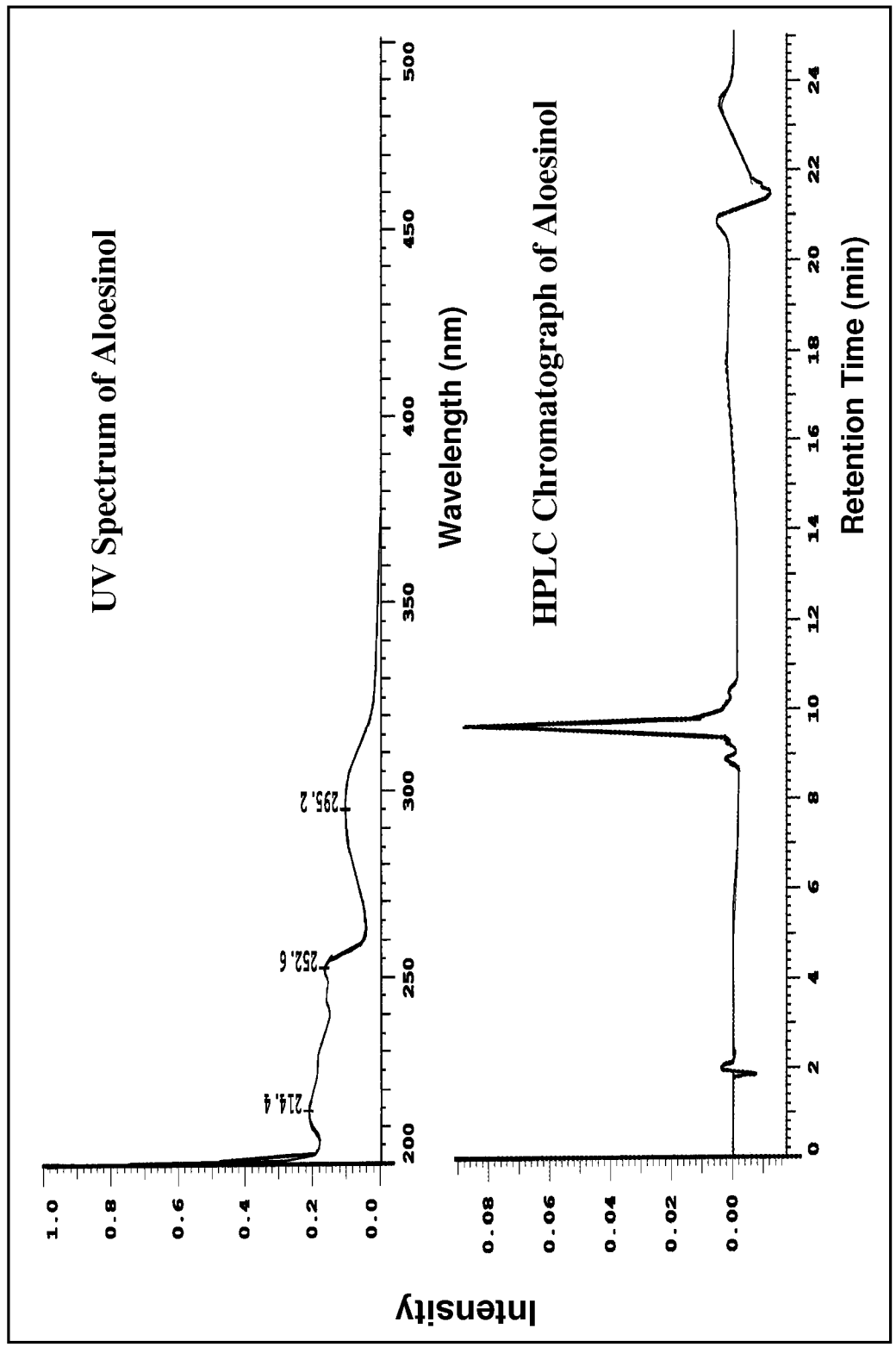
FIG. 6 depicts the identification of aloesinol (UP396) via UV spectra elucidation and HPLC retention time comparison with authentic standard.
Figure 7:
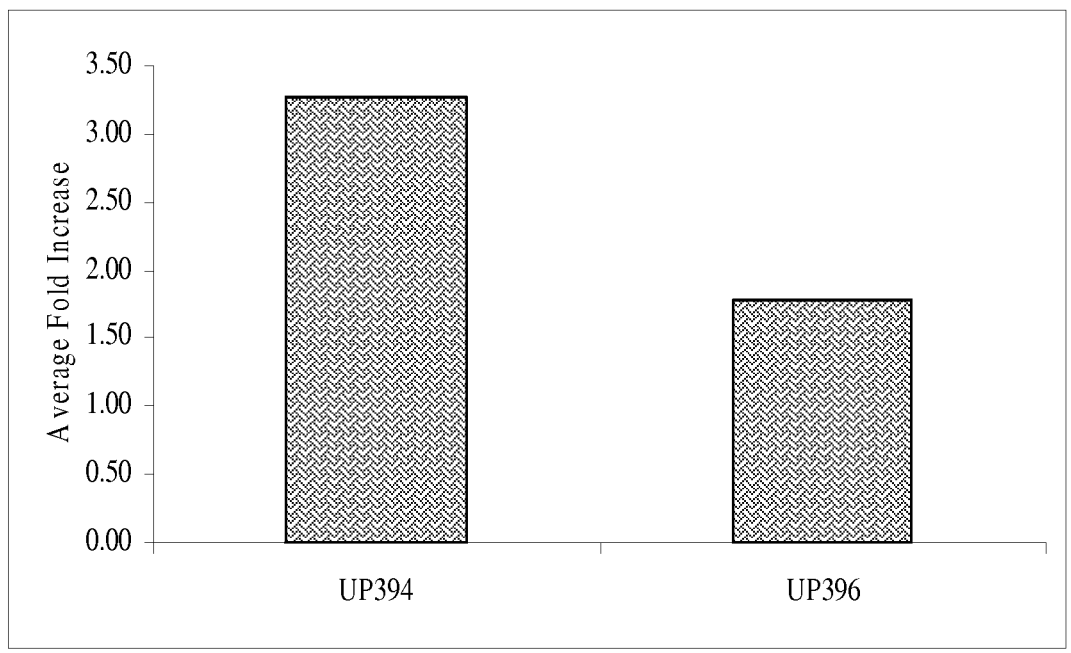
FIG. 7 illustrates graphically the effect of UP394 (aloesin) and UP396 (aloesinol) on adiponectin levels secreted into the media of differentiated 3T3-L1 cells. Briefly, 3T3-L1 cells were induced to differentiate then treated with UP394 (aloesin) and UP396 (aloesinol) at concentrations of 30 µM for 48 hours. Adiponectin concentrations in the culture media were determined with an ELISA kit for adiponectin.

De-replication of the active sub-fractions was conducted using LC-MS/PDA. Unique compound peaks were identified corresponding to the strongest adiponectin enhancement activity. The most active compounds aloesinol (mw=396) and aloesin (mw=394) in P0017-OE-HTPF3 and P0017AC1/2 were identified as described in Example 8 as chromone type compounds coded as UP394 for aloesin (FIG. 5) and UP396 for aloesinol (FIG. 6), respectively. Specifically, aloesin and aloesinol were isolated and identified as active chromone compounds that enhanced adiponectin secretion from adipocytes. Purified UP394 and UP396 were tested in as described in Example 10 and both chromone compounds were active in increasing adiponectin production from the adipocytes in the in vitro assay as shown in FIG. 7.

Example 9 describes a method for purifying chromones from crude aloe exudates in order to remove anthraquinone contaminants (specifically, aloin A and B) by preparative column chromatographic separation and recrystallization. Anthraquinones are undesirable in that they cause significant adverse side effects such as inducing diarrhea and genotoxicity, and therefore prevent the direct use of the crude chromone extracts. The purity of chromones isolated following purification via this method is as high as 70%, preferably 80% and most preferably 90% or greater by weight, which is "essentially free of anthraquinones" as quantified by HPLC. By essentially free of anthraquinones it is meant that the total amount of anthraquinones in the purified compositions is less than 100 ppm, preferably less than 50 ppm (of aloin A and B). In the crude exudate of *Aloe ferox*, the amount of aloesin (UP394) is approximately 25% by weight and the amount of anthraquinones is approximately 22% (Zahn, (2007) Phytochem. Anal. (10): 1002-1024). Thus, *Aloe ferox* is an excellent and preferred plant source for the isolation of chromone compositions. The isolated and purified aloesin (UP39) (Lot# A-2705 & Lot# I1506AW) isolated from *Aloe ferox* leaf exudates, as described in Example 9, had purity of 93% and 100.6%, respectively with total anthraquinone less than 50 ppm. The anthraquinone free (<50 ppm total anthraquinones) aloesin (UP394) was utilized to produce chromone enriched composition N931 and UP780 as illustrated in the Example 11 and 18.

The amount of chromones, in other *Aloe* species, such as *Aloe barbadensis*, (which is a preferred source of *Aloe* gel), however, is reportedly much lower (0.32 mg/g; 0.032% with total chromones at 0.10%) and anthraquinones (Aloin A & B) almost four times higher (1.14 mg/g or 0.114%) (Park (1998) Phytochem. Anal. 9:186-191). Additionally, chromones are stored only in the rinds or the outside layer of the leaves of aloe plants. In the standard process of obtaining aloe gel products, from *Aloe* plants such as *Aloe vera/Aloe barbadensis* the rinds of the aloe leaves are typically removed and only the clear gel is filtered and concentrated. Even in the production of the aloe whole leaf gel powder, in which the whole leaves of aloe plants are crushed and the gel is collected and filtered, a decolonization process using active charcoal and other processing steps removes essentially all of the chromones as well as the anthraquinones. Therefore, no significant amounts of chromones or anthraquinones are found in standard aloe gel products as verified via HPLC (Dell'Agli (2007) J. Agric. Food Che. 55(9):3363-3367; Zonta (1995) Journal of Chromatography A 718(1): 99-106).

It was postulated by the inventors that enriching the chromones in a standardized plant extract would provide compositions with improved and more consistent activity in enhancing insulin sensitivity, improving glucose tolerance and lowering triglyceride levels. In order to test the hypothesis, a unique chromone composition of matter was produced as demonstrated in Example 11 by combining a chromone aloesin (UP394) isolated from the leave exudates of *Aloe ferox* with a whole leaf gel powder prepared from *Aloe vera*. The standardized chromone composition from these two species of *Aloe* contained no less than 1.4% chromones—i.e. aloesin (UP394) without contamination from anthraquinones (<50 ppm of Aloin A &B). Aloesin (UP394) was extracted from the leave exudates of *Aloe ferox*, isolated by a preparative chromatographic column and then further purified by re-crystallization as described in U.S. Pat. No. 6,451,357 entitled "Method of Purification of Aloesin," which is incorporated herein by reference in its entirety. This unique standardized chromone composition was coded as N931 and was tested for its effect on blood glucose levels, insulin resistance and fat metabolism in a different insulin resistance model, the db/db mouse model.

Since adiponectin has been reported as improving insulin resistance, which is considered a root cause of metabolic syndrome, it was postulated that the reduction in insulin resistance by chromones UP394 and UP396 should lead to improvement in various metabolic disorders. To test this theory, impaired insulin sensitivity, glucose tolerance and metabolic disorders were induced in C57BL/6J mice by feeding the animals a high fat diet for 8 weeks as illustrated in Example 12. (Surwit et al. (1988) Diabetes 37:1163-1167; Laakso et al. (2004). Diabetes Care 27:2253-2259; Kahn et al. (2004) Diabetes 53:3274-3285; Scheurink et al. (1998) European J Endo. 139:461-467). The mice were then treated (injection or oral) with chromones UP394, UP396 and a reference compound GW1929 (N-(2-Benzoylphenyl)-O-[2-(methyl-2-pyridinylamino) ethyl]-L-tyrosine) for four weeks.

Figure 8A:
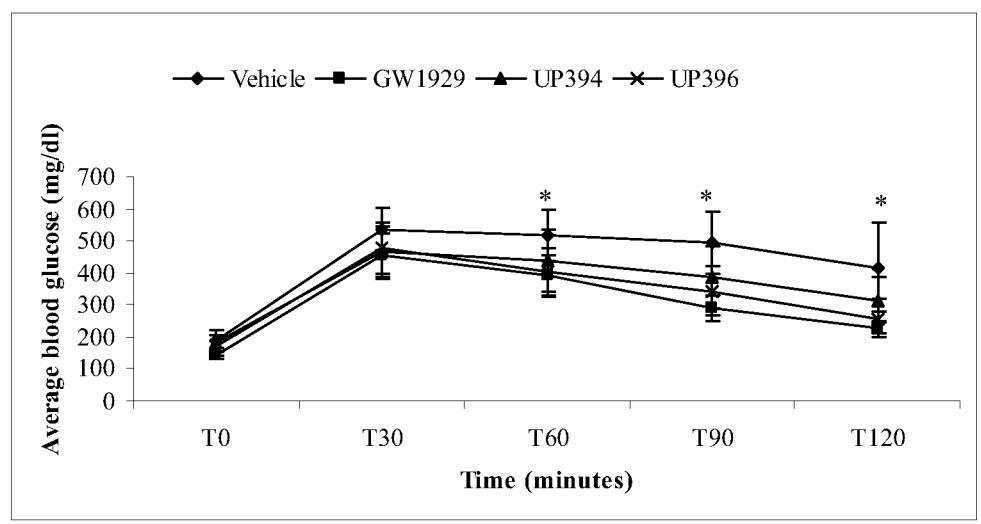
FIG. 8A illustrates the results of an intraperitoneal glucose tolerance test conducted on C57BL/6J mice at a dose of 2 g/kg on day 18 after treatment. Briefly, animals were fasted for 3 hours before glucose administration. Mice were treated with GW1929 (5 mg/kg) (■), UP394 (100 mg/kg) (▲), UP396 (100 mg/kg) (x) and vehicle (♦) intraperitoneally. Blood glucose levels were measured at time 0, 30, 60, 90, and 120 minutes. Animals were provided with a high fat diet for 12 weeks. Treatment started on week 8. The data are means±SD, n=6. Significant glucose utilization was observed at times 60, 90 and 120 minutes for GW1929 and UP396 when compared to vehicle, p<0.05 (*). P-values for GW1929, UP394 and UP396 were at T0 as 0.00, 0.87, and 0.43; at T30 as 0.07, 0.16 and 0.23, respectively when compared to vehicle. P-values for UP394 were at T60 as 0.15; at T90 as 0.10 and at T120 as 0.17, when compared to vehicle.

The therapeutic effect of the disclosed chromones on insulin resistance in the high fat diet mice was demonstrated using two tests: a glucose tolerance test (Example 13) and an insulin tolerance test (Example 14). An intraperitoneal glucose tolerance test was conducted on day 18 of the treatment with the disclosed chromones aloesin (UP394) and aloesinol (UP396). Animals were fasted for 3 hours before glucose administration (2 g/kg). Blood glucose levels were measured at 0, 30, 60, 90, and 120 minutes after the administration of glucose. As shown in Example 13 and FIG. 8A, the animals treated with UP396 showed a significant improvement of glucose clearance from the circulation compared to the vehicle treated animals. The animals treated with UP394, showed a clear trend of improvement compared to the animals treated with vehicle (FIG. 8A).

Figure 8B:
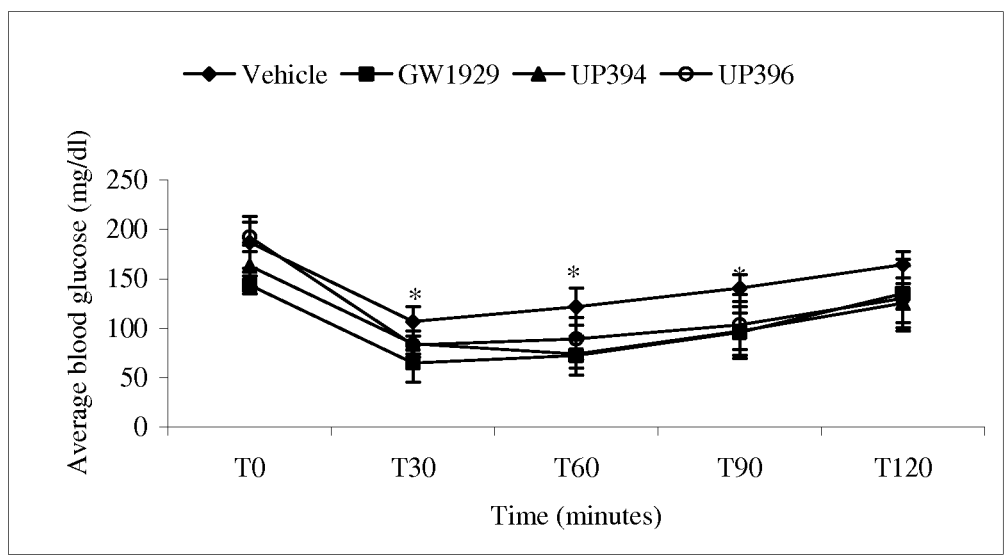
FIG. 8B illustrates the results of an intraperitoneal insulin tolerance test performed on C57BL/6J mice at a dose of 0.5 unit/kg on day 24 of active treatment. Briefly, animals were fasted for 3 hours before insulin injection. Mice were treated with GW1929 (■), UP394 (▲), UP396 (x) and vehicle (♦) for 24 days. Blood glucose levels were measured at time 0, 30, 60, 90, and 120 minutes. Animals were provided with a high fat diet for 12 weeks. Treatment started on week 8. The data are means±SD, n=6. A significant glucose clearance was observed at time points of T30, T60 and T90 for UP394 and UP396 as well as GW1929 when compared to vehicle, p<0.05 (*). P-values for GW1929, UP394 and UP396 were at T0 as 0.00, 0.14 and 0.67; at T120 as 0.08, 0.00 and 0.04, respectively when compared to vehicle.

The intraperitoneal insulin tolerance test was performed on day 24 of the treatment as shown in Example 14. Animals were fasted for 3 hours before insulin injection. Blood glucose levels were measured at 0, 30, 60, 90, and 120 minutes after the administration of insulin (0.5 units/kg). As shown in FIG. 8B and Example 14, significant glucose clearance was observed in the animals treated with both UP394 and UP396 compared to vehicle-treated animals, $p<0.05$ (FIG. 8B).

Figure 9:
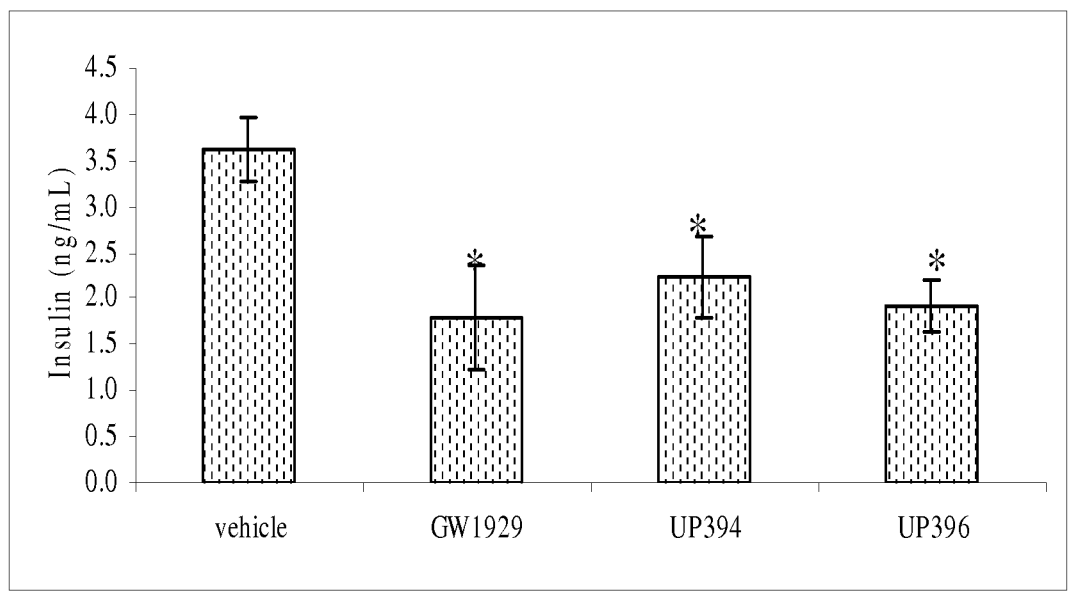
FIG. 9 illustrates graphically the effect of UP394 and UP396 on insulin levels using the High-Fat Diet Induced Diabetes Model. Animals were treated with GW1929 (5 mg/kg), UP394 (100 mg/kg), UP396 (100 mg/kg) and vehicle intraperitoneally for 2 weeks after the 8-week induction of metabolic disorders with high-fat diet. Blood was collected by tail vein and spun down for plasma. The plasma insulin levels were measured with an ELISA kit for insulin (Crystal Chem—Chicago, Ill.).

The insulin sensitizing activity of the disclosed chromones was further demonstrated by the ability of the compounds to lower plasma insulin levels in treated animals. The plasma levels of insulin in the mice were determined using an ELISA kit (FIG. 9). The reference compound GW1929, a selective PPARγ agonist, decreased the insulin level significantly as expected. Similarly, UP394 and UP396 also decreased the insulin levels significantly compared to vehicle treated mice (FIG. 9), indicating that the disclosed chromone compounds increased insulin sensitivity in the high fat diet induced metabolic disorder mice.

Figure 10:
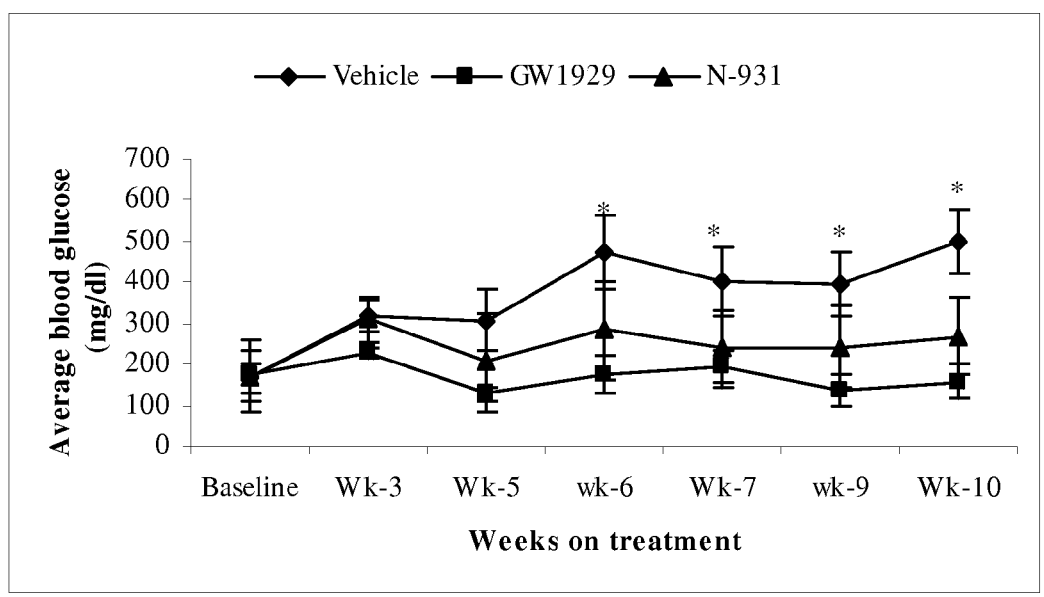
FIG. 10 illustrates graphically weekly fasting glucose levels of male db/db mice treated with GW1929 (■), N931 (▲) and vehicle (♦) for 10 weeks. Animals were provided with T2018 rodent diet ad libitum except when fasting. Animals were fasted overnight before measurements were taken. The values indicated are means±SD, n=8, fasting blood glucose levels were significantly lower for GW1929 and N-931 at weeks 6, 7, 9 and 10, when compared to vehicle P<0.05 (*).

Mice homozygous for the diabetes spontaneous mutation (Lepr$^{db}$) become identifiably obese at around 3 to 4 weeks of age. Elevations of plasma insulin begin at 10 to 14 days and of blood sugar at 4 to 8 weeks. Homozygous mutant mice are polyphagic, polydipsic, and polyuric. The course of the disease is markedly influenced by genetic background. A number of features are observed on the db/db mice, including an uncontrolled rise in blood sugar, severe depletion of the insulin-producing beta-cells of the pancreatic islets, and death by 10 months of age. Male db/db mice (8 in each group) were treated (injection or oral) with GW1929 (5 mg/kg), N931 (375 mg/kg) and vehicle for 10 weeks and fasting glucose levels of the mice were measured weekly as demonstrated in Example 15. As a result, N931 was very efficacious in lowering blood glucose level in db/db mice. As shown in FIG. 10, the glucose level in the vehicle-treated mice increased over time during the 10-week treatment. GW1929, the reference compound, was able to maintain the glucose at the baseline level as expected. Similar to GW1929, N931 reduced glucose levels substantially, starting from week 5 of the treatment. Fasting blood glucose levels were significantly lower in N931 treated group at weeks 6, 7, 9 and 10, when compared to the vehicle treated group, P<0.05. After 10 weeks of treatment, the glucose level in the animals treated with N931 was 54% of that in the animals treated with vehicle.

Figure 11A:
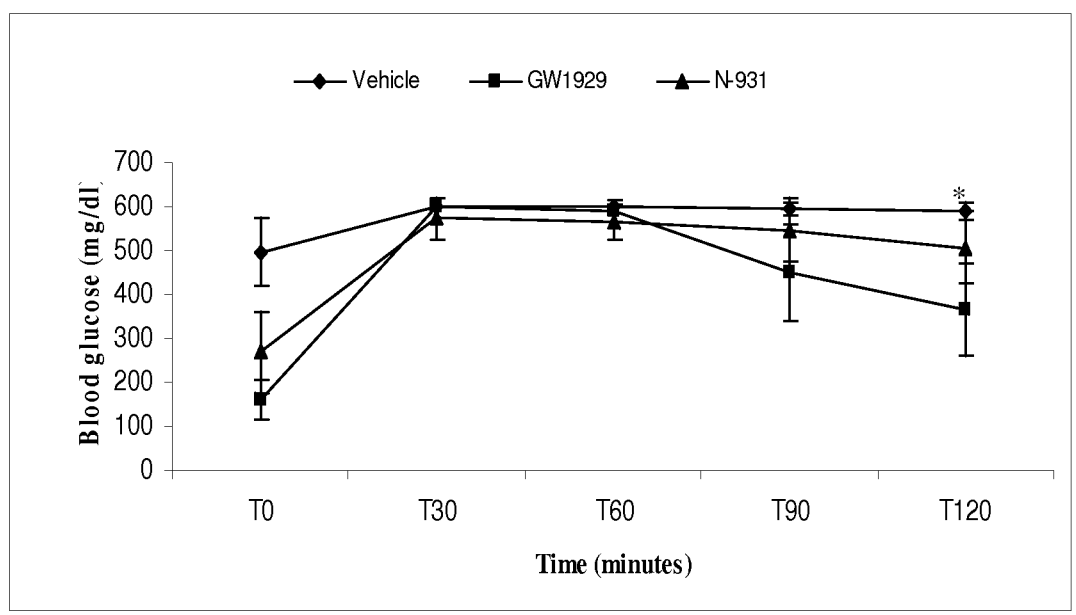
FIG. 11A depicts the results of an oral glucose tolerance test conducted on db/db mice at a dose of 3 g/kg after 10 weeks of treatment. Animals were fasted overnight before glucose load. Mice were treated with GW1929 (■), N931 (▲) and vehicle (♦) for 10 weeks. Blood glucose levels were measured at time 0, 30, 60, 90, and 120 minutes. Animals were provided with T2018 rodent diet ad libitum except when fasting. The data are means±SD, n=8. Significant glucose utilization was observed at times 0, and 120 minutes for both GW1929 and N-931 when compared to vehicle, P<0.05 (*). P-values for GW1929 and N931 were at T30 as 0.15, and 0.05; at T60 as 0.33, and 0.02; at T90 as 0.002, and 0.083, respectively when compared to vehicle.

The effect of N931 on insulin resistance was demonstrated in an oral glucose tolerance test as described in Example 16. The db/db mice (8 mice in each group) were treated with GW1929 (5 mg/kg), N931 (375 mg/kg) and vehicle for 10 weeks. The animals were fasted overnight before glucose load. Blood glucose levels were measured at time 0, 30, 60, 90, and 120 minutes after the glucose administration. Significant glucose clearance from the circulation was observed at time 0 and 120 minutes in the group treated with GW1929 or N-931 when compared to the vehicle group, P<0.05 (FIG. 11A). The results indicate that N931 has the ability to increase the glucose tolerance, therefore improve the insulin sensitivity of db/db mice.

Figure 11B:
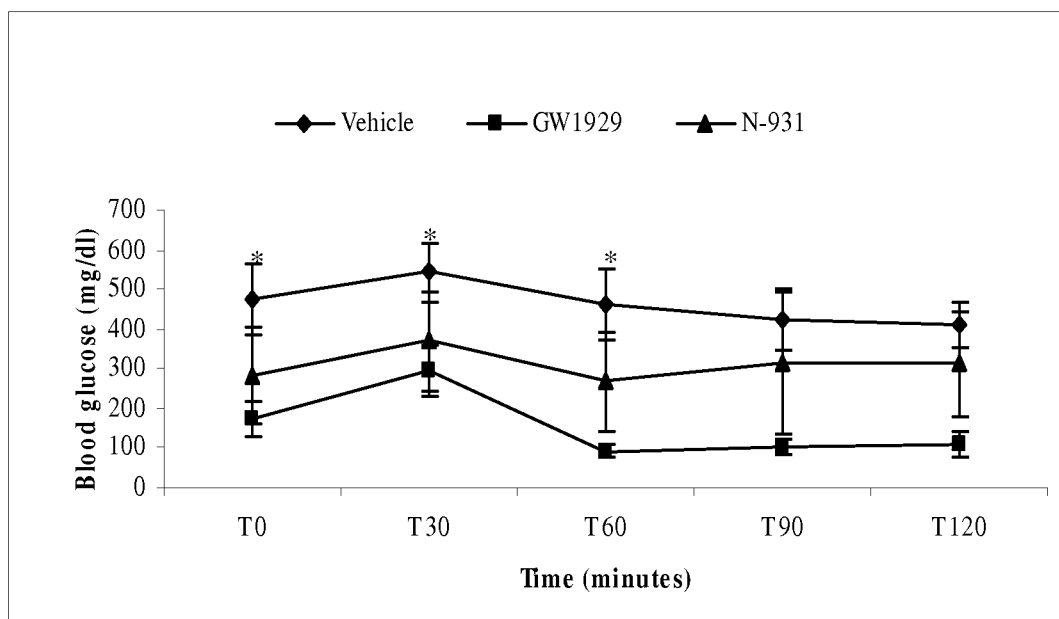
FIG. 11B depicts the results of an intraperitoneal insulin tolerance test performed on db/db mice at a dose of 0.5 unit/kg after six weeks of treatment. Animals were fasted overnight before insulin injection. Mice were treated with GW1929 (■), N931 (▲) and vehicle (♦) for 10 weeks. Blood glucose levels were measured at time 0, 30, 60, 90, and 120 minutes. Animals were provided with T2018 rodent diet ad libitum except when fasting. The data are means±SD, n=8. A significant glucose clearance was observed at times 0, 30 and 60 minutes for both GW1929 and N-931 when compared to vehicle, p<0.05 (*). P-values for GW1929 and N931 were at T90 as 0.00, and 0.14, and at T120 as 0.00, and 0.09, respectively when compared to vehicle.

The effect of N931 on insulin resistance was further demonstrated in an intraperitoneal insulin tolerance test. The db/db mice (8 in each group) were treated with GW1929 (5 mg/kg), N931 (375 mg/kg) and vehicle for 6 weeks. Blood glucose levels were measured at 0, 30, 60, 90, and 120 minutes after the injection of insulin. Again, improved insulin sensitivity was evident in the mice treated with GW1929 and N931. Significant glucose clearance was observed at 0, 30 and 60 minutes for both GW1929 and N931 when compared to vehicle, P<0.05 (FIG. 11B).

Figure 12:
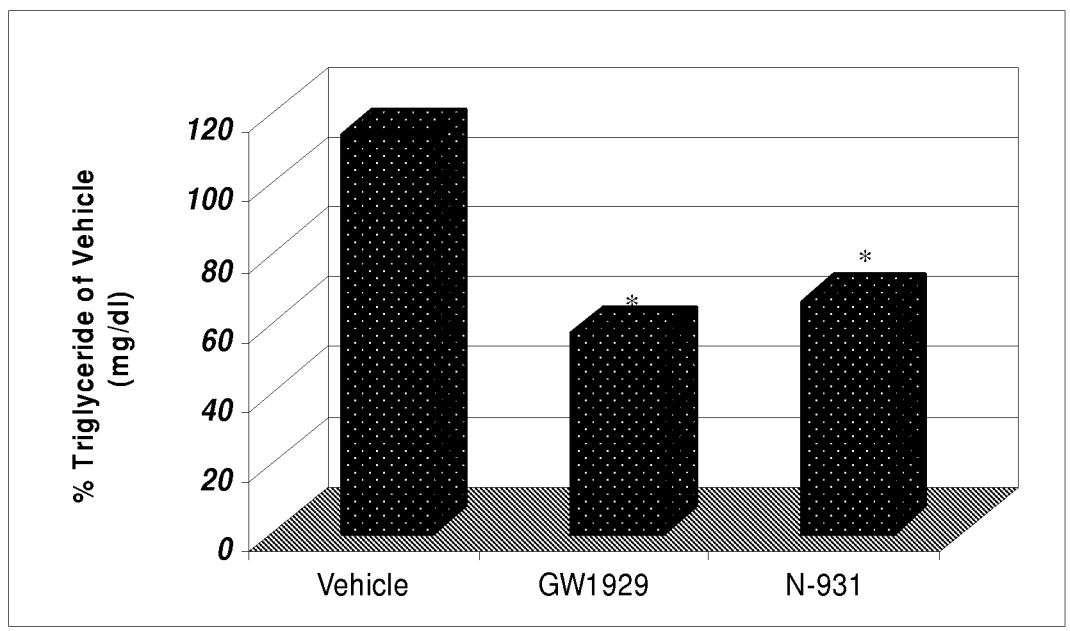
FIG. 12 illustrates graphically the weekly fasting triglyceride levels of male db/db mice treated with GW1929, N-931 and vehicle for 10 weeks. Animals were provided with T2018 rodent diet ad libitum except when fasting. Animals were fasted overnight before measurements were taken. The values indicated are percent triglyceride levels of vehicle, n=8. A significant reduction in triglyceride levels were found in animals treated with GW1929 and N-931 when compared to vehicle after 10 weeks of treatment, P<0.05 (*).

In addition, N931 reduced triglyceride levels significantly compared to the vehicle group (P<0.05) after the treatment for 10 weeks. Fasting triglyceride levels of male db/db mice treated with GW1929, N931 and vehicle were measured weekly as shown in Example 17. Animals were provided with T2018 rodent diet ad libitum except when fasting. After 10 weeks of treatment, a 34% reduction of triglycerides was observed in the animals treated with N931 (P<0.05), and a 43% reduction was observed in the reference compound group (P<0.05) (FIG. 12).

In order to demonstrate the superior and unexpected therapeutic efficacy of a chromone enriched composition, a second unique composition of matter that was produced by combining the chromone aloesin (UP394) isolated from the leave exudates of *Aloe ferox* with a leaf gel powder (Qmatrix coded as QM400) made from *Aloe vera*. This standardized chromone composition (UP780) from these two species of *Aloe* contained no less than 2% chromones—i.e. aloesin (UP394) and not more than 50 ppm of total anthraquinones by HPLC quantification. The chromone aloesin (UP394) was extracted from the leave exudates of *Aloe ferox*, isolated by a preparative chromatographic column and then further purified by re-crystallization as described in Example 9 and further as described in U.S. Pat. No. 6,451,357, entitled "Method of Purification of Aloesin," which is incorporated herein by reference in its entirety. This novel standardized chromone composition was coded as UP780 and was orally administered in a dose range finding study in high fat diet fed C57BL/6J mice. In this study, the insulin sensitizing activity of UP780 was compared with a pharmaceutical drug—GW1929 and also with the original *Aloe vera* gel powders (Qmatrix QM400), which does not contain significant amounts of chromones as quantified by HPLC in Example 9.

Figure 13A:
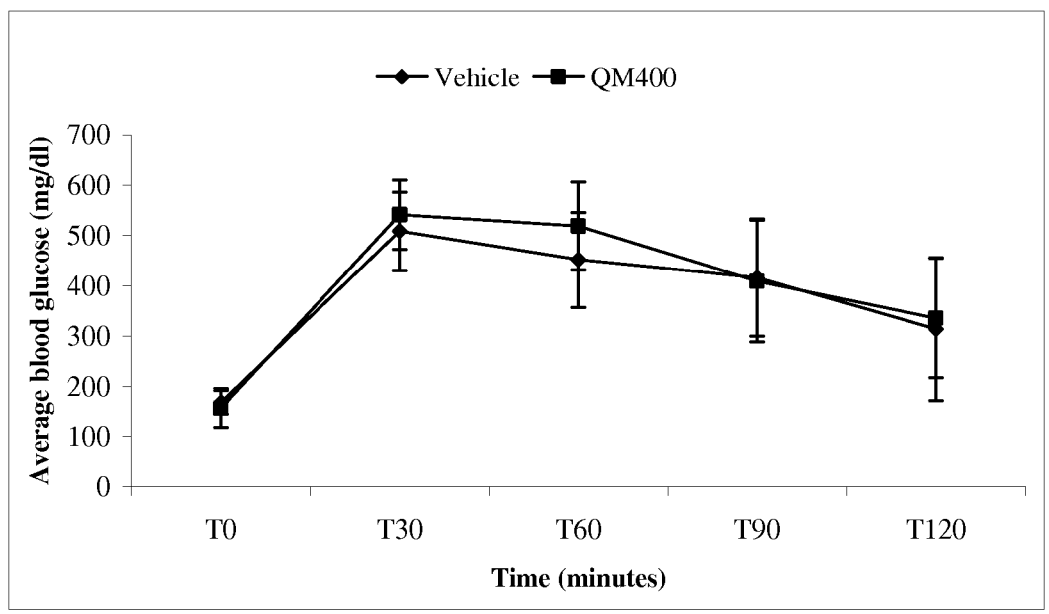
FIGS. 13A-13F illustrate the results of an intraperitoneal glucose tolerance test conducted on week 3 after onset of treatment. On the test day, animals were fasted for 3 hours and received intraperitoneal administration of glucose at a dose of 2 mg/g. Blood glucose levels were determined at time 0 (before glucose injection), 30, 60, 90, and 120 minutes post glucose delivery. Blood was obtained from tail vein. The data are means±SD, n=7. A. vehicle (♦) vs. 400 mg/kg Qmatrix®, B. vehicle (♦) vs. GW1929 (■), C. vehicle (♦) vs. UP780 (100 mg/kg) (■), D. vehicle (♦) vs. UP780 (200 mg/kg) (■), E. vehicle (♦) vs. UP780 (400 mg/kg) (■) and F. Vehicle (♦) vs. regular rodent diet fed animals, P<0.05 (*). Efficacy of UP780 was detected as early as three weeks of treatment. After three weeks of daily oral treatment, a statistically significant glucose clearance was found at times 30, 60 and 90 minutes post intraperitoneal glucose load for animals treated with 200 mg/kg UP780 and GW1929. Similarly, animals treated with 400 mg/kg UP780 showed significant glucose utilization at time 30 minute, P≤0.05 (*).
Figure 13B:
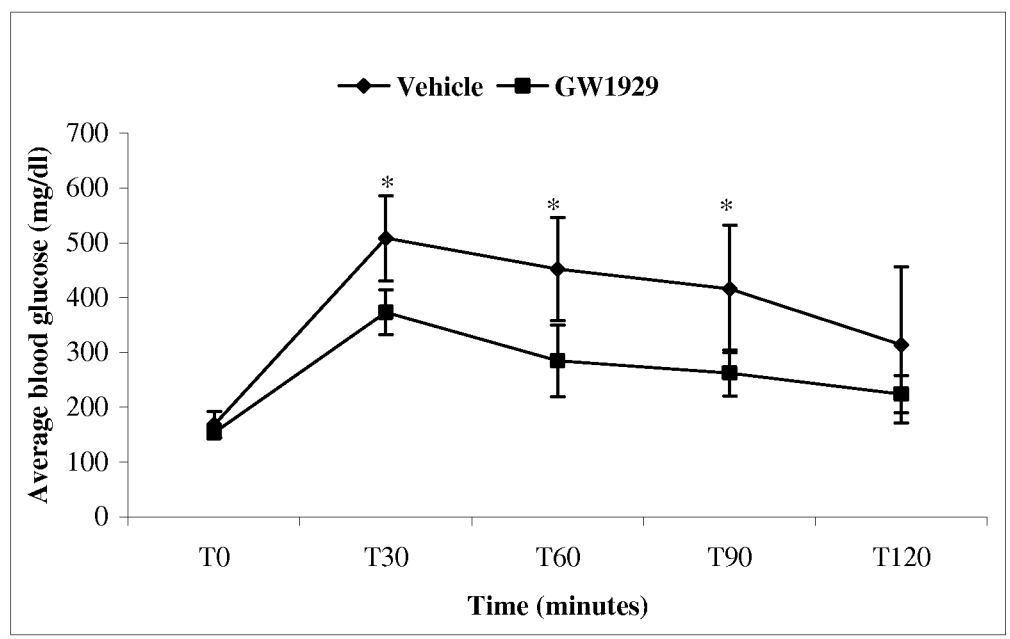
Figure 13C:
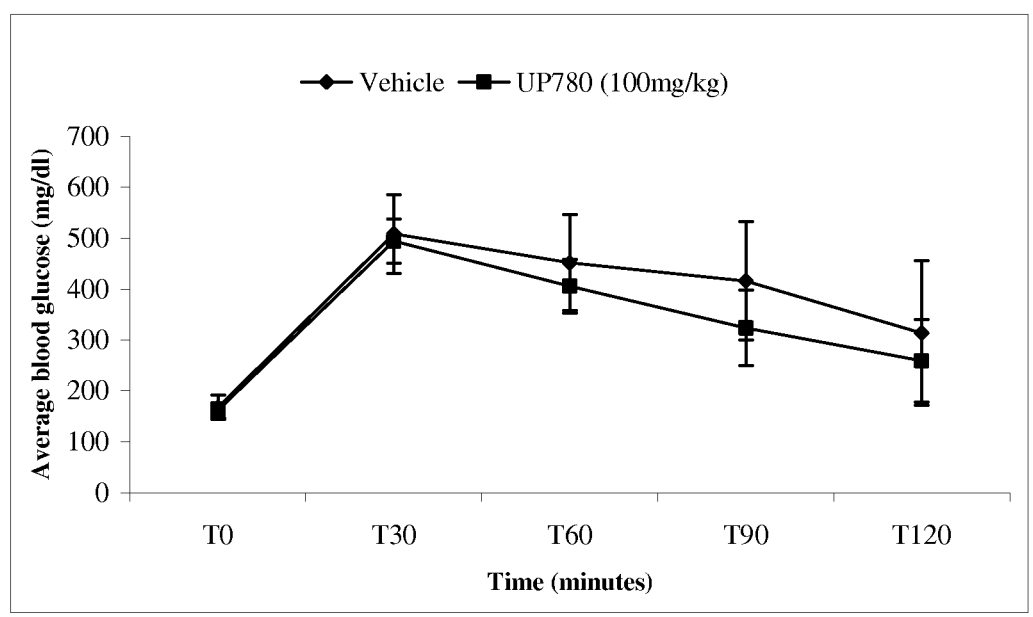
Figure 13D:
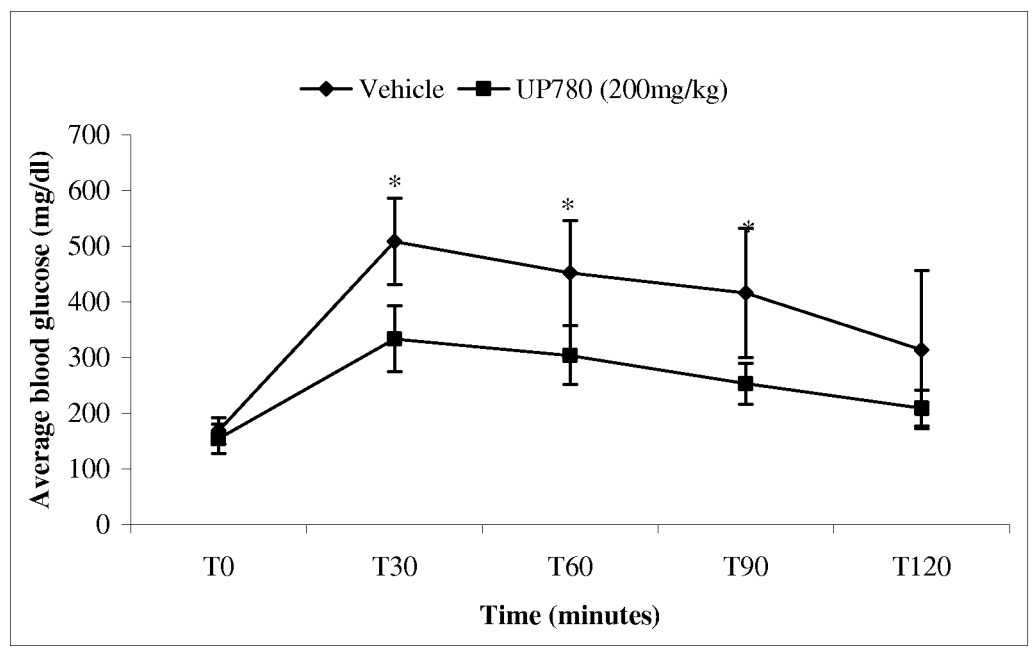
Figure 13E:
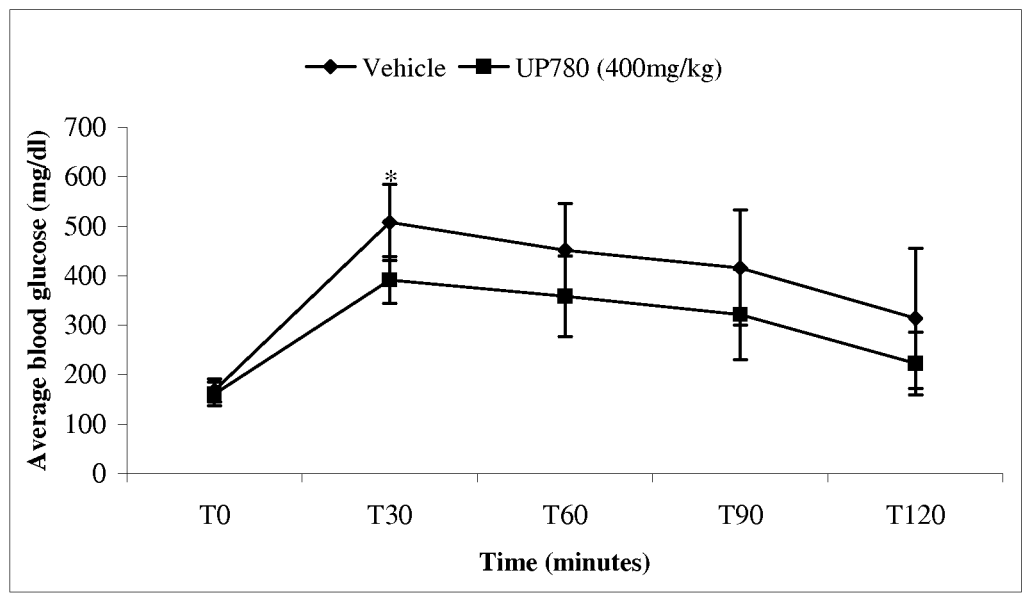
Figure 13F:
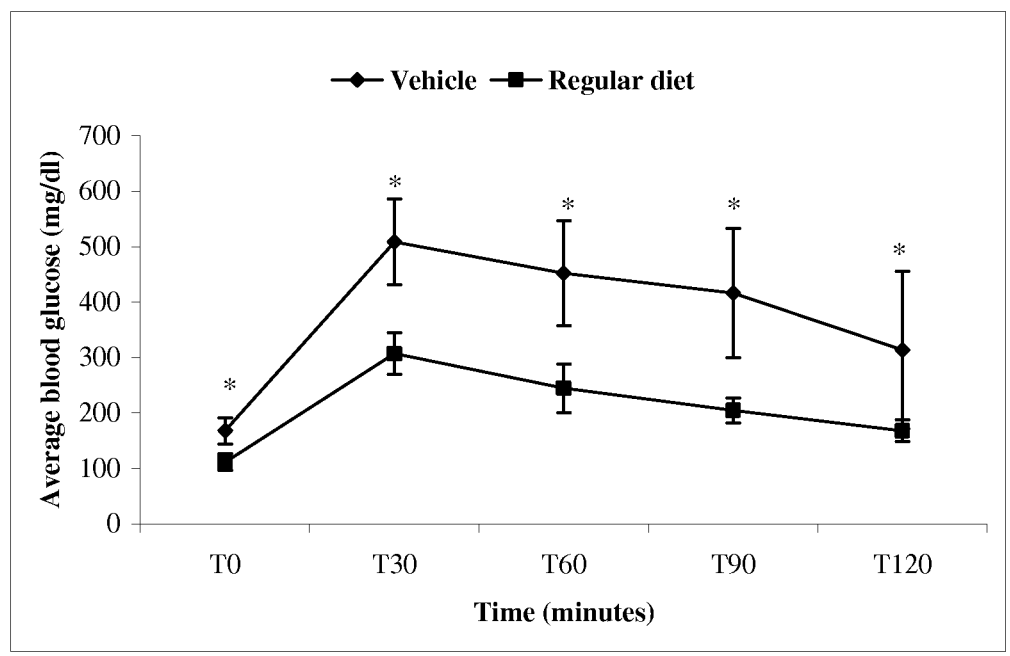
Figure 14A:
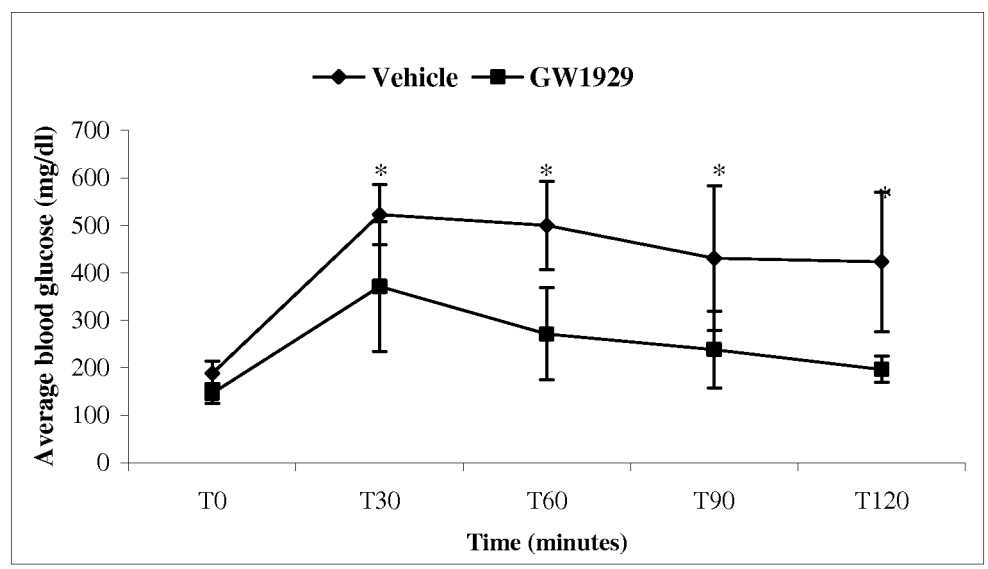
FIGS. 14A-14E illustrate the results of an intraperitoneal glucose tolerance test conducted on week 9 after onset of treatment. On the test day, animals were fasted for 3 hours and received intraperitoneal administration of glucose at a dose of 2 mg/g. Blood glucose levels were determined at time 0 (before glucose injection), 30, 60, 90, and 120 minutes post glucose delivery. Blood was obtained from tail vein. The data are means±SD, n=7. A. vehicle (♦) vs. GW1929 (■), B. vehicle (♦) vs. Qmatrix® (400 mg/kg) (■), C. vehicle (♦) vs. UP780 (100 mg/kg) (■), D. vehicle (♦) vs. UP780 (200 mg/kg) (■) and E. vehicle (♦) vs. UP780 (400 mg/kg) (■), P<0.05 (*). Compared to vehicle control, animals treated with 400 mg/kg UP780 and Qmatrix® showed statistically significant differences in glucose utilization at times 30, 60, 90 and 120 minutes post IP glucose administration, P≤0.05 (*), after 9 weeks of daily oral treatment. The 100 mg/kg UP780 treated animals showed a significant difference only at T30. The positive control, GW1929, has P-values less than 0.05 at each time points analyzed.
Figure 14B:
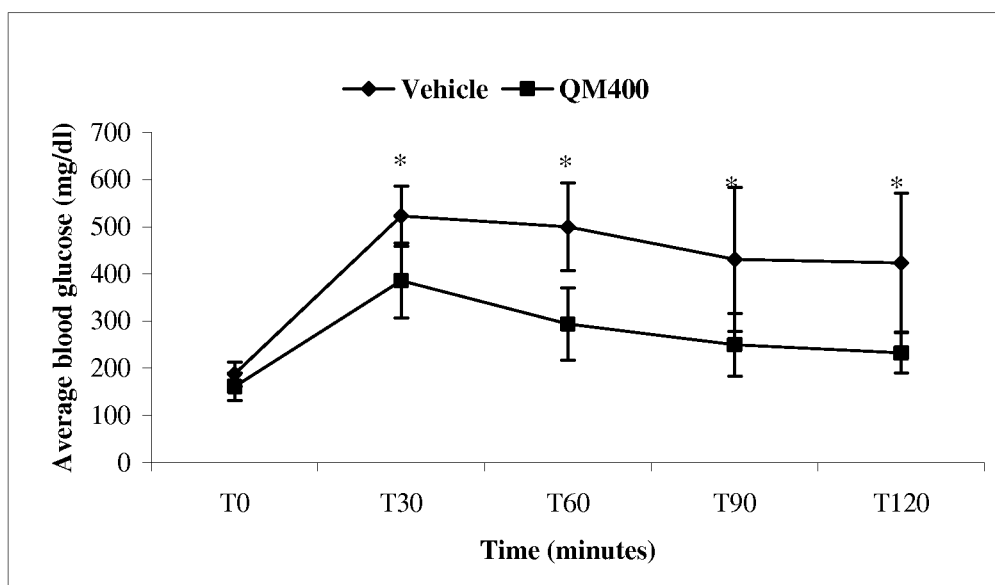
Figure 14C:
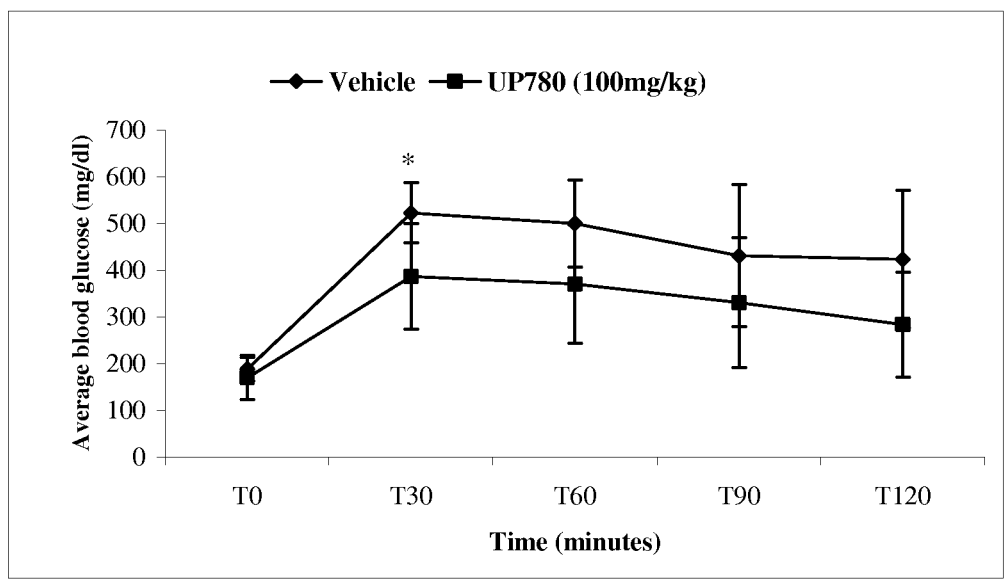
Figure 14D:
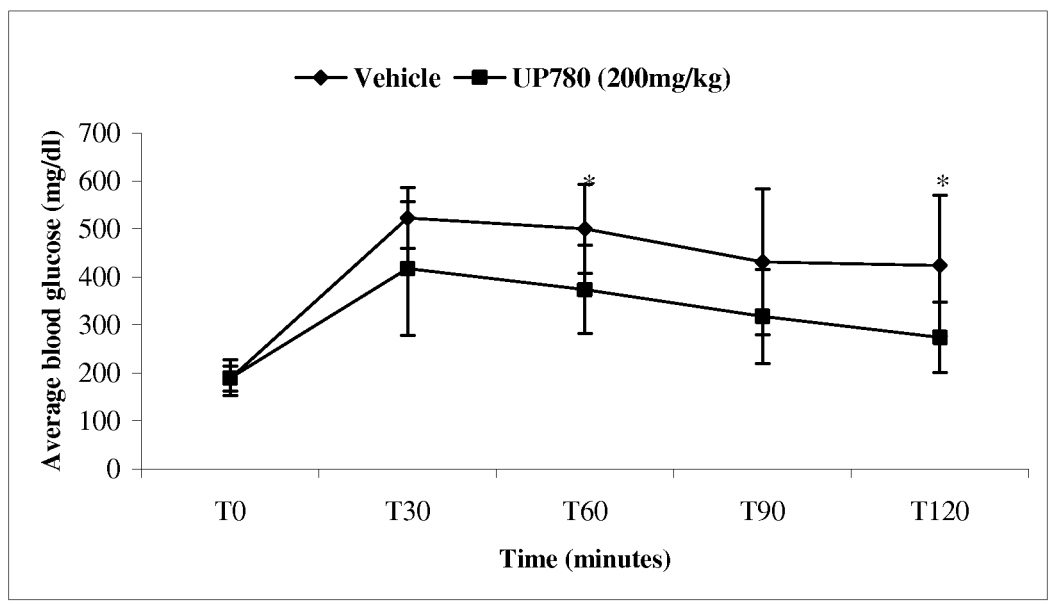
Figure 14E:
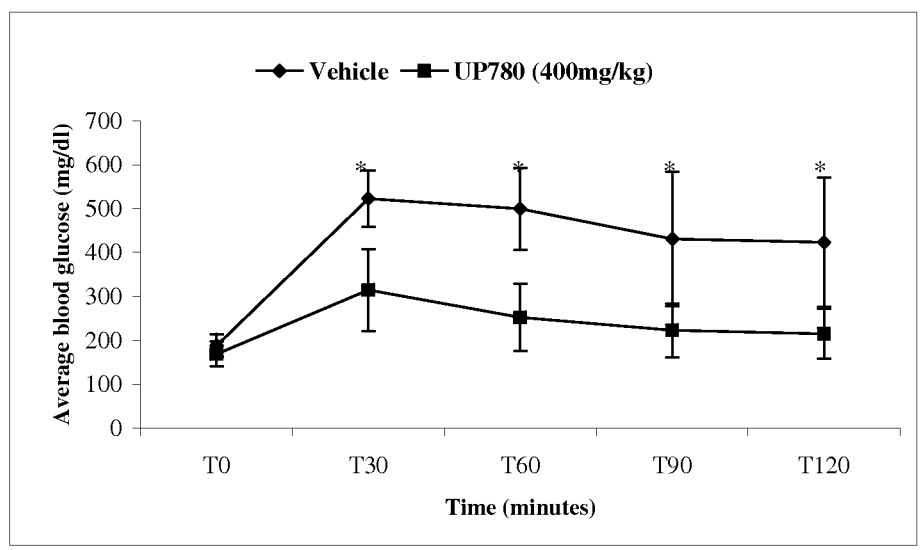

After three weeks of daily oral treatment in Example 19, a statistically significant glucose clearance was found at times 30, 60 and 90 minutes post intraperitoneal glucose load for animals treated with 200 mg/kg of UP780 (FIG. 13D) and GW1929 (FIG. 13B). Similarly, animals treated with 400 mg/kg of UP780 showed significant glucose utilization at time 30 minutes, P≤0.05 (*) (FIG. 13E). Likewise, after 9 weeks of oral treatment, animals treated with 400 mg/kg of UP780 showed statistically significant differences in glucose utilization at times 30, 60, 90 and 120 minutes post IP glucose administration, P≤0.05 (*) (FIG. 14E), when compared to vehicle control. The 100 mg/kg UP780 treated animals showed a significant difference at T30 (FIG. 14C). The positive control, GW1929, has P-values less than 0.05 at each time point analyzed. While, the original *Aloe vera* gel powders (Qmatrix QM400), which does not contain significant amounts of chromones, showed no efficacy after three weeks of oral consumption (FIG. 13A). This experiment clearly showed an unexpected and superior insulin sensitization efficacy of a chromone enriched composition compared to the composition without chromones.

Figure 15A:
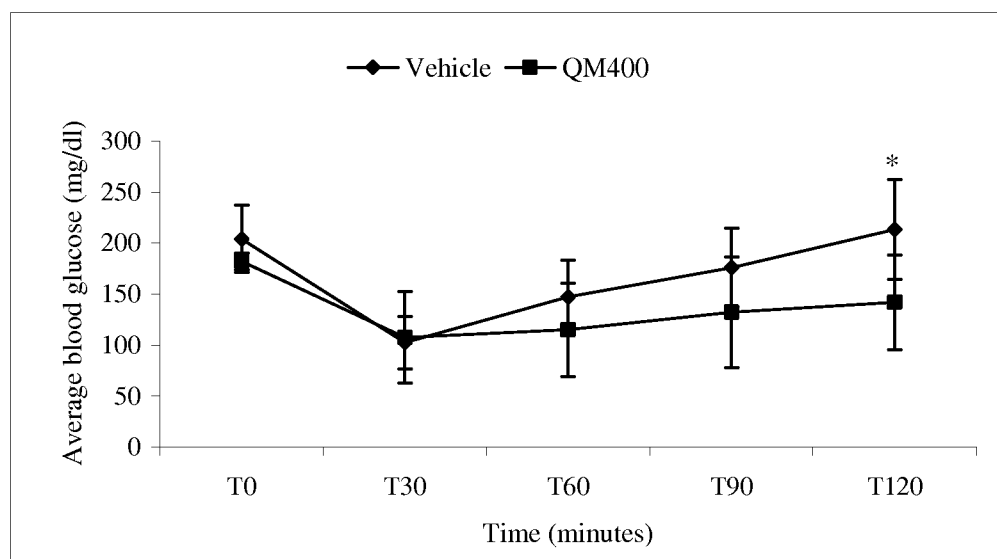
FIGS. 15A-15E illustrate the results of an intraperitoneal insulin tolerance test conducted on week 3 after onset of treatment. On the test day, animals were fasted for 3 hours and received intraperitoneal administration of insulin at a dose of 0.5 unit/kg. Blood glucose levels were determined at time 0 (before glucose injection), 30, 60, 90, and 120 minutes post glucose delivery. Blood was obtained from tail vein. The data are means±SD, n=7. A. vehicle (♦) vs. Qmatrix® (400 mg/kg) (■), B. vehicle (♦) vs. UP780 (100 mg/kg) (■), C. vehicle (♦) vs. UP780 (200 mg/kg) (■), D. vehicle (♦) vs. UP780 (400 mg/kg) (■) and E. vehicle (♦) vs. GW1929, P<0.05 (*). The insulin sensitizing effect of UP780 was verified in insulin tolerance test after 10 weeks of daily oral treatment. Statistically significant insulin sensitization was observed for animals treated with 400 mg/kg UP780 for all of the time points considered, P≤0.05 (*). There were no other significance differences observed for the rest of the treatment groups, except GW1929 after 1 hour insulin injection, P≤0.05.
Figure 15B:
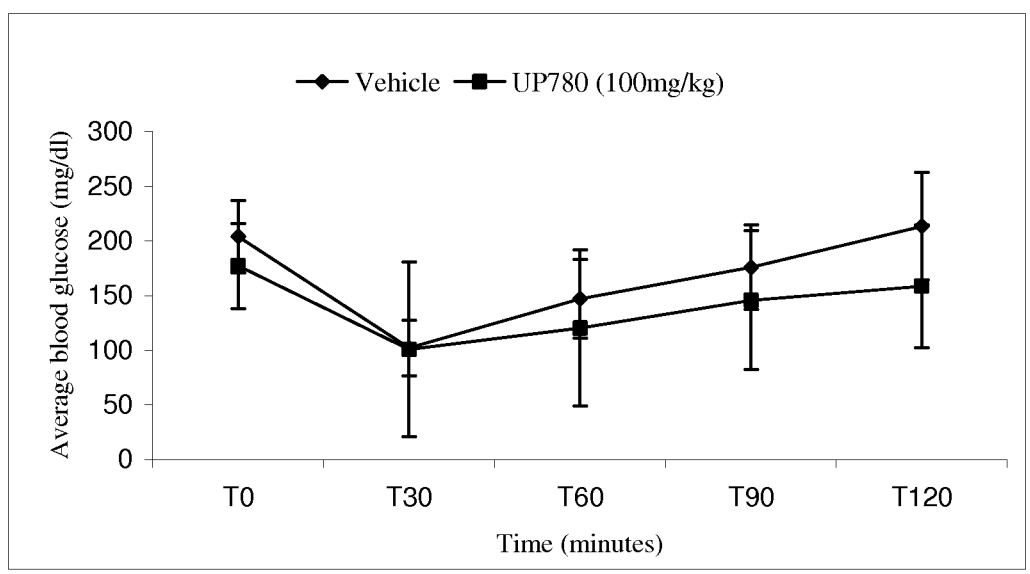
Figure 15C:
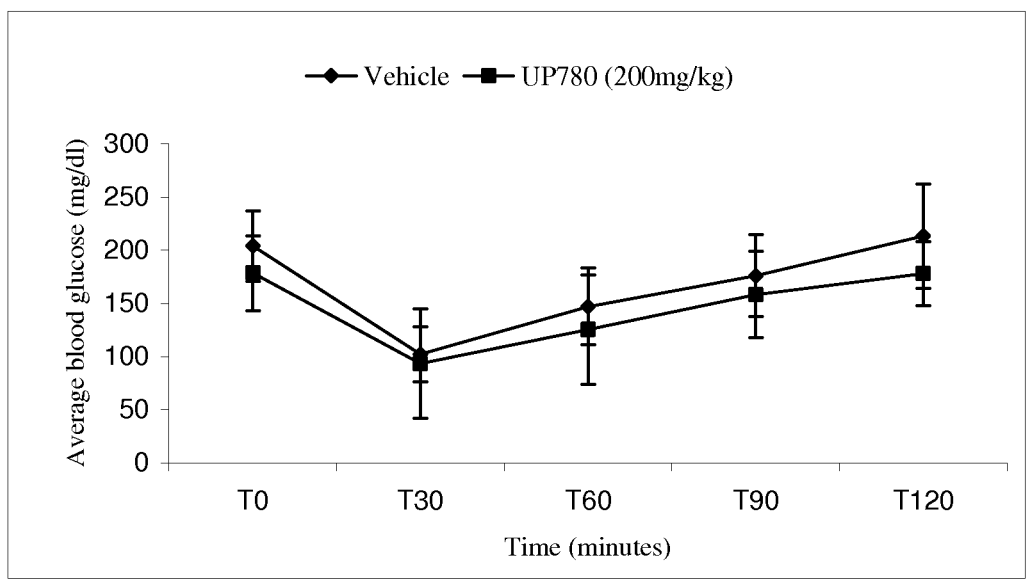
Figure 15D:
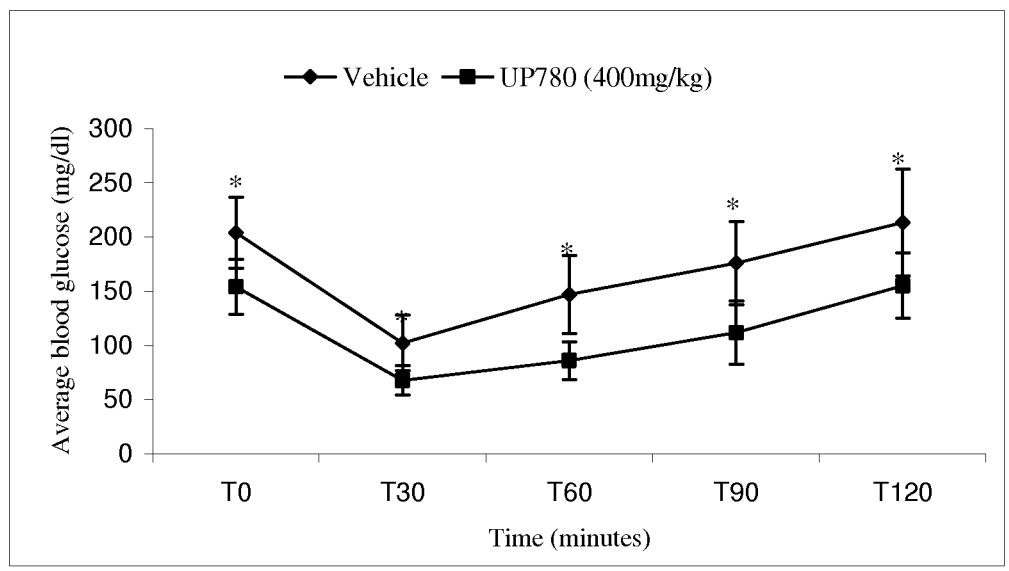
Figure 15E:
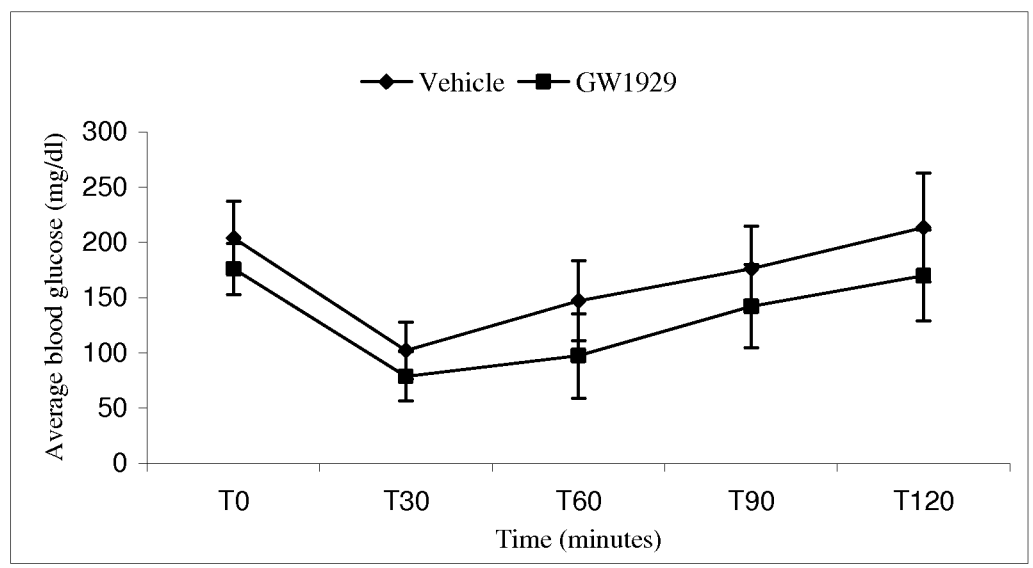

Moreover, the insulin sensitizing effect of UP780 was verified in an insulin tolerance test after 10 weeks of daily oral treatment (FIG. 15A-15E). Coinciding with the glucose tolerance data, statistically significant insulin sensitization was observed for animals treated with 400 mg/kg of UP780 for all the time points considered, P≤0.05 (*) (FIG. 15D). In comparison, the *Aloe vera* gel powders (Qmatrix QM400) without chromones showed only moderate improvement and only single point significance (FIG. 15A) after ten weeks of oral consumption.

Figure 16:
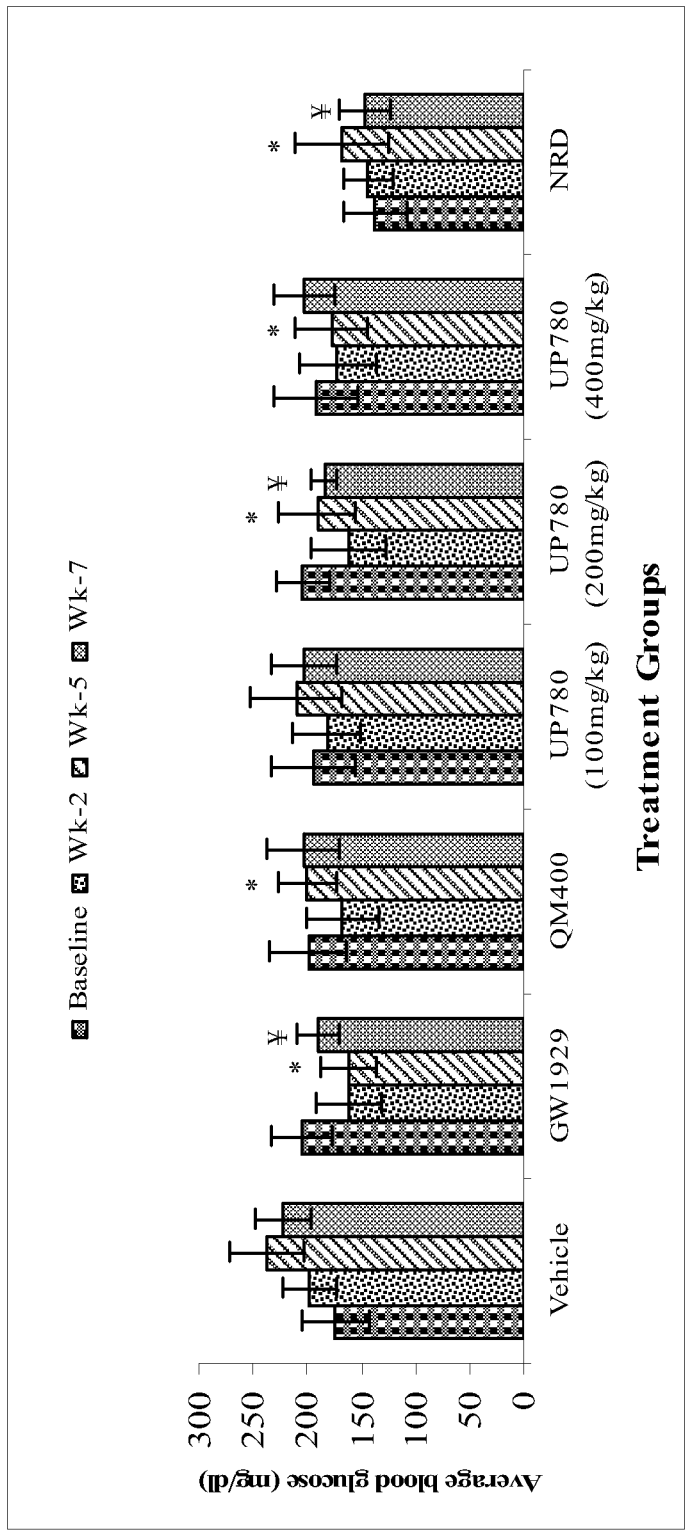
FIG. 16 illustrates graphically the consistent glucose lowering effect of UP780 administered at a dosage of 200 mg/kg. Fasting blood glucose levels were measured at baseline and 2, 5, and 7 weeks after treatment onset using 15-20 μl blood obtained from tail vein. Animals were treated with GW1929

The enriched *Aloe vera* gel powder with Aloesin also maintained consistently low levels of fasting blood glucose levels. Fasting glucose levels were separately monitored at 2, 5, and 7 weeks of treatment. As seen in FIG. 16, animals treated with 200 mg/kg UP780 and GW1929 showed statistically significant lower fasting glucose levels on both weeks (week 5 and 7) when compared to untreated vehicle. Mice treated with Qmatrix® and UP780 at 400 mg/kg exhibited similar lower levels of fasting blood glucose levels at week 5. On the other hand, the 100 mg/kg UP780 treated groups did maintain relatively high levels of fasting blood glucose to the untreated vehicle for all the weeks monitored, P≤0.05 (*). Similar data analysis showed that the percent reduction of fasting glucose levels in animals treated with 200 mg/kg UP780, were found to be 18%, 20% and 17% for weeks 2, 5, and 7, respectively when compared to vehicle (FIG. 17).

In this dose range finding study of Example 19, subsequent low levels of fasting triglyceride levels were observed for animals treated with UP780 and GW1929. After 7 weeks of daily oral treatment, percent reduction of fasting triglyceride levels to vehicle were 22.1%, 22%, 21.7%, and 22.7% for 200, 400 and 100 mg/kg of UP780 and GW1929, respectively (FIG. 18). However, the *Aloe vera* gel powder (Qmatrix QM400), which does not contain significant amounts of chromones, showed only 2% improvement of triglyceride level after 2 weeks of treatment, additionally this effect disappeared at two subsequent measurements. The unexpected and superior efficacy in lowering triglyceride levels by a chromone enriched plant extract was clearly demonstrated by this experiment.

As showed in the FIG. 19, no significant changes in cholesterol levels were noted for all the treatment groups, when compared to vehicle, $P \leq 0.05$. Furthermore, for all of the times observed, there were no significant body weight gain or feed consumption differences between groups for all the mice treated with GW1929, Qmatrix®, UP780 (100, 200 and 400 mg/kg) and vehicle. Even though animals in each treatment group including vehicle and normal rodent diet continued to gain weight throughout the study period, the body weight gain differences noticed between treatment groups were statistically insignificant at $P \leq 0.05$ (FIG. 20). In agreement with the body weight data, similar patterns of feed consumption were recorded for all the groups (FIG. 21).

Genomic studies, by definition, are studies of genome-wide scale, frequently by using DNA microarray chips containing probe-sets that cover all expressed genes. For a mammalian system, 25,000 genes are believed to be functional and expressed. After a microarray chip is hybridized to a cRNA/cDNA prepared from mRNA, the signals detected from the microarray chip should reflect the spectrum of gene expression of the tissue/cell source of the mRNA. Genes with expression variation, typically in thousands, are analyzed by the genome database for their participations in the biological pathways.

We have conducted microarray studies for UP780 as described in Example 20. The microarray chips used were the mouse genome 430 2.0 from Affymetrix, containing 45,000 probe-sets. Microarray data of gene expression variations were analyzed by a vigorous statistic method of ANOVA for the validity of gene expression variations. Key genes with expression variations were further validated by quantitative reverse transcription-PCR (QPCR) as described in Example 21. The treatment effects, detected by gene expression variations that affected metabolic and signaling pathways, were analyzed by the Ingenuity Pathway Analysis software and database (IPA5).

With high blood glucose levels, pancreatic β cells secrete insulin that causes glucose transporters in liver and muscle to translocate to the plasma membrane for glucose uptake and storage of glucose as glycogen. Insulin also increases fatty acid and triglyceride synthesis in liver and adipose tissue and the storage of fat in adipose tissue. Insulin resistance arises from faulty insulin receptor signaling cascade, causing decreased translocation of glucose transporters to the plasma membrane, decreased fat storage, and increased blood glucose and free fatty acids. High blood free fatty acid inactivates the insulin receptor substrate (IRS), and is a factor that induces insulin resistance.

A C57BL6 pre-diabetic mouse model used for the UP780 efficacy study was the source of mouse tissues for microarray. Mouse tissues were taken from lean control, high-fat-diet (also called vehicle), and high-fat-diet plus UP780 treatment at 200 mg/Kg for RNA extraction, each in triplicate. Tissues important for energy intake, metabolism, insulin resistance, obesity, and diabetes are liver, muscle, and fat. One data set of liver microarrays was completed. In general, high-fat-diet (LV) increased gene expression compared to lean control (LC), but many of the gene expression levels were decreased by high-fat-diet+UP780 (LUP, FIG. 23).

Figure 25B:
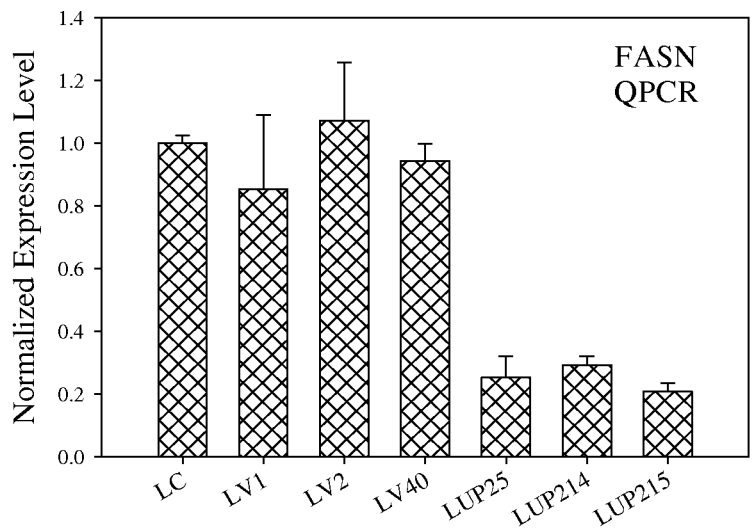

The most significant finding from the microarray and QPCR study was the reduction in fatty acid biosynthesis by UP780 illustrated in the Examples 20 and 21. Transcripts of the rate-limiting enzyme, acetyl-CoA carboxykinase (ACC2), and fatty-acid synthase (FASN) were decreased by UP780 3-fold and 3.5-fold, respectively as compared to a high-fat-diet, (Table 1 and FIGS. 24 and 25). With a high fat diet, the excess energy from glucose is converted to fat, with the inevitable consequence of increased plasma free fatty acid which causes insulin resistance in muscle. A direct consequence of UP780 in decreased fatty acid biosynthesis should be an enhanced insulin sensitivity and glucose tolerance, as observed in animal models.

In addition, mice deficient in stearoyl-CoA desaturase (SCD1), the committing enzyme for the synthesis of poly-unsaturated fatty acids, stay lean with a high fat diet. UP780 decreased the SCD1 transcripts 4.44-fold compared to high-fat-diet.

Microarray analysis also showed that UP780 decreased the transcript levels of the enzymes involved in the mitochondrial fatty acid β-oxidation compared to both lean control and high-fat-diet (Table 1). Decreased β-oxidation would normalize the total level of mitochondrial oxidation under high energy intake, with a possible consequence of normalized mitochondrial free oxygen radical generation.

High steroid level is known to feedback and decrease steroid biosynthesis, such was observed for both high-fat-diet and UP780 treatments, especially for the rate limiting enzyme HMG-CoA reductase (Table 1). UP780 increased CYP7A1 compared to high-fat-diet, with a possible beneficial consequence of increased bile acid biosynthesis.

Figure 26B:
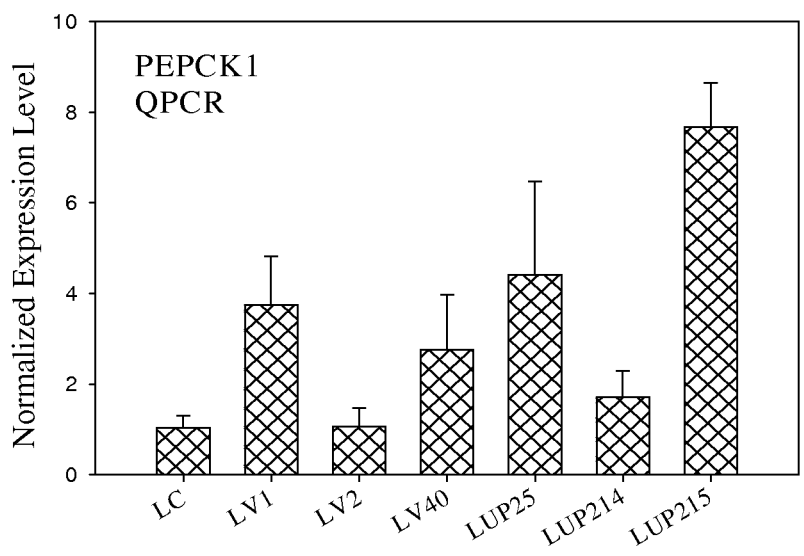

The overall gene expression variations in the glycolysis/gluconeogenesis pathway indicated little overall change because most of the enzymes involved are bi-directional. The rate-limiting enzyme of liver gluconeogenesis is phosphoenolpyruvate carboxykinase (PEPCK) within the pathway for pyruvate metabolism (Table 1). Microarray and QPCR showed a trend of increased PEPCK transcript by UP780, compared to lean control, but was equivalent to high-fat-diet (FIG. 26). This could increase blood glucose, to be avoided in anti-obesity anti-diabetic treatment. However, if muscle shows heightened glucose uptake and use by UP780, the net effect could be in overall balance as shown for the animal studies above.

Figure 27B:
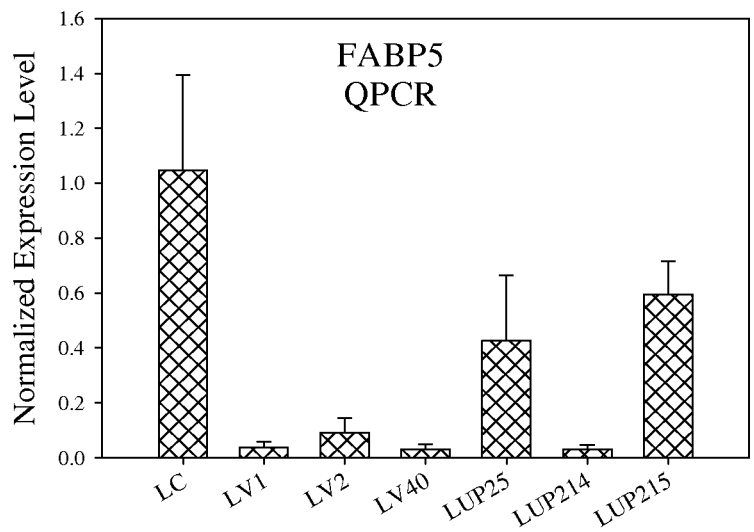

In the liver, the transcript for fatty acid binding protein FABP5 was increased 1.74-fold by UP780 compared to high-fat-diet as observed by microarray and QPCR (Table 1 and FIG. 27). Increased FABP5 would facilitate fatty acid transport and decrease free plasma fatty acids that cause insulin resistance. The plasma membrane LDL receptor was decreased by UP780, which could decrease LDL uptake from blood and decrease liver triglyceride content. Furthermore, CD36, for plasma membrane HDL, oxidized LDL, and fatty acid uptake, was also decreased by UP780 compared to high-fat-diet, which could further decrease liver fat content (Table 1).

High-fat-diet increased transcripts of genes involved in the PPARα/RXRα liver signaling pathway, which was decreased by UP780, especially for PPARα, CD36, and c-Jun. PPARα activation in the liver normalizes the plasma lipid profile by an elevation of HDL and a decrease of LDL. However, the transcript levels of ApoA1 and ApoA2, both lipoproteins for HDL, were not changed appreciably by either a high-fat-diet or UP780. The effect of UP780 on PPARα is worth further attention.

UP780 reduced many transcripts of enzymes involved in drug metabolism and detoxification, including CYP7B1, CYP2B9, CYP2C18, glutathione-S-transferase, and SOD3, an effect also worth further study (Table 1).

Figure 28B:
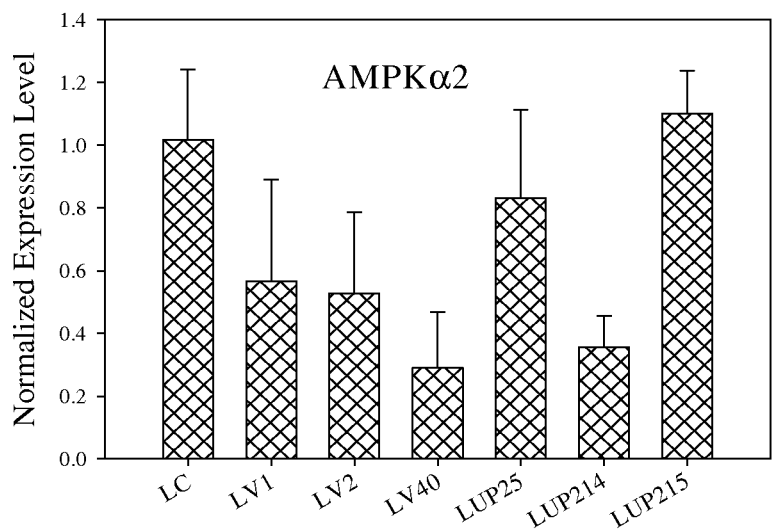

AMPK is viewed as the cell sensor for energy balance. Healthy cells maintain high ATP concentration at all time. AMPK is activated when the cell AMP/ATP ratio increases, a sign of energy stress (Hardie (2004) J Cell Sci 117:5479). Activation of AMPK inhibits glucose and fatty acid synthesis, increases glucose and fat uptake, increases glycolysis and fatty acid β-oxidation, and decreases protein synthesis and cell growth (Hardie (2004) Rev Endocrine & Metabolic Disorders 5:119). UP780 reversed the depression of AMPK transcript levels caused by high-fat-diet (FIG. 28).

A safety profile of the chromone enriched plant extract UP780 was carried out in CD-1 mice and this composition was determined to be well tolerated. As shown in Example 22, the daily administration of UP780 at 2.0 g/kg for 14 days in CD-1 mice caused no sign of morbidity or mortality throughout the duration of the study. Systematic daily examination of mice, for their physical condition and well being, showed no sign suggestive of test compound related toxicity or abnormality throughout the study. In this acute toxicity study, all mice continued to gain weight the course of study (FIGS. 22A and B). All major blood biochemistry readings were within normal ranges, with the exception that minor off-readings in electrolytes from the reference range were observed in this 14 day toxicity study. There were statistically significant differences in aspartate aminotransferase (AST), sodium, potassium and mean corpuscular hemoglobin concentration (MCHC) in females and total protein and blood urea nitrogen (BUN) in males treated with UP780, when compared to vehicle control, P≤0.05 (data not shown). Mean values observed for MCHC, total protein, and BUN were still within normal reference range; however, AST, sodium and potassium mean values were outside the normal range.

Gross examination results of all mice post mortem were generally normal for both vehicle control and UP780 treated animals (data not shown). There were no test article-related microscopic changes observed in any of the tissues specified for microscopic examination in the mice administered UP780 for 14 days. A few miscellaneous microscopic changes observed in the organs and tissues examined were the type that are frequently observed as spontaneously occurring changes in laboratory mice of this age and strain. Electrolyte imbalances observed could be caused by many conditions, including kidney and adrenal gland disorders, and any illness that results in vomiting and/or diarrhea. Low value of AST has no clinical significance. Because of lack of corresponding evidence in clinical observations, hematology values and histopathology results, we believe that these deviations from the normal values could be due to housing and laboratory conditions. Additionally, incidences like cell leakage as a result of hemolysis and splenic contraction due to psychological stress could result in false increase or decrease in analyte readings. Therefore, based on clinical findings and laboratory reports on hematology, blood chemistry and histopathology, it was concluded that there was no evidence of any systemic toxicity in any of the mice of this study at this dose. The vehicle or test article had no effect on the type, incidence or severity of these incidental findings.

The compounds of the instant invention, as well as the plants containing the compounds can be delivered as dietary supplements formulated in tablets, capsules, soft gels and also in regular diets and/or functional foods, power bars, fruit drinks and carbonated or regular beverages for use in the prevention and treatment of diseases and conditions mediated by insulin resistance, glucose intolerance, high triglyceride levels and imbalanced glucose levels in mammals, including but not limited to humans.

The preparation of compounds for administration in pharmaceutical compositions may be performed by a variety of methods well known to those skilled in the art. The chromones may be formulated as an herb powder in the form of their natural existence; as solvent and/or supercritical fluid extracts in different concentrations; as enriched and purified compounds through recrystallization, column separation, solvent partition, precipitation and other means, as a pure and/or a mixture containing substantially purified chromones prepared by synthetic methods.

Various delivery systems are known in the art and can be used to administer the therapeutic compositions of the invention, including powders, capsules, tablets, tinctures, sublingual delivery systems, food bars and various solutions including water, fruit juices, and carbonated soft drinks, creams and emulsions for oral administration. The compositions can be delivered as aqueous solutions, encapsulation in liposomes, microparticles, and microcapsules. Therapeutic compositions of the invention may be administered parenterally by injection, although other effective administration forms, such as intraarticular injection, inhalant mists, orally and topically active formulations, transdermal iontophoresis or suppositories are also envisioned. One preferred carrier is physiological saline solution, but it is contemplated that other pharmaceutically acceptable carriers may also be used. In one embodiment, it is envisioned that the carrier and chromone(s) constitute a physiologically compatible, slow release formulation. The primary solvent in such a carrier may be either aqueous or non-aqueous in nature. In addition, the carrier may contain other pharmacologically acceptable excipients for modifying or maintaining the pH, osmolarity, viscosity, clarity, color, sterility, stability, rate of dissolution, or odor of the formulation. Similarly, the carrier may contain still other pharmacologically acceptable excipients for modifying or maintaining the stability, rate of dissolution, release or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, cream, gel, emulsion, solid, or dehydrated or lyophilized powder. Such formulations may be stored either in a ready to use form or requiring reconstitution immediately prior to administration. The manner of administering formulations containing the compositions for systemic delivery may be via oral, subcutaneous, intramuscular, intravenous, topical, intranasal or vaginal or rectal suppository.

The amount of the composition that will be effective in the treatment of a particular disorder or condition will depend on the nature of the disorder of condition, which can be determined by standard clinical techniques. In addition, in vitro or in vivo assays may optionally be employed to help identify optimal dosage ranges. The precise dose to be employed in the formulation will also depend on the route of administration, and the seriousness or advancement of the disease or condition, and should be decided according to the practitioner and each patient's circumstances. Effective doses may be extrapolated from dose-response curves derived from in vitro or animal model test systems. For example, an effective amount of the composition of the invention is readily determined by administering graded doses of the composition and observing the desired effect.

The method of treatment according to this invention comprises administering internally or topically to a mammal including, but not limited to human in need thereof a therapeutically effective amount of the one or more chromones from a single source or multiple sources. The purity of the chromone or mixtures thereof can be in the range of 0.01% to 100%, depending on the methodology used to obtain the compound(s). The concentration of the chromone composition in oral, injectable, topical, aerosol suppository, intradermal administrations can be 0.001% to 99.99% by weight of the total amount in an appropriate formulation. Chromones can be used by standard routes of the administration selected from the group consisting of oral, topical, aerosol, suppository, intradermic, intramusclar, and intravenous administration with a daily dosage in a range of 0.01 mg/kg to 500 mg/kg body weight of mammals, especially humans.

EXAMPLES

The following examples are provided for illustrative purposes only and are not intended to limit the scope of the invention.

Example 1

Preparation of Organic and Aqueous Extracts from Dry Plants

Dried plant materials were ground to a particle size of no larger than 2 mm, and a portion of 20 g was extracted with 100 ml of methanol:dichloromethane (1:1) three times using an ASE 300 automatic extractor. The organic extract (OE) was obtained using rotary evaporation and speed-vacuum drying to remove solvent. Each plant extract was weighed (approximately 75 mg) and dissolved in 1.5 ml DMSO to make a solution with a concentration of 50 mg/ml.

Example 2

Mouse 3T3-L1 Cell Line and Culture Conditions

3T3-L1, an embryonic mouse cell line (American Type Culture Collection, Manassas, Va.), is a sub-strain of the 3T3 swiss albino line that can differentiate from a pre-adipose to adipose state. These preadipocytes were cultured in Dulbecco's modified Eagle medium (DMEM) containing 10% fetal bovine serum (FBS) (Mediatech, Inc., Herndon, Va.).

Example 3

Adiponectin ELISA Assay

To establish a differentiation protocol, the 3T3-L1 cells were plated into 96-well plates and cultured overnight to confluence. The confluent cells were induced to differentiate 2 days post-confluence. The induction was conducted with 0.5 mM isobutylmethylzanthine, 1.0 µM dexamethasone and 1.7 µM insulin (Sigma-Aldrich, St. Louis, Mo.) supplemented into culture media. On the 7$^{th}$ day the adipocytes were treated with the control compounds or plant extracts for 24 hours. All controls and plant extracts were solubilized in DMSO and added to the culture media at 1% of the total volume. Cell media was collected to measure the levels of adiponectin and assayed by enzyme-linked immunosorbent assay (ELISA) according to the manufacturer's protocol (R&D Systems, Minneapolis, Minn.). The assay sensitivity ranged from 31.25-2000 pg/mL. The positive controls were tested in a range from 0.01 to 300 µM (FIG. 1). The greatest fold increase in adiponectin level was observed at 1 µM for both indomethacin and troglitazone with 1.6- and 1.7-fold increase in adiponectin level, respectively.

Due to the poor signal to background ratio of the assay (less than 2), the previously mentioned protocol needed to be improved. Adipocytes were plated and differentiated as previously described. The cells were differentiated in the differentiation medium for 48 hours either with or without the addition of insulin. Then the cells were treated with the control compounds or plant extracts for only 48 hours post-differentiation. All other parameters were the same as previously mentioned. The indomethacin (FIG. 1) and troglitazone (data not shown) controls were tested at 10-100 µM and 3-30 µM respectively. The greatest increase in the level of adiponectin was 52-fold above the signal of baseline which was achieved by indomethacin treatment at 100 µM, while the lowest increase was 7-fold with indomethacin at 10 µM (FIG. 1B). The greatest increase of adiponectin by troglitazone treatment was achieved at 30 µM with a 49-fold increase, while the lowest fold increase of adiponectin level was observed at 3 µM with 24-fold (data not shown). Both of these compounds exhibited increases in adiponectin levels that were substantially higher than the published data.

Example 4

Screening Plant Extracts for Enhancement of Adiponectin Production in Adipocytes The plant extract library was screened using the adiponectin ELISA assay described in Example 3. The organic extracts isolated as described in Example 1, were screened in triplicate using indomethacin and troglitazone as controls. From the 2059 crude extracts, 14.9% of them (139 extracts) induced adiponectin productions higher than the control levels. Of those positive extracts, 37 extracts (1.8% of total) were more active than the lowest concentration (3 µM) of troglitazone control. These 37 crude extracts were retested with serial dilutions. Organic extracts from *Aloe ferox* leave exudates, P0017-OE, showed a good dose response curve of adiponectin induction (FIG. 2) and were selected for further evaluation.

Example 5

High Throughput Purification (HTP) of Active Organic Extracts from *Aloe ferox*

P0017-OE was selected for bioassay-guided active compound fractionation. P0017-OE (400 mg) was loaded onto a pre-packed normal phase flash column (2 cm ID×8.2 cm, 10 g of silica gel). The column was eluted using a Hitachi high throughput purification (HTP) system with a gradient mobile phase of (A) 50:50 EtOAc:hexane and (B) methanol from 100% A to 100% B in 30 minutes at a flow rate of 5 mL/min. The separation was monitored using a broadband wavelength UV detector and the fractions were collected in a 96-deep-well plate at 1.9 mL/well using a Gilson fraction collector. Fractions with similar UV absorption and retention times were combined into 8 sub-fractions and dried under low vacuum and centrifugation and named as P0017-OE-NP-F1, F2, F3, F4, F6, F6, F7 and F8 (FIG. 3). DMSO was used to dissolve each sub-fraction (50 µg/µl) and a portion (2 µl) was taken for adiponectin assay. P0017-OE-NP-F3 is the most active one in 8 sub-fractions.

Example 6

LC-MS/PDA De-Replication of P0017-OE-NP-Sub-Fractions

Because P0017-OE-NP-F3 was proven to be the most active sub-fraction in the adiponectin assay, LC-MS/PDA was utilized to analyze each P0017-OE-NP-sub-fraction obtained from HTP-fractionation, and compared with each other to find the unique compound peaks in P0017-OE-NP-F3. The most possible active compounds with molecular weight of 394 (aloesin) and 396 (aloesinol) in P0017-OE-NP-F3 were postulated based on molecular weights and literature search.

Example 7

Extraction and Purification of Aloesin and Aloesinol from *Aloe ferox*

Figure 4:
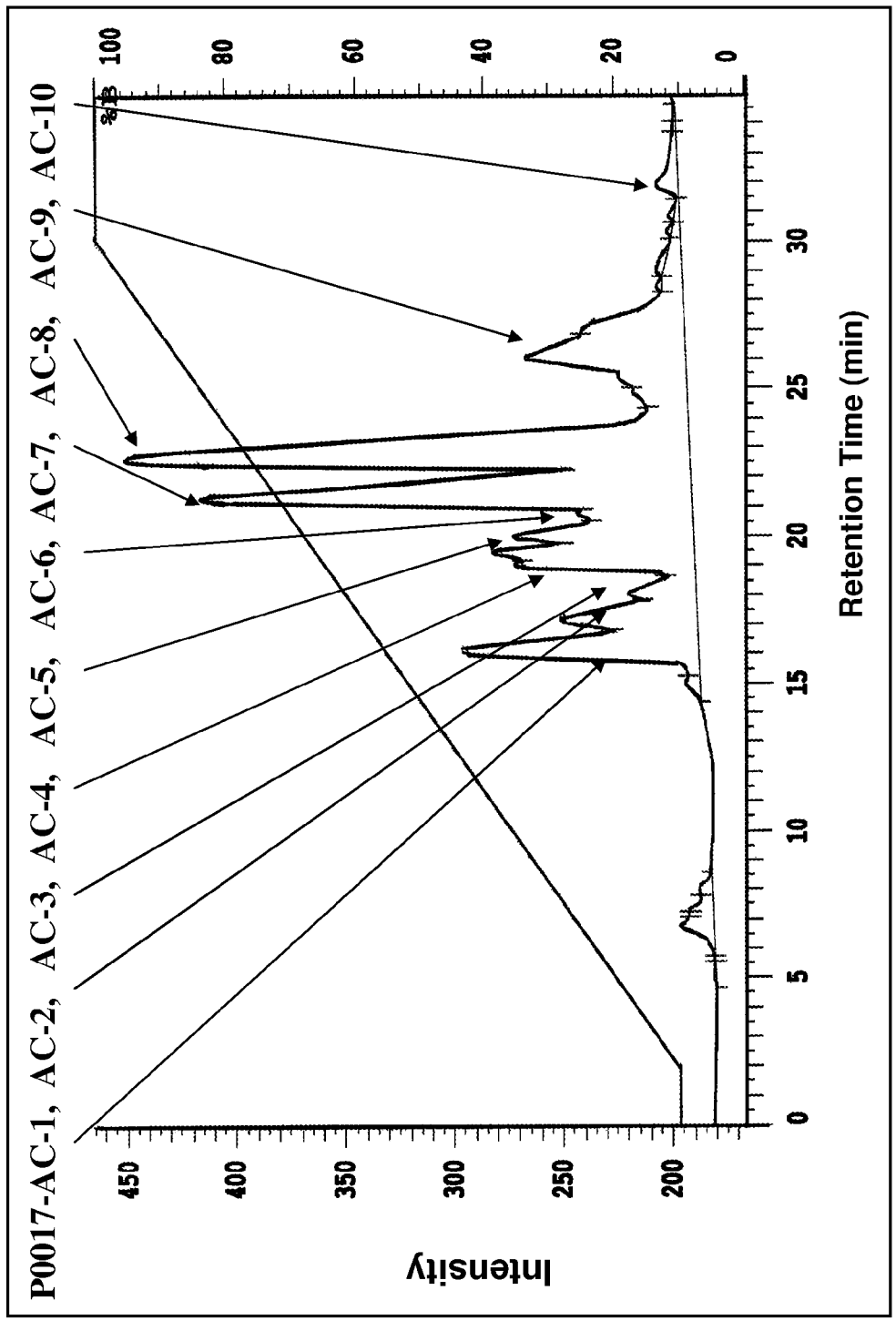
FIG. 4 illustrates the $C_{18}$ column fractionation of P0017-OE-NP-F3. P0017-AC1 and P0017-AC2 exhibited activity in the adiponectin assay and were identified as aloesin and aloesinol, respectively.

*Aloe ferox* leave exudates (P0017) (200 g) were extracted with methanol (3×). The combined methanol solution was evaporated under low vacuum to yield a methanol extract. Methanol extract (5 g) from P0017 was fractionated using the method described in Example 6 P0017-OE-NP-F3. The active fraction (equivalent to the P0017-OE-NP-F3 fraction of Example 6) (150 mg) was loaded onto a Phenomenex Luna $C_{18}$ column. (250×30 mm 10µ) and eluted on a Hitachi high throughput purification (HTP) system with a gradient mobile phase of water (A) and (B) methanol from 90% A to 100% B in 40 minutes at a flow rate of 5 mL/min and then 100% methanol washing for 10 minutes. The separation was monitored using a broadband wavelength UV detector and the fractions were collected into tubes by using a Gilson fraction collector. Ten major compound peaks were collected manually from 4 $C_{18}$-column runs. The 10 fractions were dried and purified by recrystallization and named as P0017-AC1, P0017-AC2, P0017-AC3, P0017-AC4, P0017-AC5, P0017-AC6, P0017-AC7, P0017-AC8, P0017-AC9 and P0017-AC10 (FIG. 4). P0017-AC1 and P0017-AC2 exhibited activity in the adiponectin assay and were identified as aloesin and aloesinol, respectively. The remaining 8 compounds are non-active or less active.

Example 8

Detailed Identification of Aloesin and Aloesinol

Figure 5:
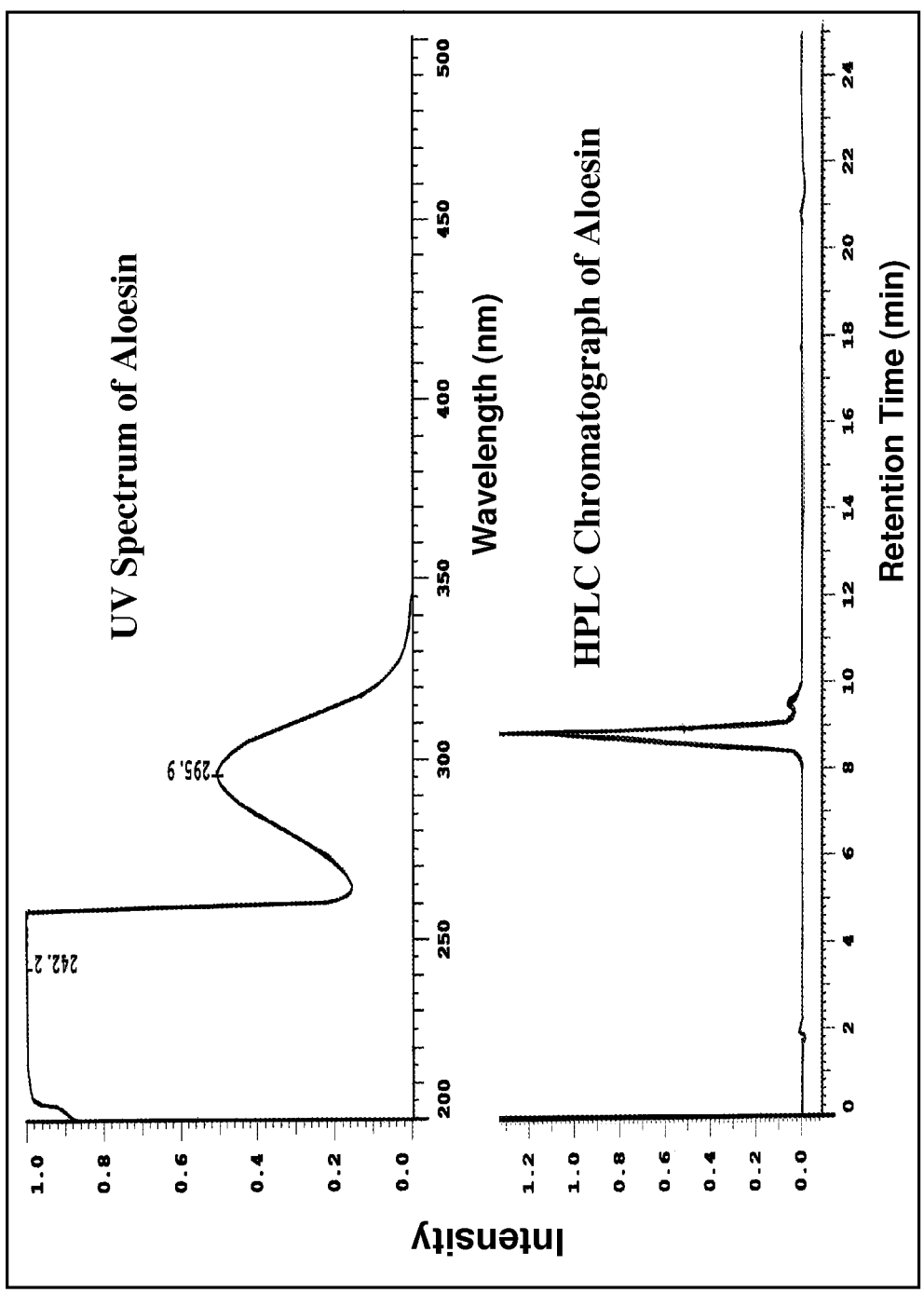
FIG. 5 depicts the identification of aloesin (UP394) via UV spectra elucidation and HPLC retention time comparison with authentic standard.

Aloesin (UP394): Yield, 2.4% from P0017-OE-NP-F3 (Purity>98%, HPLC); UV (Max): 248.4, and 295.9 nm; MS (ESI, negative ion detection): m/z 393 (M-1, 100%). The sample was spiked with an aloesin standard, which showed the same retention time on a HPLC chromatogram (FIG. 5).

Aloesinol (UP396): Yield, 1.4% from P0017-OE-NP-F3 (Purity>97%, HPLC); UV (Max): 248.4, and 295.9 nm; MS (ESI, negative ion detection): m/z 395 (M-1, 100%). The sample was spiked with an aloesinol standard, which showed same retention time on a HPLC chromatogram (FIG. 6).

Example 9

Preparation and Quantification of Aloesin from the Extract of *Aloe ferox*

Aloesin (UP394) was extracted from the whole leave extracts of *Aloe ferox*, isolated by a preparative chromatographic column and then further purified by recrystallization as described in U.S. Pat. No. 6,451,357 entitled "Method of Purification of Aloesin," which is incorporated herein by reference in its entirety. Briefly, the dried extracts were obtained from the whole leaf of *Aloe ferox* that had been previously dissolved in hot water and filtered to remove insoluble particles. The extract was then loaded onto a reverse phase column filled with CG-161 resins and aloesin (UP394) was eluted from the column with 20-30% methanol, after the column was washed with DI water. The 20-30% methanol eluent was combined and evaporated. The solid was recrystallized in alcohol/water solvent until reached to >90% purity without anthraquinone contamination (aloin A &B content not more than 100 ppm) according to the following HPLC method.

Chromones, such as aloesin (UP394), aloesinol (UP396), and aloeresin A were quantified against anthraquinone contaminants (i.e. Aloin A & B) using the HPLC method as published (Zahn (2007) Phytochem. Anal. 10:1002-1024). The analytical analysis were performed on an Hitachi L-7000 HPLC system with L-7100 pumps, L-7200 autosampler and L7300 column oven. The method used a Phenomenex IB SIL C18 column (250 mm×4.6 mm, 5µ particle size) coupled with a C18 guard cartridge. The mobile phase consisted of: water/methanol gradient starting with a ratio 66%:34% in the first 5 minutes. The ratio was changed to 24% water to 76% methanol by volume in 15 minutes and then was held at this ratio for another 2 minutes. The column was equilibrated at 66% water and 34% methanol for 5 minutes before the next sample injection. The flow rate was 1.0 ml/min. Chromones and anthraquinones were detected with an L-7400 UV detector at a wavelength of 297 nm. Chromones and anthraquinones were identified based on HPLC retention times and quantified based on peak areas against individual chromone and anthraquinone standards.

In the crude extract of *Aloe ferox*, the aloesin (UP394) content was reported as 24.8% by weight with anthraquinones at 22% (Zahn, (2007) Phytochem. Anal. 10: 1002-1024). The aloesin content in different *Aloe barbadensis* leaves has been reported as 0.32 mg/g (i.e. 0.032%) with total chromones at 0.1037%. The anthraquinone content (Aloin A & B) content on the other hand is almost four times higher (1.14 mg/g or 0.114%) than aloesin content (Park (1998) Phytochem. Anal. 9:186-191).

With the de-colorization method and other production processes, aloesin and anthraquinones are totally removed (both were below 50 ppm according to the HPLC analysis) from *Aloe vera* whole leaf spray dried gel powder (Lot # RM040805-02 & RM040805-05) and *Aloe vera* gel powder—Qmatrix dehydrated (Lot# RM120806-01). The isolated and purified aloesin (UP394) (Lot# A-2705 & Lot# I1506AW) from *Aloe ferox* leaf extract had purity at 93% and 100.6%, respectively with total anthraquinone less than 50 ppm. The anthraquinone free (<50 ppm total anthraquinones—Aloin A & B) aloesin (UP394) was utilized to produce chromone enriched composition—N931 and UP780 as illustrated in the following examples.

Example 10

Enhancement of Adiponectin Production by Aloesin (UP394) and Aloesinol (UP396)

Two pure chromones, UP394 (aloesin) and UP396 (aloesinol) were tested for increasing adiponectin production of adipocytes at 30 µM as described in Example 3. Aloesin and aloesinol showed a 2 and 3.2 fold increase in the production of adiponectin by adipocytes, respectively (FIG. 7).

Example 11

Detailed Preparation of N931 (Lot# D1205-01)

This unique composition of matter (N931) was produced by combining a pure chromone aloesin (UP394) isolated from the leave exudates of *Aloe ferox* with a whole leaf gel powder made from *Aloe vera*. The standardized chromone composition from two species of *Aloe* contained no less than 1.4% chromones—i.e. aloesin (UP394). Aloesin (UP394) was extracted from the whole leave exudates of *Aloe ferox*, isolated by a preparative chromatographic column and then further purified by recrystallization shown in Example 9 and further as described in U.S. Pat. No. 6,451,357 entitled "Method of Purification of Aloesin," which is incorporated herein by reference in its entirety. This unique standardized chromone composition was identified as N931.

0.811 kg of aloesin (Lot # A-2705 having a purity of 93% and 5% moisture content) was then added to 50 kg of *Aloe vera* whole leaf spray dried gel powder (Aloecorp Part No: 5020, Lot# RM-040805-02 and RM-040805-05) and the mixture was blended with a V-blender. Started the intensifier bar and run both intensifier bar and the shell for no less than 5 min and no more than 7 min blending time. Turned off only the intensifier bar and continue blending for no less than 5 min and no more than 10 min. Turned the intensifier bar on again and blend for no less than 5 min and no more than 7 min. Stopped blending, collected the blended material and quantified the Aloesin content in UP780 by HPLC method as 1.5% with total anthraquinone content less than 50 ppm quantified by HPLC method as illustrated in Example 9.

Example 12

High-Fat Diet Induced Pre-Diabetic Model

A high-fat diet induced animal model was developed and used for evaluation of potential therapeutic effects of chromone extracts. The C57BL/6J is a clinically relevant animal model that can be used in studies on metabolic disorders, pathophysiology of impaired glucose tolerance and for development of novel therapeutic agents (Ahren et al. (2004) Diabetes 53 (Supplement 3):S215-S219; Laakso et al. (2004) Diabetes Care 27:2253-2259; Kahn et al. (2004) Diabetes 53:3274-3285; Scheurink et al. (1998) European J Endo. 139:461-467; Yuan et al. (2002) Diabetes 51:1851-1858; Reitman et al. (2005) Endocrinology 145:3258-3264; Vlassara et al. (2005) Diabetes 54:2314-2319; Cawthome et al. (2002) Molecular and Cellular Proteomics 1:509-516). Methodology of model induction was first explained by Surwit et al. in 1988 (Diabetes, 37:1163-1167). In brief, impaired glucose tolerance and metabolic disorder like symptoms were inflicted successfully in C57BL/6J mice when fed with high fat diets for 8 weeks. Male C57BL/6J mice were purchased from Jackson Laboratories (Bar Harbor, Me.) at age of 6 weeks. One week after acclimation period, animals were divided into groups (n=5 or 6) and provided with high fat (45% kcal) rodent pellet (Research diets, Inc., New Brunswick, N.J.) and water ad libitum for 12 weeks except at times of glucose and insulin tolerance tests at which feed was withheld for three hours. Animals were maintained in a temperature controlled room (22.2° C.) on a 12 hour light-dark cycle. Blood glucose, cholesterol, and triglyceride were monitored every week for 12 weeks as described previously. Body weight measurement was taken once a week for 12 weeks.

Once induction of the metabolic disorders was confirmed by weekly monitoring of selected parameters (glucose, triglyceride and cholesterol) i.e. on the $8^{th}$ week, daily intraperitoneal treatment was initiated and maintained for 4 weeks. On each day of the study, test compounds and the positive control GW1929 (Tocris Bioscience, Ellisville Mo., batch #2A/58705) were dissolved in 0.5% methylcellulose (Sigma, St. Louise Mo., Lot#116H0857) and delivered at an intraperitoneal dose of 100 and 5 mg/kg, respectively. As GW1929 was not completely solublized in methylcellulose, it was first dissolved in DMSO (Sigma, St. Louise Mo., batch #064K0067). The final concentration of each compound, including the vehicle, was then adjusted to contain 5% DMSO before drug administration. The vehicle treated animals received 0.5% methylcellulose only. No detectable sign of irritation was observed after each compound or vehicle administration.

The positive control used, GW1929, N-(2-Benzoylphenyl)-O-[2-(methyl-2-pyridinylamino) ethyl]-L-tyrosine, is a yellow solid powder with a batch molecular weight of 504.59 (Tocris Bioscience, Ellisville Mo., batch #2A/58705). The compound is selective, orally active PPARγ agonist. Administered orally it decreases glucose, fatty acids and triglyceride levels in diabetic animal models (Brown et al. (1999) Diabetes 48:1415; Way et al. (2001) J. Biol. Chem. 276:25651-25653). Animals were provided with a high fat diet for 12 weeks. Treatment was started on week 8 and was continued for 4 weeks.

Example 13

The Effect of UP394 and UP396 on Insulin Resistance

An intraperitoneal glucose tolerance test was conducted using the C57BL/6J mice as described in Example 12 at a dose of 2 g/kg on day 18 of treatment with intraperitoneal administration of GW1929 (5 mg/kg), UP394 (100 mg/kg), UP396 (100 mg/kg) and vehicle. Animals were fasted for 3 hours before glucose administration. Blood glucose levels were measured at time 0, 30, 60, 90, and 120 minutes. The data are means±SD, n=6. Significant glucose utilization was observed at times 60, 90 and 120 minutes for GW1929 and UP396 when compared to vehicle, p<0.05. P-values for GW1929, UP394 and UP396 were 0.00, 0.87 and 0.43 at T0; 0.07, 0.16 and 0.23 at T30, respectively when compared to vehicle. P-values for UP394 were at T60 0.15; at T90 0.10 and at T120 0.17, when compared to vehicle (FIG. 8A).

Both UP394 and UP396 exhibited an effect on insulin sensitizing in the insulin tolerance test. An intraperitoneal insulin tolerance test was performed on C57BL/6J mice as demonstrated in Example 13 at a dose of 0.5 units/kg on day 24 of the treatment with oral administration of GW1929 (5 mg/kg), UP394 (100 mg/kg), UP396 (100 mg/kg) and vehicle. Animals were fasted for 3 hours before insulin injection. Blood glucose levels were measured at time 0, 30, 60, 90, and 120 minutes. The data are means±SD, n=6. A significant glucose clearance was observed at time points of T30, T60 and T90 for UP394 and UP396 as well as GW1929 when compared to vehicle, p<0.05. P-values for GW1929, UP394 and UP396 were 0.00, 0.14 and 0.67 at T0; and 0.08, 0.00 and 0.04 at T120, respectively when compared to vehicle (FIG. 8B).

Example 14

Effect of UP394 and UP396 on Insulin Sensitivities in High-Fat Diet Induced Insulin Resistance Model The effect of oral administration of UP394 (100 mg/kg) and UP396 (100 mg/kg) on insulin resistance was further demonstrated in the animals treated with compound UP394 and UP396. The insulin levels in those animals decreased significantly. The plasma insulin levels were measured with an ELISA kit for insulin (Crystal Chem—Chicago, Ill.). Animals were treated with GW1929, UP394 and UP396 and vehicle for 2 weeks after the 8-weeks on a high-fat diet (FIG. 9). Blood was collected by tail vein and spun down for plasma. Significant decreases in plasma insulin levels were observed on day 14 in the treatment groups of GW1929, UP394 and UP396 when compared to the vehicle group, P<0.05.

Example 15

Effect of N931 on Fasting Glucose Levels in db/db Mice

Fasting glucose levels of male db/db mice (8 mice in each group) treated with GW1929 (5 mg/kg), N931 (375 mg/kg) and vehicle were measured weekly. Animals were provided with T2018 rodent diet ad libitum except when fasting. Animals were fasted overnight before measurements were taken. As shown in FIG. 10, the glucose level in the vehicle-treated mice increased over time during the 10-week treatment. GW1929, the reference compound, was able to maintain the glucose levels at the baseline level, as expected. Similar to GW1929, N931 reduced the glucose levels substantially, starting from week 5 of the treatment. Fasting blood glucose levels were significantly lower for N-931 at week 6, 7, 9 and 10, when compared to vehicle P<0.05. At week 10 of treatment, 46% reduction of glucose level was observed in the group treated with N931.

Example 16

Effect of N931 on Insulin Resistance in db/db Mouse Model

An oral glucose tolerance test was conducted on db/db mice at a dose of 3 g/kg after 10 weeks of treatment. Animals were provided with T2018 rodent diet ad libitum except when fasting. Animals were fasted over night before glucose load. Mice (8 mice in each group) were treated with GW1929 (5 mg/kg), N931 (375 mg/kg) and vehicle for 10 weeks. Blood glucose levels were measured at time 0, 30, 60, 90, and 120 minutes after glucose loading. Significant glucose clearance from the circulation was observed at 0 and 120 minutes in the mice treated either with GW1929 or N-931 when compared to vehicle, P<0.05 (FIG. 11A). The results indicate that N931 has the ability to increase the glucose tolerance, therefore improve the insulin sensitivity of db/db mice.

An intraperitoneal insulin tolerance test was performed on db/db mice at a dose of 0.5 unit/kg after six weeks of treatment. Animals were fasted overnight before insulin injection. The db/db mice (8 in each group) were treated with GW1929 (5 mg/kg), N931 (375 mg/kg) and vehicle for 6 weeks. Blood glucose levels were measured at time 0, 30, 60, 90, and 120 minutes after injection of insulin. Again, improved insulin sensitivity was evident in the mice treated with GW1929 and N931. Significant glucose clearance was observed at times 0, 30 and 60 minutes for both GW1929 and N-931 when compared to vehicle, p<0.05 (FIG. 11B).

Example 17

Effect of N-931 on Triglyceride Level in db/db Mouse Model

Weekly fasting triglyceride levels of male db/db mice treated with GW1929 (5 mg/kg), N-931 (375 mg/kg) and vehicle were taken for 10 weeks. Animals were provided with T2018 rodent diet ad libitum except when fasting. Animals were fasted overnight before measurements were taken. The values indicated are percent triglyceride levels of vehicle, n=8. A significant reduction in triglyceride levels were found in animals treated with GW1929 and N-931 when compared to vehicle after 10 weeks of treatment, P<0.05 (FIG. 12).

Example 18

Preparation and Administration of a Chromone Enriched Composition (UP780)

This unique composition of matter (UP780) was produced by combining a pure chromone aloesin (UP394) isolated from the leave exudates of *Aloe ferox* with a leaf gel powder made from *Aloe vera*. The standardized chromone composition from two species of *Aloe* contained no less than 2% chromones—i.e. aloesin (UP394) with less than 50 ppm of total anthraquinones. The chromone, aloesin (UP394) was extracted from the whole leave exudates of *Aloe ferox*, isolated by a preparative chromatographic column and further purified by recrystallization as demonstrated in Example 9 and described in U.S. Pat. No. 6,451,357 entitled "Method of Purification of Aloesin," which is incorporated herein by reference in its entirety. This unique standardized chromone composition was identified as UP780.

The procedures are described below for the preparation of a 5 kg batch of *Aloe* chromone enriched *Aloe vera* gel powder, UP780. This is a standardized *Aloe* gel composition comprised of no less than 2% aloesin in *Aloe vera* gel powder. 0.11 g of aloesin (Lot # I1506AW) purified from *Aloe ferox* whole leaf exudates, having a purity of 100.6% was added to 4.90 kg of *Aloe vera* gel (Qmatrix® dehydrated) powder (Aloecorp Part No: AA8010XQ80 Lot# RM-120806-01). The mixture was blended to yield an *Aloe* chromone standardized composition UP780 (Lot # L1806QMAW-01). The content of aloesin (UP394) in the composition (UP780) was confirmed by HPLC as 2.2% without anthraquinone contamination.

Once an induction of the disease on animals after 8 weeks of high fat diets was confirmed by monitoring of selected parameters, daily oral treatment was initiated. On each day, the test articles and the positive control GW1929 (Tocris Bioscience, Ellisville, Mo., Batch #2A/58705) were dissolved in 0.5% methylcellulose (Sigma, St. Louise Mo., Lot#116H0857) and delivered at an oral dose of 100, 200 and 400 mg/kg of UP780 (Lot # L1806QMAW-01); 400 mg/kg of Qmatrix® *Aloe vera* gel powder (QM400, Lot# G6319103-L3) as well as 5 mg/kg of GW1929. As GW1929 was not completely solublized in methylcellulose, it was first dissolved in DMSO (Sigma, St. Louis, Mo., Batch#064K0067). The final concentration of test compounds, including the vehicle, was then adjusted to contain 5% DMSO before drug administration. The carrier vehicle treated animals received 0.5% methylcellulose only. No detectable sign of irritation was observed after each drug or vehicle administration.

Example 19

Efficacy and Dose-Range Study of UP780 on High Fat Diet Induced C57BL/6J Mice As described on Example 12, male C57BL/6J mice were purchased from Jackson Laboratories (Bar Harbor, Me.) at 6 weeks of age. One week after acclimation period, animals were divided into six groups (n=7) and provided with high fat (45% kcal) rodent pellet (Research Diets, Inc., New Brunswick, N.J.) and water ad libitum except at times of glucose and insulin tolerance tests at which feed was withheld for three hours. Animals were maintained in a temperature controlled room (22.2° C.) on a 12 hour light-dark cycle.

Three or four male C57BL/6J mice were housed in a mouse cage that had sections for feed and water. Feed intake was determined daily by measuring the difference between previously weighed high fat pellets value and what was left on the given day. Body weight measurement was taken once a week throughout the study.

Fasting blood glucose, total cholesterol and triglyceride levels were measured using 15-20 μl of blood obtained from tail vein. The IQ with prestige test strips (Walgreen, Home Diagnostics, Inc., Ft. Lauderdale, Fla.) blood glucose monitoring system for blood glucose and the CardioChek Analyzer with PTS panels test strips (Polymer Technology System, Inc, Indianapolis, Ind.) for cholesterol and triglyceride were used to determine whole blood values of cholesterol and triglycerides.

An intraperitoneal glucose tolerance test was conducted on day 0 (baseline), weeks 3, and 9 after onset of treatment. On the test day, animals were fasted for 3 hours and received intraperitoneal administration of glucose at a dose of 2 mg/g. Blood glucose levels were determined at time 0 (before glucose injection), 30, 60, 90, and 120 minutes post glucose delivery. Blood was obtained from tail vein. An intraperitoneal insulin tolerance test was performed in week 10. Animals were fasted for 3 hours and received intraperitoneal administration of insulin (Human recombinant expressed in yeast, Sigma, St. Louis, Mo., Lot #055K1321) at a dose of 0.51 U/kg. Blood glucose levels were determined at time 0 (before insulin injection), 30, 60, 90, and 120 minutes after insulin administration. Blood was obtained from tail vein.

Example 20

DNA Microarray Materials and Methods

Mice were divided into 7 treatment groups, and 3 animals were selected per group for tissue collection. After 10 weeks of treatment, mice were anesthetized with $CO_2$ gas and liver, body-wall muscle, and fat were collected within 5 minutes of euthanasia. Tissues were cut to less than 5 mm chunks and stored submerged in RNALater solution (Ambion) during tissue collection, and later on moved to a −80° C. freezer for long-term storage. For RNA isolation, mouse tissues were thawed and removed from the RNALater storage solution. An RNEasy total RNA isolation kit was used for liver total RNA extraction and an RNEasy fibrous tissue kit (Qiagen) was used for muscle total RNA extraction. The tissues were homogenized with a glass Dunce homogenator in a quanidine thiocyanate and β-mercaptoethanel containing RLT solution supplied in the RNEasy kits. Extracted RNAs were quantified by UV absorption at 260/280 nm wavelengths. RNA quality was determined using denaturing glyoxal agarose gel (1%) electrophoresis for the integrity of the 28S and the 18S rRNA bands and for the absence of the genomic DNA. When genomic DNA was observed from the gel, a second round of extraction was carried out with the RNEasy kit for the particular RNA sample.

Affymetrix mouse genome 430 2.0 array was selected for DNA microarray studies. Each array contains 45,000 probe sets of 34,000 mouse genes and control sequences for hybridization, poly-A, 100 normalization probe sets, and housekeeping genes. CoGenics was selected from a list of twelve Affymetrix-authorized service providers to carry out the process of cRNA synthesis, hybridization/wash, scanning, and data analysis using the Affymetrix GCOS software. CoGenics conducted their own internal RNA quality control upon receipt of RNA samples using a NanoDrop spectrophotometer and an Agilent 2100 Bioanalyzer. During microarray processing, Cogenics also conducted quality control for the cRNAs and for the microarray datasets. For mouse livers, treatment groups of lean-control (LC), high-fat-diet (LV), and high-fat-diet+UP780 at 200 mg/Kg (LUP) were selected for the microarray experiment, in total 9 arrays. All RNAs, cRNAs, and final microarray datasets passed quality control.

The Affymetrix mouse genome 430 2.0 array follows the standard Affymetrix array design: 11 probe pairs per probe set, each probe pair contains one perfect match (PM) and one miss match (MM) 25-mer oligonucleotide. Data analysis by GCOS used both PM and MM intensity values with background subtraction. For each probe set, all 11 PM values and 11 MM values were summarized into one intensity value. The data set of an array was then globally scaled based of the average intensity value and the target intensity value for array-to-array comparison. Independent microarray data analyses were also carried out using Affymetrix software "Expression Console". Besides the MAS5 algorism used in GOCS for intensity summarization, the algorisms RMA and PLIER were used in the Expression Console, also for intensity summarizations.

The utility of the MM probes has been a subject of debate. We therefore carried out additional microarray data analysis using only the PM values, background corrected, with the Bioconductor software. Each treatment group had 3 arrays. MA plots were used for the diagnosis of array consistency within the treatment groups. The inconsistency was normalized using the loess function of the Bioconductor microarray package in the R programming language. For each probe set of a treatment group, 33 PM values were integrated into one intensity value, $log_2$ transformed. Furthermore, between the treatment groups statistical tests of ANOVA were conducted for each probe-set using the 33 vs. 33 PM values. In total 3×45,000 ANOVA tests were performed between LUP vs. LV, LUP vs. LC, and LV vs. LC treatment groups. The significance of gene expression variations was tested by the methods of false discovery rate (FDR) and Holm's sequential Bonferroni correction, at a significance level $\alpha=0.05$.

Microarray data sets, typically in the range of thousands of genes with expression variations, require help from pathway analysis software to make sense of the biological significance. The mouse liver data sets of 3 each LC, LV, and LUP arrays summarized from the PM values were analyzed with the Ingenuity Pathway Analysis software IPA5 and the associated genome database. Three cutoff criteria of ANOVA p≤0.0001, log 2 intensity≥2.5, and log 2 ratio≥0.9 were applied. IPA5 produced 40 canonical pathways and 70 Functions, each with at least one of three data sets passed the threshold p-value of 0.05. (Canonical pathways are taken from the familiar signaling and metabolic pathway databases such as Science STKE and KEGG. Functions were based on the Gene Ontology (GO) database.) The well-established canonical pathways were analyzed in detail, especially the top metabolic pathways that showed clear influence of UP780 to nutrient metabolism. The pathway analysis data generated by IPA5 is set forth in Table 1.

Example 21

QPCR Analysis of Gene Expression Regulated by UP780

Total RNA extracted from mouse tissue was usually in excess of what is needed for the microarray experiment. The same total RNA samples used for microarray, therefore, were saved for QPCR validation of the microarray results, usually carried out months later. Total RNAs were routinely stored in a −80° C. freezer and no degradation was observed after long-term storage. For the reverse transcription reaction of cDNA synthesis from total RNA, we used the modified reverse transcriptase, Superscript III, together with the buffer, nucleotides, oligo(dT)$_7$ primer, and RNAse-free DNAseI supplied as reagents for Superscript III by Invitrogen. For each reaction, 5 µg of total RNA was used in a 50 µl reaction volume. The first strand cDNA was diluted with water to a 2.5× volume, and 2 µl of cDNA was used per a 50 µl QPCR reaction. The ABI primers and probe set of TaqMan Gene Expression Assay for each gene was confirmed by DNA sequence analysis before use. All probes were FAM-dye-labeled MGB probes. A 2× TaqMan Universal PCR Master Mix from ABI was used for QPCR reaction. Thermal cycling and detection was by an ABI 7700 Sequence Detector, with instrument control and QPCR data acquisition carried through the ABI SDS software. The relative quantification method of ΔΔDt was used and each QPCR 96-well plate contained a control cDNA (LC) and a control primers and probe set of the house-keeping gene GAPDH.

Example 22

Safety Evaluation of UP780

Purpose bred CD-1 mice were purchased from USDA approved laboratory animal vendor Charles River Laboratories, Inc. (Wilmington, Mass.). Animals were acclimated upon arrival for a week and used for the study at the age of 8 weeks. Mice were housed in a temperature controlled room (22.2° C.) on a 12 hour light-dark cycle and provided with feed and water ad libitum.

Baseline body weight measurement was taken on the first day of treatment prior to dosing and twice a week then after until necropsy day. All mice in the treatment group (n=10, 5 males and 5 females) were dosed orally for 14 consecutive days at a dosage of UP780 (Lot# L1806QMAW-01) 2.0 g/kg in 200 µl of water as vehicle, using a syringe and 18 gauge ball-tipped feeding needle. The control group (n=10, 5 males and 5 females) received 200 µl of water only.

Systematic clinical observations were made prior to test and daily during the study period. Animals were monitored for signs of toxicity including changes in coat color, fur, eyes, mucus membrane, locomotion, respiration, posture and other eccentric signs. Clinical observations were made for any pharmacotoxic signs such as, tremor, convulsion, diarrhea, lethargy, morbidity, fasciculation, droppings, salivation, discharges and dehydration. On the last day of the assay, all animals were anesthetized by 2% isoflurane at 2 L/min oxygen flow rate and blood was collected and shipped to Antech Diagnostics, Inc (Portland, Oreg.) for comprehensive mammalian profiling. Samples of whole blood (in lavender top microtainer) were used for hematological evaluations and plasma for clinical chemistry (green top microtainer with separator gel) evaluations. All animals were exsanguinated and examined for gross pathology. Once the abdominal cavity was opened, organs were subjected to gross examination and sample tissues of esophagus, stomach, duodenum, jejunum, ileum, cecum, colon, liver, rectum, brain (multiple sections), pituitary, peripheral nerve with muscle (sciatic), spinal cord (3 levels), eyes, adrenal glands, thyroid/parathyroid, pancreas, lungs and trachea, larynx, aorta (thoracic), heart, lymph nodes (cervical & mesenteric), spleen, thymus, kidneys, urinary bladder, testes, epididymides, seminal vesicles, prostate, cervix, ovaries, uterus, gall bladder, femur with joint, skin, salivary glands and tongue were collected, fixed with 10% buffered neutral formalin and sent to Research Pathology Services Inc (New Britain, Pa.) for histopathologic preparation and microscopic evaluations.

All non-discrete data from clinical chemistry, hematology, body weights and food consumption were tabulated with means and standard deviations. Interpretation of the results was made based on the pathology findings, abnormal physical signs and statistical evaluations of data.

TABLE 1

Gene expression variations from liver microarrays for genes involved in the metabolism pathways. Liver gene expression variations with $p < 0.0001$ by ANOVA are designated with (↑) for up-regulation and (↓) for down-regulation.

| Genes | Description | Liver (fold of gene expression variation) | | |
|---|---|---|---|---|
| | | LUP/LV | LUP/LC | LV/LC |
| Fatty Acid Biosynthesis | | | | |
| ACC2 | Acetyl-CoA carboxylase 2 | ↓ 3.01 | ↓ 2.54 | ↔ |
| FASN | Fatty acid synthase | ↓ 3.50 | ↓ 2.33 | ↑ 1.5 |
| ASCL3 | Acyl-CoA synthetase long-chain 3 | ↓ 2.07 | ↓ 1.49 | ↑ 1.39 |
| ACSS2 | Acyl-CoA synthetase, short chain 2 | ↓ 1.63 | ↓ 2.63 | ↓ 1.62 |
| SCD1 | Stearoyl-CoA desaturase | ↓ 4.44 | ↓ 3.94 | ↔ |
| FADS2 | Fatty acid desaturase 2 | ↓ 3.24 | ↓ 1.39 | ↑ 2.34 |
| ME1 | Malic enzyme 1 | ↓ 2.27 | ↓ 2.03 | ↔ |
| ACYL | ATP citrate lyase | ↓ 1.85 | ↓ 1.57 | ↔ |
| Fatty Acid Mitochondrial β-Oxidation | | | | |
| ALDH1B1 | Aldehyde dehydrogenase 1B1 | ↓ 2.82 | ↓ 1.75 | ↑ 1.61 |
| CPT1A | Carnitine palmitoyltransferase 1A | ↓ 1.86 | ↔ | ↑ 1.98 |

TABLE 1-continued

Gene expression variations from liver microarrays for genes
involved in the metabolism pathways. Liver gene expression
variations with p < 0.0001 by ANOVA are designated
with (↑) for up-regulation and (↓) for down-regulation.

| Genes | Description | Liver (fold of gene expression variation) | | |
|---|---|---|---|---|
| | | LUP/LV | LUP/LC | LV/LC |
| LCHAD | Trifunctional protein for β-oxidation, alpha subunit | ↓ 1.57 | ↔ | ↑ 1.49 |
| ACOT1 | Acyl-CoA thioesterase 1 | ↓ 5.87 | ↓ 3.04 | ↑ 1.93 |
| Steroid Biosynthesis | | | | |
| SREBF1 | Sterol regulatory element binding transcription factor 1 | ↓ 2.38 | ↓ 1.60 | ↑ 1.49 |
| HMGCR | 3-hydroxy-3-methylglutaryl-CoA reductase | ↓ 1.54 | ↓ 2.37 | ↓ 1.54 |
| MVD | Mevalonate dephospho decarboxylase | ↓ 2.36 | ↓ 2.06 | ↔ |
| CYP26A1 | Cytochrome P450, retinoic acid, drug metabolism | ↓ 2.88 | ↓ 6.53 | ↓ 2.27 |
| CYP7B1 | Cytochrome P450, bile synthesis | ↑ 1.94 | ↑ 1.91 | ↔ |
| Gluconeogenesis | | | | |
| PEPCK1 | Phosphoenolpyruvate carboxykinase 1 | ↔ | ↑ 1.89 | ↑ 2.06 |
| Fat Transport | | | | |
| CD36 | Thrombospondin receptor, long-chain fatty acid transpot | ↓ 2.67 | ↓ 1.25 | ↑ 2.14 |
| FABP5 | Fatty acid binding protein 5 | ↑ 1.74 | ↓ 1.67 | ↓ 2.89 |
| FABP4 | Fatty acid binding protein 4 | ↔ | ↑ 2.19 | ↑ 2.43 |
| LDLR | LDL receptor | ↓ 2.89 | ↓ 1.60 | ↑ 1.80 |
| PPARα | Peroxisome proliferator-activated receptor-α | ↓ 2.48 | ↔ | ↑ 2.11 |
| Xenobiotic Metabolism | | | | |
| CYP2B9 | Cytochrome P450 | ↓ 20.83 | ↓ 1.68 | ↑ 11.88 |
| CYP2C18 | Cytochrome P450 | ↔ | ↓ 2.98 | ↓ 2.60 |
| GSTA5 | Glutathione-S-transferase A5 | ↓ 1.67 | ↓ 4.08 | ↓ 2.10 |
| SOD3 | Superoxide dismutase 3, extracellular | ↓ 2.05 | ↓ 1.37 | ↑ 1.50 |

What is claimed is:

1. A method for treating pre-diabetic hyperglycemia, dyslipidemia, or both, comprising administering an effective amount of a composition comprising at least 1 wt % of one or more chromones combined with aloe gel.

2. The method according to claim 1, wherein the dyslipidemia is hypertriglyceridemia.

3. The method according to claim 1, wherein the one or more chromones are 7-hydroxy chromones having the following structure:

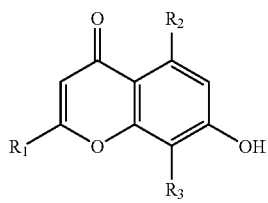

wherein $R_1$, $R_2$, and $R_3$ are independently selected from the group consisting of —H, —OH, —CH$_3$, —SH, alkyl, alkenyl, oxoalkyl, oxoalkenyl, hydroxylalkyl, hydroxylalkenyl, —OCH$_3$, —SCH$_3$, —OR, —SR, —NH$_2$, —NRH, —NR$_2$, —NR$_3^+$X$^-$, an ester selected from the group consisting of gallate, acetate, cinnamoyl and hydroxyl-cinnamoyl esters, trihydroxybenzoyl esters and caffeoyl esters; and a hexose or pentose, wherein said hexose or pentose is linked to the chromone by a carbon, nitrogen sulfur or oxygen and wherein said hexose or pentose is selected from the group consisting of aldopentoses, methyl aldopentose, aldohexoses, ketohexose and their chemical derivatives thereof including a dimer, trimer and other polymerized chromones;

wherein the alkyl and/or alkenyl group is a straight and/or branched chain having between 1-20 carbon atoms with and/or without double bonds and substitution group(s) selected from the group consisting —OH, =O and —OR in different positions;

X is selected from hydroxyl, chloride, iodide, sulfate, phosphate, acetate, fluoride, or carbonate; and R is an alkyl group having from 1-20 carbon atoms.

4. The method according to claim 1, wherein the one or more chromones are selected from aloesin, aloesin derivatives, aloesinol, aloeresin A, aloeresin C, aloeresin D, aloeresin E, aloeresin F, or any combination thereof.

5. The method according to claim 1, wherein the chromone is aloesin, aloesinol, or both.

6. The method according to claim 1, wherein the one or more chromones are isolated from a naturally occurring source or obtained by synthetic methods.

7. The method according to claim 6, wherein the naturally occurring source is a plant genus selected from *Acacia, Adina, Aloe, Alternaria, Amoora, Antidesma, Artemisia, Baeckea, Cassia, Clusea, Cnidium, Convolvulus, Epimedium, Eriosema, Eriostemon, Eugenia, Garcinia, Hypericum, Lindenbergia, Pancratium, Penicillium, Polygonum, Ptaeroxylon, Rheum, Sophora, Stephanitis, Syzygium, Talaromyces, Zonaria,* or any combination thereof.

8. The method according to claim 7, wherein the naturally occurring source is a plant selected from *Acacia catechu, Acacia concinna, Aloe arborescens, Aloe cremnophila, Aloe ferox, Aloe saponaria, Aloe vera* var. *chinensis, Aloe vera, Antidesma membranaceum, Artemisia capillaries, Baeckea frutescens, Epimedium sagittatum, Garcinia dulcis, Hypericum japonicum, Polygonum cuspidatum, Sophora tomentosa, Stephanitis rhododendri*, or any combination thereof.

9. The method according to claim 6, wherein the naturally occurring source is a plant part selected from stems, stem barks, trunks, trunk barks, twigs, tubers, roots, root barks, young shoots, seeds, rhizomes, flowers and other reproductive organs, leaves or other aerial parts, or any combination thereof.

10. The method according to claim 1, wherein the composition is administered in a dosage ranging from 0.01 to 500 mg/kg of body weight.

11. The method according to claim 1, wherein the composition is administered by a route selected from oral, topical, suppository, intravenous, intradermic, intragaster, intramuscular, intraperitoneal, or intravenous.

12. The method according to claim 1, wherein the aloe gel is isolated or enriched from *Aloe vera*.

13. The method according to claim 1, wherein the one or more chromones are isolated or enriched from *Aloe ferox*.

14. The method according to claim 1, wherein the composition comprises from 1 wt % to 10 wt % of the one or more chromones and from 90 wt % to 99 wt % of the aloe gel.

15. The method according to claim 14, wherein the one or more chromones are isolated or enriched from *Aloe ferox* and the aloe gel is isolated or enriched from *Aloe vera*.

16. The method according to claim 15, wherein the chromone is aloesin, aloesinol, or both.

17. The method according to claim 15, wherein the composition comprises no less than 1.4 wt % of the one or more chromones.

18. The method according to claim 17, wherein the chromone is aloesin, aloesinol, or both.

19. The method according to claim 1, wherein the composition comprises from 1 wt % to 5 wt % of the one or more chromones and from 95 wt % to 99 wt % of the aloe gel.

20. The method according to claim 19, wherein the one or more chromones are isolated or enriched from *Aloe ferox* and the aloe gel is isolated or enriched from *Aloe vera*.

21. The method according to claim 20, wherein the composition comprises no less than 2 wt % of the one or more chromones.

22. The method according to claim 21, wherein the chromone is aloesin, aloesinol, or both.

23. A method for promoting or maintaining healthy blood sugar levels, supporting blood sugar metabolism and/or reducing elevated blood sugar levels in a pre-diabetic subject, the method comprising administering an effective amount of a composition comprising at least 1 wt % of one or more chromones combined with aloe gel.

24. The method according to claim 23, wherein the one or more chromones are 7-hydroxy chromones having the following structure:

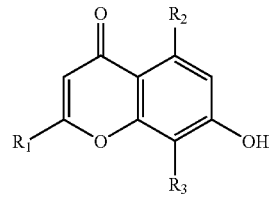

wherein $R_1$, $R_2$, and $R_3$ are independently selected from the group consisting of —H, —OH, —$CH_3$, —SH, alkyl, alkenyl, oxoalkyl, oxoalkenyl, hydroxylalkyl, hydroxylalkenyl, —$OCH_3$, —$SCH_3$, —OR, —SR, —$NH_2$, —NRH, —$NR_2$, —$NR_3^+X^-$, an ester selected from the group consisting of gallate, acetate, cinnamoyl and hydroxyl-cinnamoyl esters, trihydroxybenzoyl esters and caffeoyl esters; and a hexose or pentose, wherein said hexose or pentose is linked to the chromone by a carbon, nitrogen sulfur or oxygen and wherein said hexose or pentose is selected from the group consisting of aldopentoses, methyl aldopentose, aldohexoses, ketohexose and their chemical derivatives thereof; including a dimer, trimer and other polymerized chromones;

wherein the alkyl and/or alkenyl group is a straight and/or branched chain having between 1-20 carbon atoms with and/or without double bonds and substitution group(s) selected from the group consisting —OH, =O and —OR in different positions;

X is selected from hydroxyl, chloride, iodide, sulfate, phosphate, acetate, fluoride, or carbonate; and R is an alkyl group having from 1-20 carbon atoms.

25. The method according to claim 23, wherein the one or more chromones are selected from aloesin, aloesin derivatives, aloesinol, aloeresin A, aloeresin C, aloeresin D, aloeresin E, aloeresin F, or any combination thereof.

26. The method according to claim 23, wherein the chromone is aloesin, aloesinol, or both.

27. The method according to claim 23, wherein the one or more chromones are isolated from a naturally occurring source or obtained by synthetic methods.

28. The method according to claim 27, wherein the naturally occurring source is a plant genus selected from *Acacia, Adina, Aloe, Alternaria, Amoora, Antidesma, Artemisia, Baeckea, Cassia, Clusea, Cnidium, Convolvulus, Epimedium, Eriosema, Eriostemon, Eugenia, Garcinia, Hypericum, Lindenbergia, Pancratium, Penicillium, Polygonum, Ptaeroxylon, Rheum, Sophora, Stephanitis, Syzygium, Talaromyces, Zonaria*, or any combination thereof.

29. The method according to claim 28, wherein the naturally occurring source is a plant selected from *Acacia catechu, Acacia concinna, Aloe arborescens, Aloe cremnophila, Aloe ferox, Aloe saponaria, Aloe vera* var. *chinensis, Aloe vera, Antidesma membranaceum, Artemisia capillaries, Baeckea frutescens, Epimedium sagittatum, Garcinia dulcis, Hypericum japonicum, Polygonum cuspidatum, Sophora tomentosa, Stephanitis rhododendri*, or any combination thereof.

30. The method according to claim 27, wherein the naturally occurring source is a plant part selected from stems, stem barks, trunks, trunk barks, twigs, tubers, roots, root barks, young shoots, seeds, rhizomes, flowers and other reproductive organs, leaves or other aerial parts, or any combination thereof.

31. The method according to claim 23, wherein the composition is administered in a dosage ranging from 0.01 to 500 mg/kg of body weight.

32. The method according to claim 23, wherein the composition is administered by a route selected from oral, topical, suppository, intravenous, intradermic, intragaster, intramuscular, intraperitoneal, or intravenous.

33. The method according to claim 23, wherein the aloe gel is isolated or enriched from *Aloe vera*.

34. The method according to claim 33, wherein the one or more chromones are isolated or enriched from *Aloe ferox*.

35. The method according to claim 33, wherein the composition comprises from 1 wt % to 10 wt % of the one or more chromones and from 90 wt % to 99 wt % of the aloe gel.

36. The method according to claim 35, wherein the one or more chromones are isolated or enriched from *Aloe ferox* and the aloe gel is isolated or enriched from *Aloe vera*.

37. The method according to claim 36, wherein the chromone is aloesin, aloesinol, or both.

38. The method according to claim 36, wherein the composition comprises no less than 1.4 wt % of the one or more chromones.

39. The method according to claim 38, wherein the chromone is aloesin, aloesinol, or both.

40. The method according to claim 23, wherein the composition comprises from 1 wt % to 5 wt % of the one or more chromones and from 95 wt % to 99 wt % of the aloe gel.

41. The method according to claim 40, wherein the one or more chromones are isolated or enriched from *Aloe ferox* and the aloe gel is isolated or enriched from *Aloe vera*.

42. The method according to claim 41, wherein the composition comprises no less than 2 wt % of the one or more chromones.

43. The method according to claim 42, wherein the chromone is aloesin, aloesinol, or both.

44. A method for reducing elevated blood glucose levels, decreasing fasting blood glucose levels and/or improving glucose tolerance in a pre-diabetic subject, the method comprising administering to a subject an effective amount of a composition comprising at least 1 wt % of one or more chromones combined with aloe gel.

45. The method according to claim 44, wherein the one or more chromones are 7-hydroxy chromones having the following structure:

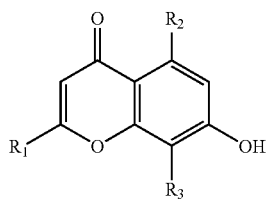

wherein $R_1$, $R_2$, and $R_3$ are independently selected from the group consisting of —H, —OH, —CH$_3$, —SH, alkyl, alkenyl, oxoalkyl, oxoalkenyl, hydroxylalkyl, hydroxylalkenyl, —OCH$_3$, —SCH$_3$, —OR, —SR, —NH$_2$, —NRH, —NR$_2$, —NR$_3^+$X$^-$, an ester selected from the group consisting of gallate, acetate, cinnamoyl and hydroxyl-cinnamoyl esters, trihydroxybenzoyl esters and caffeoyl esters; and a hexose or pentose, wherein said hexose or pentose is linked to the chromone by a carbon, nitrogen sulfur or oxygen and wherein said hexose or pentose is selected from the group consisting of aldopentoses, methyl aldopentose, aldohexoses, ketohexose and their chemical derivatives thereof; including a dimer, trimer and other polymerized chromones;

wherein the alkyl and/or alkenyl group is a straight and/or branched chain having between 1-20 carbon atoms with and/or without double bonds and substitution group(s) selected from the group consisting —OH, =O and —OR in different positions;

X is selected from hydroxyl, chloride, iodide, sulfate, phosphate, acetate, fluoride, or carbonate; and R is an alkyl group having from 1-20 carbon atoms.

46. The method according to claim 44, wherein the one or more chromones are selected from aloesin, aloesin derivatives, aloesinol, aloeresin A, aloeresin C, aloeresin D, aloeresin E, aloeresin F, or any combination thereof.

47. The method according to claim 44, wherein the chromone is aloesin, aloesinol, or both.

48. The method according to claim 44, wherein the one or more chromones are isolated from a naturally occurring source or obtained by synthetic methods.

49. The method according to claim 8, wherein the naturally occurring source is a plant genus selected from *Acacia, Adina, Aloe, Alternaria, Amoora, Antidesma, Artemisia, Baeckea, Cassia, Clusea, Cnidium, Convolvulus, Epimedium, Eriosema, Eriostemon, Eugenia, Garcinia, Hypericum, Lindenbergia, Pancratium, Penicillium, Polygonum, Ptaeroxylon, Rheum, Sophora, Stephanitis, Syzygium, Talaromyces, Zonaria*, or any combination thereof.

50. The method according to claim 49, wherein the naturally occurring source is a plant selected from *Acacia catechu, Acacia concinna, Aloe arborescens, Aloe cremnophila, Aloe ferox, Aloe saponaria, Aloe vera* var. *chinensis, Aloe vera, Antidesma membranaceum, Artemisia capillaries, Baeckea frutescens, Epimedium sagittatum, Garcinia dulcis, Hypericum japonicum, Polygonum cuspidatum, Sophora tomentosa, Stephanitis rhododendri*, or any combination thereof.

51. The method according to claim 48, wherein the naturally occurring source is a plant part selected from stems, stem barks, trunks, trunk barks, twigs, tubers, roots, root barks, young shoots, seeds, rhizomes, flowers and other reproductive organs, leaves or other aerial parts, or any combination thereof.

52. The method according to claim 44, wherein the composition is administered in a dosage ranging from 0.01 to 500 mg/kg of body weight.

53. The method according to claim 44, wherein the composition is administered by a route selected from oral, topical, suppository, intravenous, intradermic, intragaster, intramuscular, intraperitoneal, or intravenous.

54. The method according to claim 44, wherein the aloe gel is isolated or enriched from *Aloe vera*.

55. The method according to claim 44, wherein the one or more chromones are isolated or enriched from *Aloe ferox*.

56. The method according to claim 44, wherein the composition comprises from 1 wt % to 10 wt % of the one or more chromones and from 90 wt % to 99 wt % of the aloe gel.

57. The method according to claim 56, wherein the one or more chromones are isolated or enriched from *Aloe ferox* and the aloe gel is isolated or enriched from *Aloe vera*.

58. The method according to claim 57, wherein the chromone is aloesin, aloesinol, or both.

59. The method according to claim 57, wherein the composition comprises no less than 1.4 wt % of the one or more chromones.

60. The method according to claim 59, wherein the chromone is aloesin, aloesinol, or both.

61. The method according to claim 44, wherein the composition comprises from 1 wt % to 5 wt % of the one or more chromones and from 95 wt % to 99 wt % of the aloe gel.

62. The method according to claim 61, wherein the one or more chromones are isolated or enriched from *Aloe ferox* and the aloe gel is isolated or enriched from *Aloe vera*.

63. The method according to claim 62, wherein the composition comprises no less than 2 wt % of the one or more chromones.

64. The method according to claim 63, wherein the chromone is aloesin, aloesinol, or both.

65. A method for regulating healthy insulin levels, reducing the risk of insulin resistance and/or improving insulin sensitivity in a pre-diabetic subject, the method comprising administering to a subject an effective amount of a composition comprising at least 1 wt % of one or more chromones combined with aloe gel.

66. The method according to claim 65, wherein the one or more chromones are 7-hydroxy chromones having the following structure:

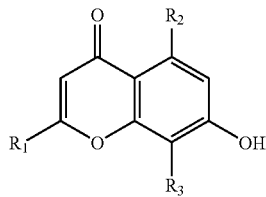

wherein $R_1$, $R_2$, and $R_3$ are independently selected from the group consisting of —H, —OH, —CH$_3$, —SH, alkyl, alkenyl, oxoalkyl, oxoalkenyl, hydroxylalkyl, hydroxylalkenyl, —OCH$_3$, —SCH$_3$, —OR, —SR, —NH$_2$, —NRH, —NR$_2$, —NR$_3^+$X$^-$, an ester selected from the group consisting of gallate, acetate, cinnamoyl and hydroxyl-cinnamoyl esters, trihydroxybenzoyl esters and caffeoyl esters; and a hexose or pentose, wherein said hexose or pentose is linked to the chromone by a carbon, nitrogen sulfur or oxygen and wherein said hexose or pentose is selected from the group consisting of aldopentoses, methyl aldopentose, aldohexoses, ketohexose and their chemical derivatives thereof; including a dimer, trimer and other polymerized chromones;

wherein the alkyl and/or alkenyl group is a straight and/or branched chain having between 1-20 carbon atoms with and/or without double bonds and substitution group(s) selected from the group consisting —OH, =O and —OR in different positions;

X is selected from hydroxyl, chloride, iodide, sulfate, phosphate, acetate, fluoride, or carbonate; and R is an alkyl group having from 1-20 carbon atoms.

67. The method according to claim 65, wherein the one or more chromones are selected from aloesin, aloesin derivatives, aloesinol, aloeresin A, aloeresin C, aloeresin D, aloeresin E, aloeresin F, or any combination thereof.

68. The method according to claim 65, wherein the chromone is aloesin, aloesinol, or both.

69. The method according to claim 65, wherein the one or more chromones are isolated from a naturally occurring source or obtained by synthetic methods.

70. The method according to claim 69, wherein the naturally occurring source is a plant genus selected from *Acacia, Adina, Aloe, Alternaria, Amoora, Antidesma, Artemisia, Baeckea, Cassia, Clusea, Cnidium, Convolvulus, Epimedium, Eriosema, Eriostemon, Eugenia, Garcinia, Hypericum, Lindenbergia, Pancratium, Penicillium, Polygonum, Ptaeroxylon, Rheum, Sophora, Stephanitis, Syzygium, Talaromyces, Zonaria*, or any combination thereof.

71. The method according to claim 70, wherein the naturally occurring source is a plant selected from *Acacia catechu, Acacia concinna, Aloe arborescens, Aloe cremnophila, Aloe ferox, Aloe saponaria, Aloe vera* var. *chinensis, Aloe vera, Antidesma membranaceum, Artemisia capillaries, Baeckea frutescens, Epimedium sagittatum, Garcinia dulcis, Hypericum japonicum, Polygonum cuspidatum, Sophora tomentosa, Stephanitis rhododendri*, or any combination thereof.

72. The method according to claim 69, wherein the naturally occurring source is a plant part selected from stems, stem barks, trunks, trunk barks, twigs, tubers, roots, root barks, young shoots, seeds, rhizomes, flowers and other reproductive organs, leaves or other aerial parts, or any combination thereof.

73. The method according to claim 65, wherein the composition is administered in a dosage ranging from 0.01 to 500 mg/kg of body weight.

74. The method according to claim 65, wherein the composition is administered by a route selected from oral, topical, suppository, intravenous, intradermic, intragaster, intramuscular, intraperitoneal, or intravenous.

75. The method according to claim 65, wherein the aloe gel is isolated or enriched from *Aloe vera*.

76. The method according to claim 65, wherein the one or more chromones are isolated or enriched from *Aloe ferox*.

77. The method according to claim 65, wherein the composition comprises from 1 wt % to 10 wt % of the one or more chromones and from 90 wt % to 99 wt % of the aloe gel.

78. The method according to claim 77, wherein the one or more chromones are isolated or enriched from *Aloe ferox* and the aloe gel is isolated or enriched from *Aloe vera*.

79. The method according to claim 78, wherein the chromone is aloesin, aloesinol, or both.

80. The method according to claim 78, wherein the composition comprises no less than 1.4 wt % of the one or more chromones.

81. The method according to claim 80, wherein the chromone is aloesin, aloesinol, or both.

82. The method according to claim 65, wherein the composition comprises from 1 wt % to 5 wt % of the one or more chromones and from 95 wt % to 99 wt % of the aloe gel.

83. The method according to claim 82, wherein the one or more chromones are isolated or enriched from *Aloe ferox* and the aloe gel is isolated or enriched from *Aloe vera*.

84. The method according to claim 83, wherein the composition comprises no less than 2 wt % of the one or more chromones.

85. The method according to claim 84, wherein the chromone is aloesin, aloesinol, or both.

* * * * *

UNITED STATES PATENT AND TRADEMARK OFFICE
CERTIFICATE OF CORRECTION

PATENT NO.        : 8,852,657 B2                                    Page 1 of 1
APPLICATION NO.   : 11/971523
DATED             : October 7, 2014
INVENTOR(S)       : Ji-Fu Zhao et al.

It is certified that error appears in the above-identified patent and that said Letters Patent is hereby corrected as shown below:

In the claims

Column 44, Line 41:
"hexose and their chemical derivatives thereof including" should read, --hexose and their chemical derivatives thereof; including--.

Column 47, Line 7:
"34. The method according to claim 33, wherein the one or" should read, --34. The method according to claim 23, wherein the one or--.

Column 47, Line 9:
"35. The method according to claim 33, wherein the" should read, --35. The method according to claim 23, wherein the--.

Column 48, Line 18:
"49. The method according to claim 8, wherein the naturally" should read, --49. The method according to claim 48, wherein the naturally--.

Signed and Sealed this
Third Day of May, 2016

Michelle K. Lee
*Director of the United States Patent and Trademark Office*